US011318166B2

(12) United States Patent
Gazit et al.

(10) Patent No.: US 11,318,166 B2
(45) Date of Patent: May 3, 2022

(54) METHOD FOR NON SURGICAL REPAIR OF VERTEBRAL COMPRESSION FRACTURES

(71) Applicant: Cedars-Sinai Medical Center, Los Angeles, CA (US)

(72) Inventors: Dan Gazit, Los Angeles, CA (US); Edward M. Schwarz, Rochester, NY (US); Hyun Bae, Los Angeles, CA (US); Gadi Pelled, Los Angeles, CA (US); Zulma Gazit, Los Angeles, CA (US); Dmitriy Sheyn, Los Angeles, CA (US); Wafa Tawackoli, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 130 days.

(21) Appl. No.: 15/315,704

(22) PCT Filed: Jun. 4, 2015

(86) PCT No.: PCT/US2015/034275
§ 371 (c)(1),
(2) Date: Dec. 1, 2016

(87) PCT Pub. No.: WO2018/187994
PCT Pub. Date: Dec. 10, 2015

(65) Prior Publication Data
US 2017/0119823 A1 May 4, 2017

Related U.S. Application Data

(60) Provisional application No. 62/007,793, filed on Jun. 4, 2014, provisional application No. 62/129,720, filed on Mar. 6, 2015.

(51) Int. Cl.
| A61K 35/28 | (2015.01) |
| A61K 38/18 | (2006.01) |
| A61K 38/29 | (2006.01) |
| A61K 9/00  | (2006.01) |

(52) U.S. Cl.
CPC ............ *A61K 35/28* (2013.01); *A61K 9/0019* (2013.01); *A61K 38/1875* (2013.01); *A61K 38/29* (2013.01)

(58) Field of Classification Search
None
See application file for complete search history.

(56) References Cited

U.S. PATENT DOCUMENTS

| 5,510,370 | A  | * | 4/1996  | Hock ..................... A61K 38/29 514/249 |
| 6,077,987 | A  | * | 6/2000  | Breitbart ............ A61K 38/1875 424/422 |
| 2004/0033950 | A1 | * | 2/2004  | Hock ..................... A61K 38/29 514/11.8 |
| 2005/0085543 | A1 |   | 4/2005  | Wallimann et al. |
| 2005/0112091 | A1 | * | 5/2005  | DiMauro ............ A61B 17/3472 424/85.1 |
| 2007/0161567 | A1 |   | 7/2007  | Gaich et al. |
| 2007/0281889 | A1 | * | 12/2007 | Scadden ................ A61K 35/28 424/184.1 |
| 2009/0291061 | A1 |   | 1/2009  | Riordan et al. |
| 2009/0155216 | A1 | * | 6/2009  | Yamada ............... A61L 27/3804 424/93.3 |
| 2011/0165128 | A1 | * | 7/2011  | Doronin ............... C12N 5/0663 424/93.7 |
| 2011/0206648 | A1 |   | 8/2011  | Mason et al. |
| 2012/0263687 | A1 |   | 10/2012 | Varney et al. |

FOREIGN PATENT DOCUMENTS

| EP | 3151847 B1   | 7/2020 |
| JP | 2017520537 A | 7/2017 |
| WO | 2015187994 A1 | 12/2015 |

OTHER PUBLICATIONS

Tu et al. Treatment of Repeated and Multiple New-Onset Osteoporotic Vertebral Compression Fractures with Teriparatide. Journal or Clinical Neuroscience, 2012. 19:532-535.*
Pfeilschifter et. al. Parathyroid Hormone Increases the Concentration of Insulin-like Growth Factor-1 and Transforming Growth Factor Beta 1 in Rat Bone. Journal of Clinical Investigation, 1995. 96:767-774.*
Forteo Packaging Insert, Eli Lilly and Company, 2002. 21 pages.*
PCT/US2015/034275 International Search Report and Written Opinion dated Nov. 2, 2015; 9 pages.
Extended European Search Report of EP 15803714.3, dated Nov. 10, 2017, 7 Pages.
California's Stem Cell Agency, Systemic Adult Stem Cell Therapy for Osteoporosis-Related Vertebral Compression Fractures, 2010, 3 Pages.
Gazit et al., Systemic Adult Stem Cell Therapy for Vertebral Compression Fractures, Advances in Orthopaedics—Winter 2017, 2017, pp. 1-4.

(Continued)

*Primary Examiner* — James D Schultz
*Assistant Examiner* — Kimberly A Aron
(74) *Attorney, Agent, or Firm* — Nixon Peabody LLP; Linda B. Huber

(57) ABSTRACT

Described herein are methods and compositions using PTH and mesenchymal stem cells (MSCs) for treatment of osteoporosis, bone fractures, and related conditions. Administration of both PTH and MSCs leads to increased homing of MSCs to sites of vertebral bone and rib fracture. The described methods and compositions provide therapeutic approaches that rely, in-part, on stem cell capacity for regeneration and repair. The potential for enhanced bone formation and fracture repair may allow for both preventative and palliative treatments in osteoporotic patients, with combined PTH+MSC therapy producing bone regeneration capacity that is significantly superior to either treatment alone.

4 Claims, 34 Drawing Sheets

(56) References Cited

OTHER PUBLICATIONS

Yu et al., Parathyroid Hormone Induces Differentiation of Mesenchymal Stromal/Stem Cells by Enhancing Bone Morphogenetic Protein Signaling, Journal of Bone and Mineral Research, 2012, vol. 27(9), pp. 2001-2014.

* cited by examiner

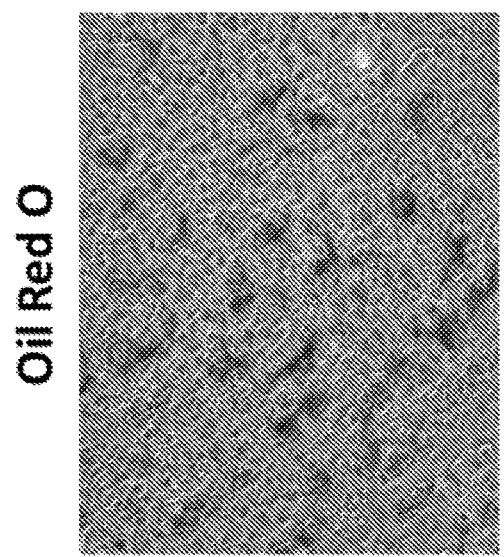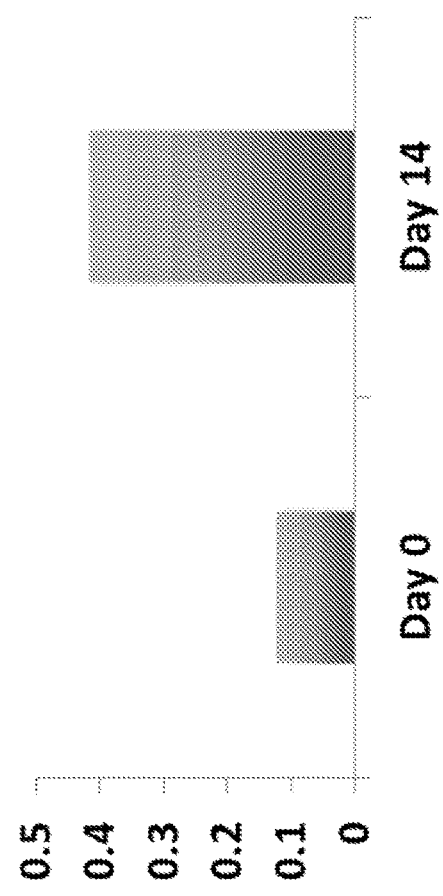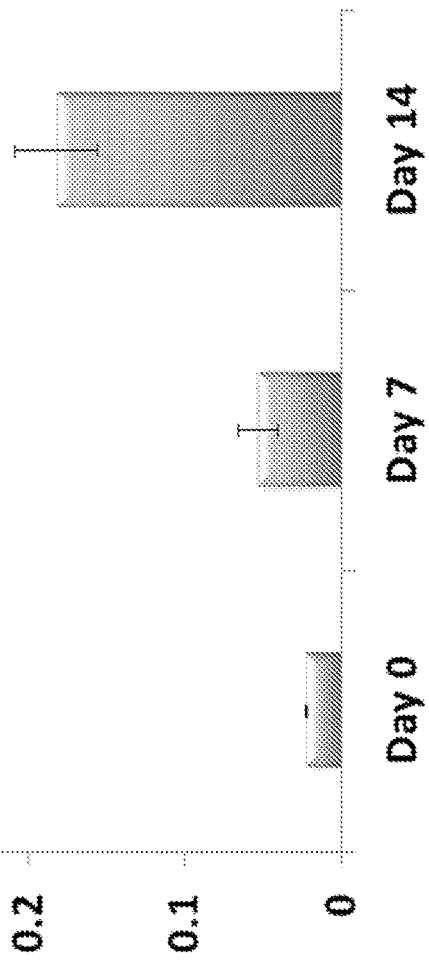
Fig. 2A
Fig. 2B

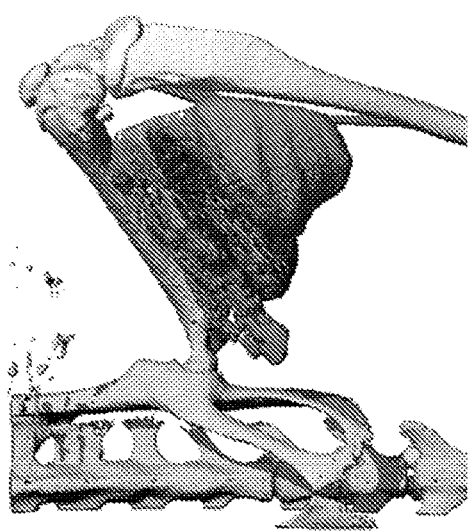
Fig. 3A
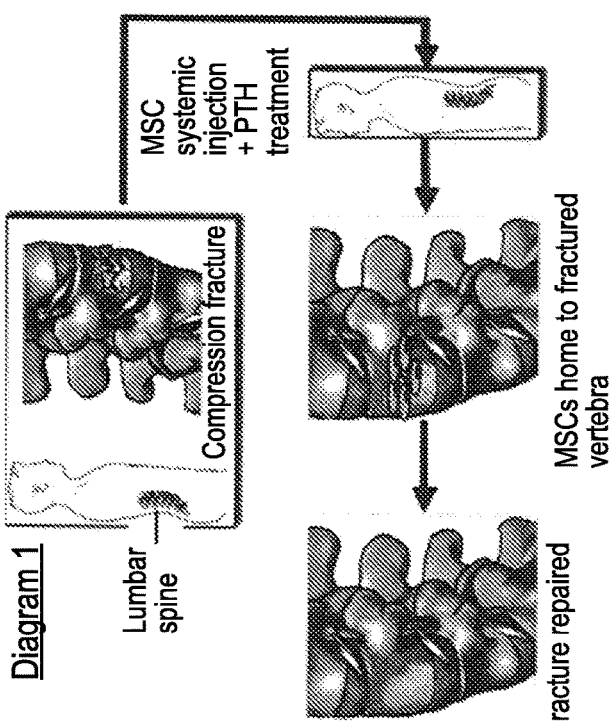
Fig. 3B

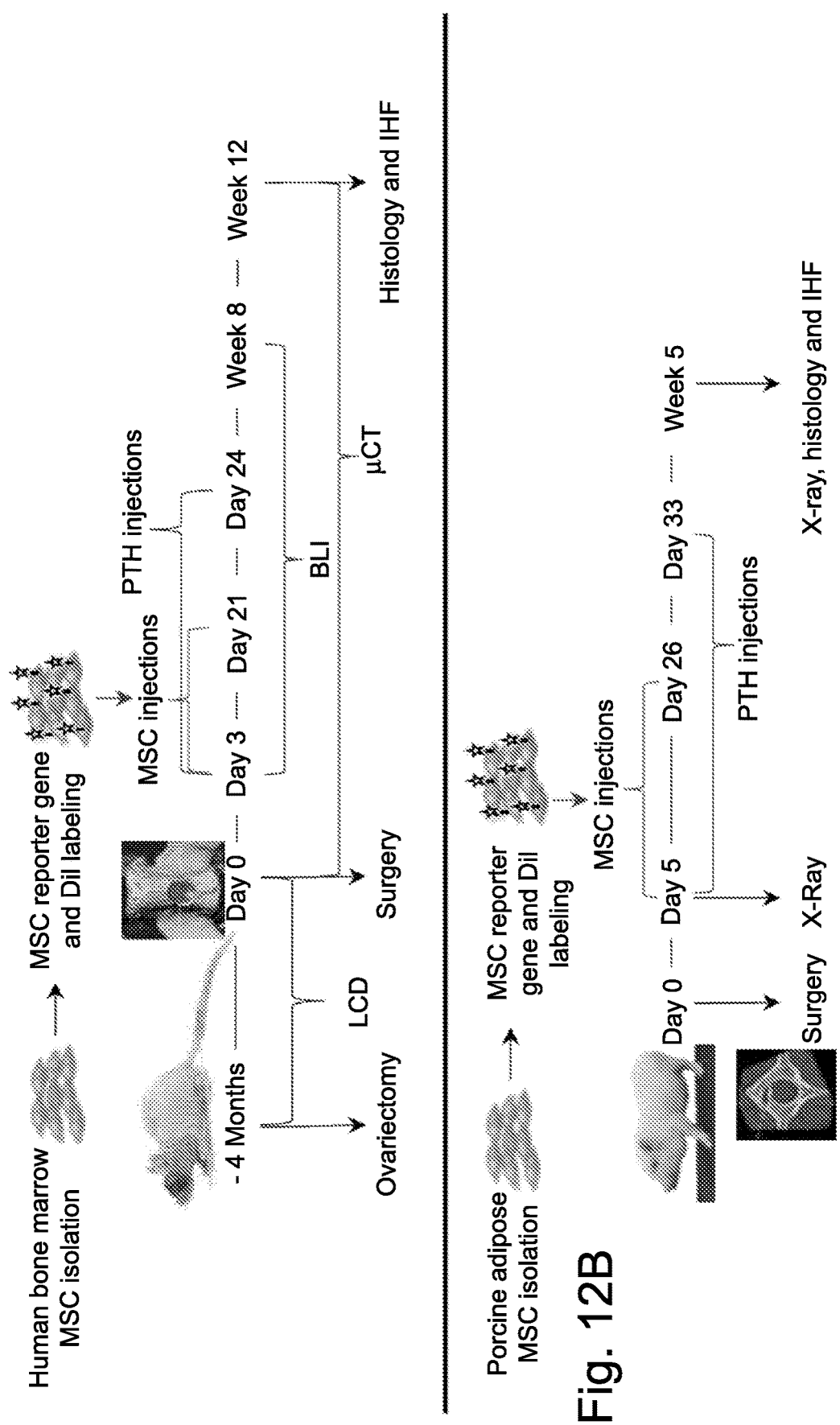

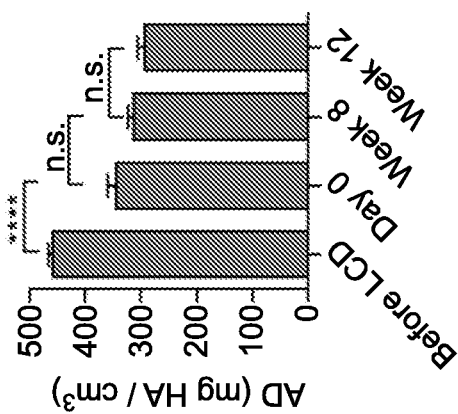
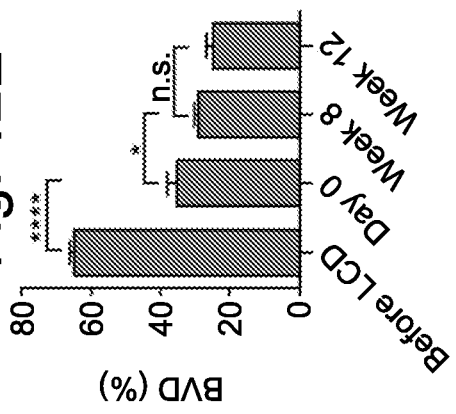
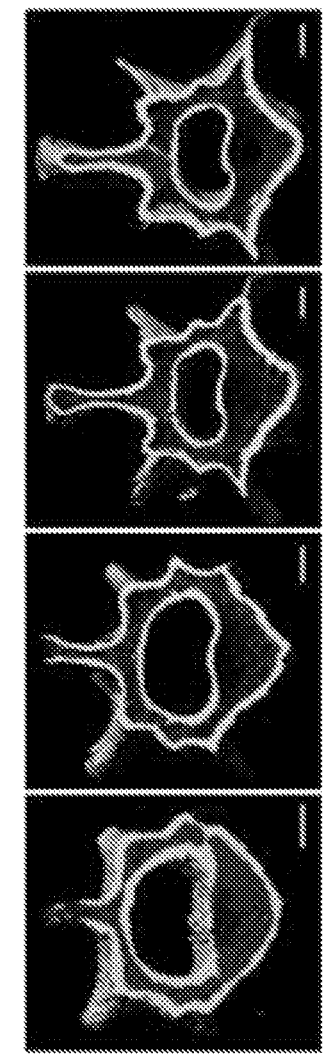
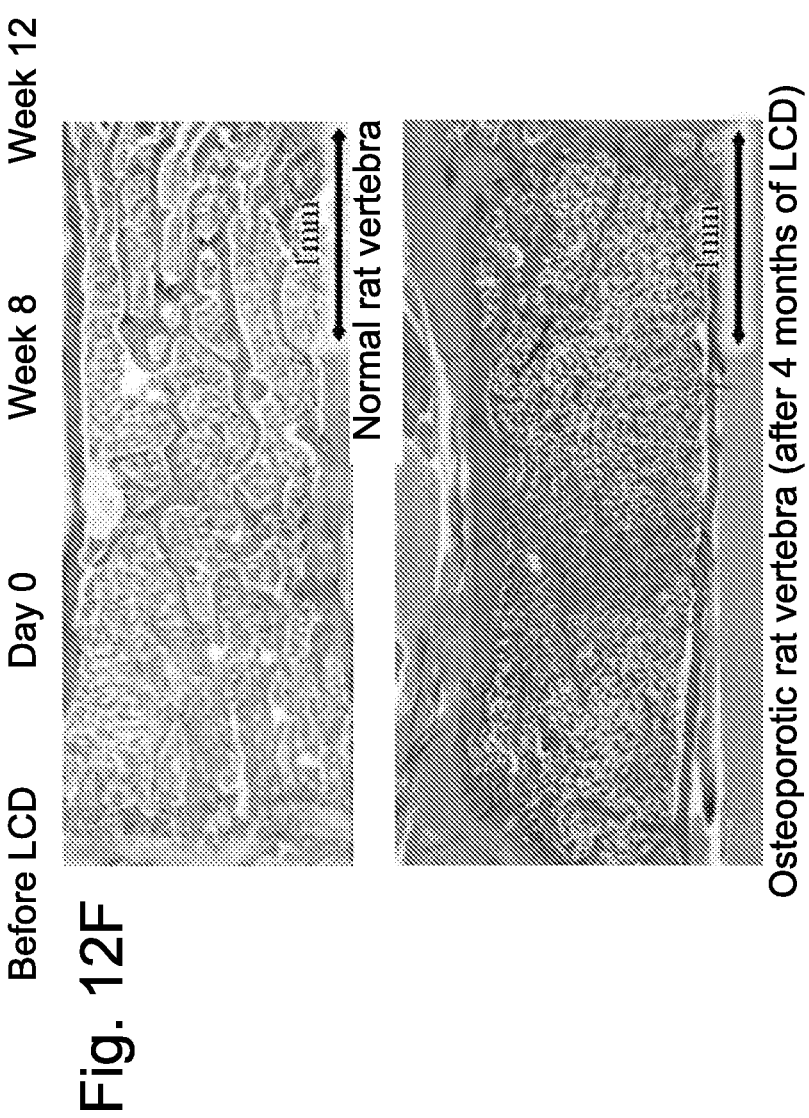

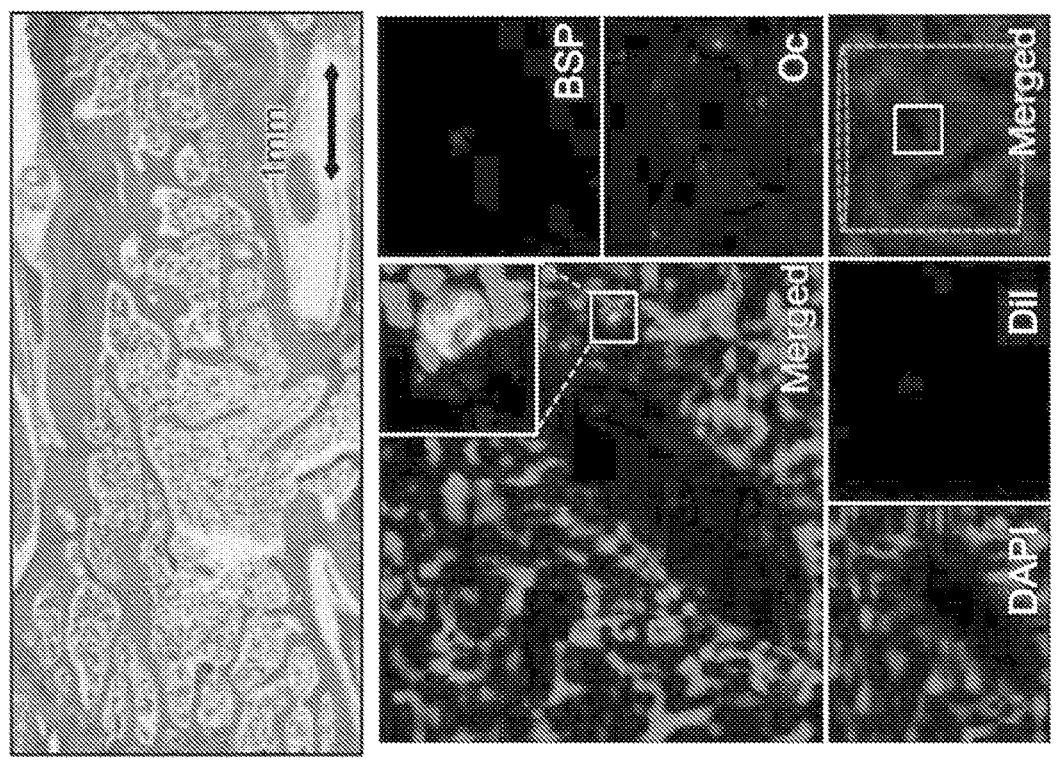
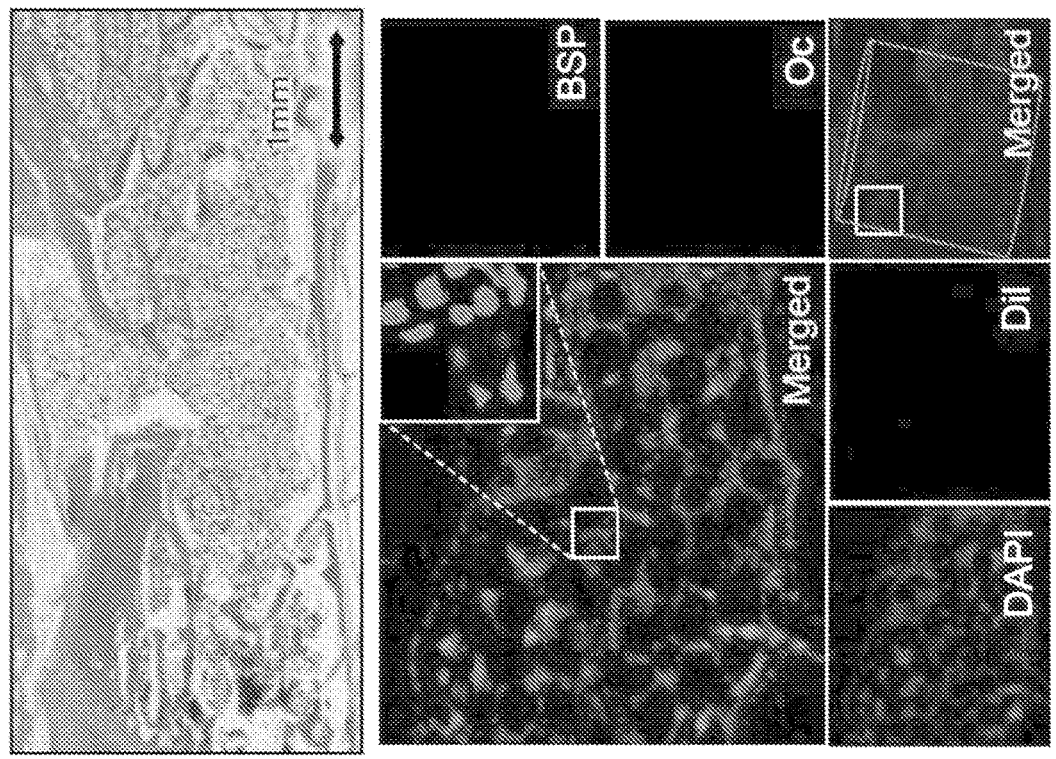
Fig. 22A
Fig. 22B

Fig. 23C
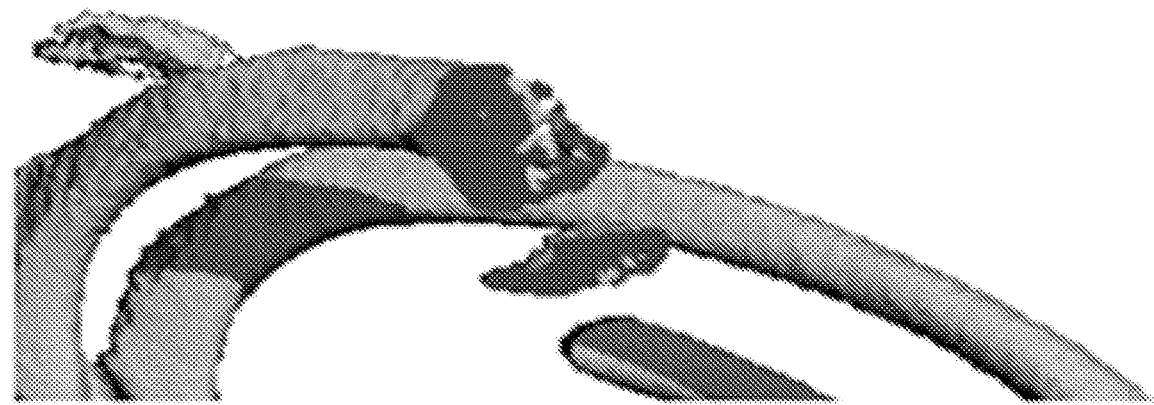
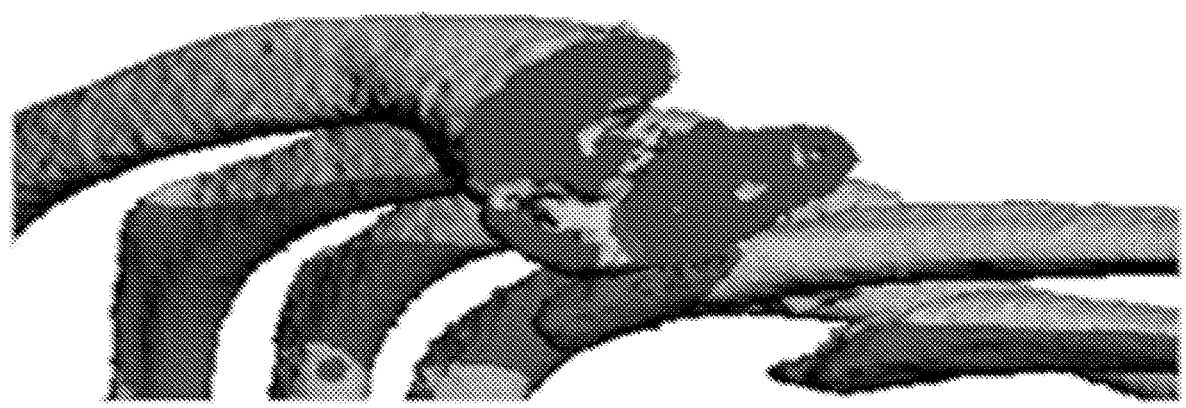

Fig. 24A
Fig. 24B
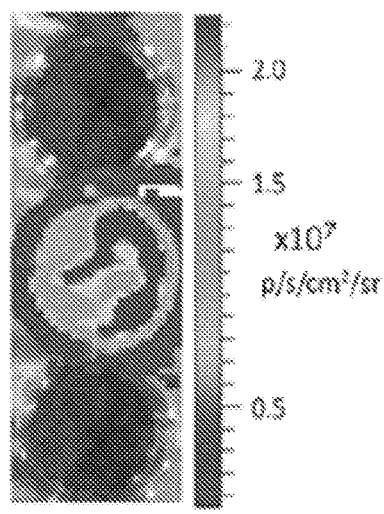
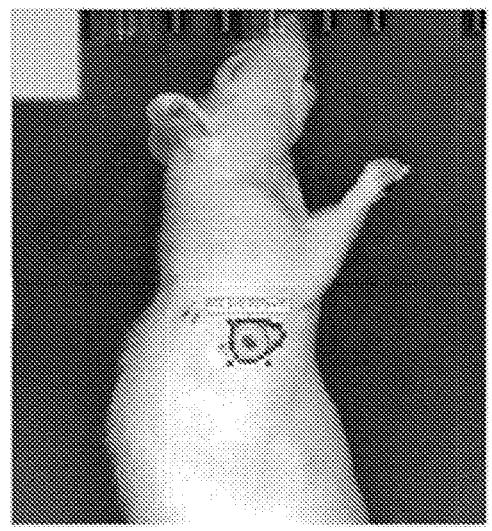
Negative control
Cells+PTH
Fig. 24C
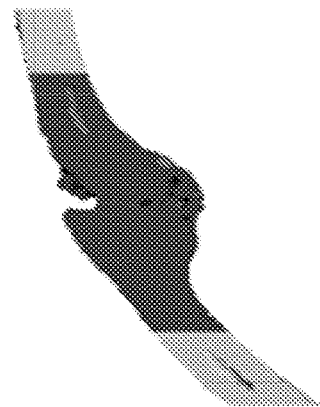

METHOD FOR NON SURGICAL REPAIR OF VERTEBRAL COMPRESSION FRACTURES

CROSS-REFERENCE TO RELATED APPLICATIONS

This application is a National Phase of International Application No. PCT/US2015/034275 filed Jun. 4, 2015, which designated the U.S. and that International Application was published under PCT Article 21(2) in English, which also includes a claim of priority under 35 U.S.C. § 119(e) to U.S. provisional patent application No. 62/007,793 filed Jun. 4, 2014 and U.S. provisional patent application No. 62/129,720 filed Mar. 6, 2015, the entirety of which is hereby incorporated by reference.

STATEMENT REGARDING FEDERALLY SPONSORED RESEARCH OR DEVELOPMENT

This invention was made with government support under Grant No. DE019902 awarded by the National Institutes of Health. The government has certain rights in the invention.

FIELD OF THE INVENTION

Described are methods and compositions for bone fractures, and related conditions. Administration of parathyroid hormone and mesenchymal stem cells improves therapies related to bone repair.

BACKGROUND

Approximately 10 million people in the United States are diagnosed as osteoporotic, while an additional 34 million are classified as having low bone mass. Osteoporosis-related vertebral compression fractures (OVCFs) are the most common fragility fractures in the United States, accounting for approximately 700,000 injuries per year—twice the rate of hip fractures. Approximately 70,000 VCFs result in hospitalization each year with an average hospital stay per patient of 8 days. Hence, fragility fractures due to osteoporosis consume enormous amounts of health care resources and present significant health risks for osteoporotic patients. Treatment of osteoporotic patients is mostly focused on prevention of OVCFs, mainly by using relatively new medicines such as Alendronate and parathyroid hormone (PTH). However, there are few treatment options available when OVCFs actually occur. Surgery involves significant risk of morbidity and implant failure in the osteoporotic patient population, and nonsurgical management such as medications and bracing are usually recommended for the vast majority of patients. Nevertheless, large numbers of patients report intractable pain and inability to return to activities. These limitations have fostered development of new, minimally invasive surgical techniques, including the procedures of vertebroplasty and balloon tamp reduction via percutaneous injection of polymethylmethacrylate (PMMA) into the collapsed spinal vertebral body. Significant drawbacks still appear to exist in that the synthetic nonbiological material remains a permanent foreign-body fixture in the spine, and some studies have reported that treatment with PMMA vertebroplasty is no more effective than sham treatment. Thus, there is a great need in the art for an effective biological solution for the treatment of OVCFs.

Described herein are improved therapeutics methods relying on combination therapies of PTH and mesenchymal stem cells (MSCs). Based on discoveries indicating that PTH administration can lead to increased homing of MSCs to sites of vertebral bone fracture, the described methods and compositions provide therapeutic approaches that rely, in-part, on stem cell capacity for regeneration and repair. Based on PTH activity promoting terminal differentiation of MSCs into osteoblasts, the potential for enhanced bone formation and fracture repair may allow for both preventative and palliative treatments in osteoporotic patients, with combined PTH+MSC therapy producing bone regeneration capacity that is significantly superior to either treatment alone. Systemic administration of mesenchymal stem cells and parathyroid hormone therapy display a synergistic effect in accelerating bone repair in small osteoporotic and large non-osteoporotic animals.

BRIEF DESCRIPTION OF FIGURES

FIG. 2(A) to FIG. 2(C). Differentiation multipotential of hBM-MSCs. The hBM-MSCs were differentiated in vitro to adipogenic (A) and osteogenic (B-C) lineages. Following adipogenic induction the cells were stained with Oil Red 0 and the staining was quantified using optical density (A). Following osteogenic induction the differentiation was evaluated using ALP colorimetric assay (B) and osteogenic genes expression (C). OPN=osteopontin, ALP=alkaline phosphatase, CoII=collagen type I, OC=osteocalcin FIG. 3(A) to FIG. 3(B). Role of MSCs in bone repair. (A) Earlier studies have shown that administration MSCs, including further combination with osteogenic factors, can lead to dramatic improvements in bone density and texture. In vivo bone formation using hBM-MSCs overexpressing BMP6. hBM-MSCs can be nucleofected with hBMP6 and $2.5 \times 10^6$ cells were injected intramuscularly into NOD/SCID mice. The bone formation was evaluated using μCT 2 and 4 weeks post injection. (B) General experimental design for further study including MSCs and parathyroid hormone (PTH).

FIG. 12(A) to FIG. 12(F). Experimental design and model establishment. Human bone-marrow MSCs were isolated, labeled to express the reporter gene Luc, and stained with DiI (A). Multiple vertebral defects were created in ovariectomized athymic rats after 4 months of LCD. These rats were daily administered PTH or PBS and given five IV injections of hMSCs or saline. Cell homing to vertebral defects was tracked using BLI, and bone regeneration was analyzed using μCT. 12 weeks postop the vertebrae were harvested for histology and immunofluorescence. Multiple lumbar vertebral defects were created in minipigs (B). The minipigs were administered PTH or vehicle and given four IV injections of pMSCs or saline. Bone regeneration was monitored using x-ray fluoroscopy and μCT. 5 weeks postop the vertebrae were harvested for histology and immunofluorescence. Ovariectomy and LCD induces significant and irreversible bone loss in athymic rats (C-E). Quantitative μCT analysis demonstrates reduced bone volume density and apparent density in intact lumbar vertebrae following a 4-month LCD and no further bone loss after the rats returned to a regular diet (D, E) (n=10). H&E-stained histological sections of rat vertebrae demonstrate a significant reduction in trabecular bone in the osteoporotic model (F).

FIG. 22(A) to FIG. 22(D). MSCs-hdPTH therapy regenerates vertebral defects in osteoporotic rats: histological and immunofluorescence analysis. Injured vertebrae were harvested, decalcified, embedded in paraffin, sectioned, and stained with standard H&E (A). Slides containing tissue stained against the osteogenic markers osteocalcin (Oc) and bone sialoprotein (BSP) showed that the markers were partially colocalized with DAPI-stained nuclei and DiI fluorescent dye, with which the MSCs had been labeled prior to their systemic administration (B). Slides containing tissue stained against the homing markers of both SDF1/CXCR4 (C) and Amp/EGFR (D) pathways also showed that those markers were partially colocalized with DAPI-stained nuclei and DiI fluorescent dye, with which the hMSCs had been labeled prior to their systemic administration.

FIG. 23(A) to FIG. 23(C). Rib Fracture Model: The rat is intubated to create positive breathing pressure and the rib cage is exposed. Two adjacent ribs are fractured approximately 1 cm from the spine (A). In-vivo uCT was performed 2 weeks after surgery, and 3D reconstruction was generated shown here from the lateral aspect (B). 3D reconstruction of the defect site showed no bridging (C).

FIG. 24(A) to FIG. 24(C). Rib regeneration by Cell and PTH administration:Human bone-marrow cells were isolated and transfected with Luciferase gene using lentiviral vector and luciferase expression was verified in vitro (A). The cells were administrated systemically via tail vein, and PTH therapy was given. One week after surgery, a localized bioluminescent signal was observed at the fracture site (B). MicroCT imaging shows bone bridging in rats treated with hMSCs and PTH compared to control (C).

SUMMARY OF THE INVENTION

Figure 1:
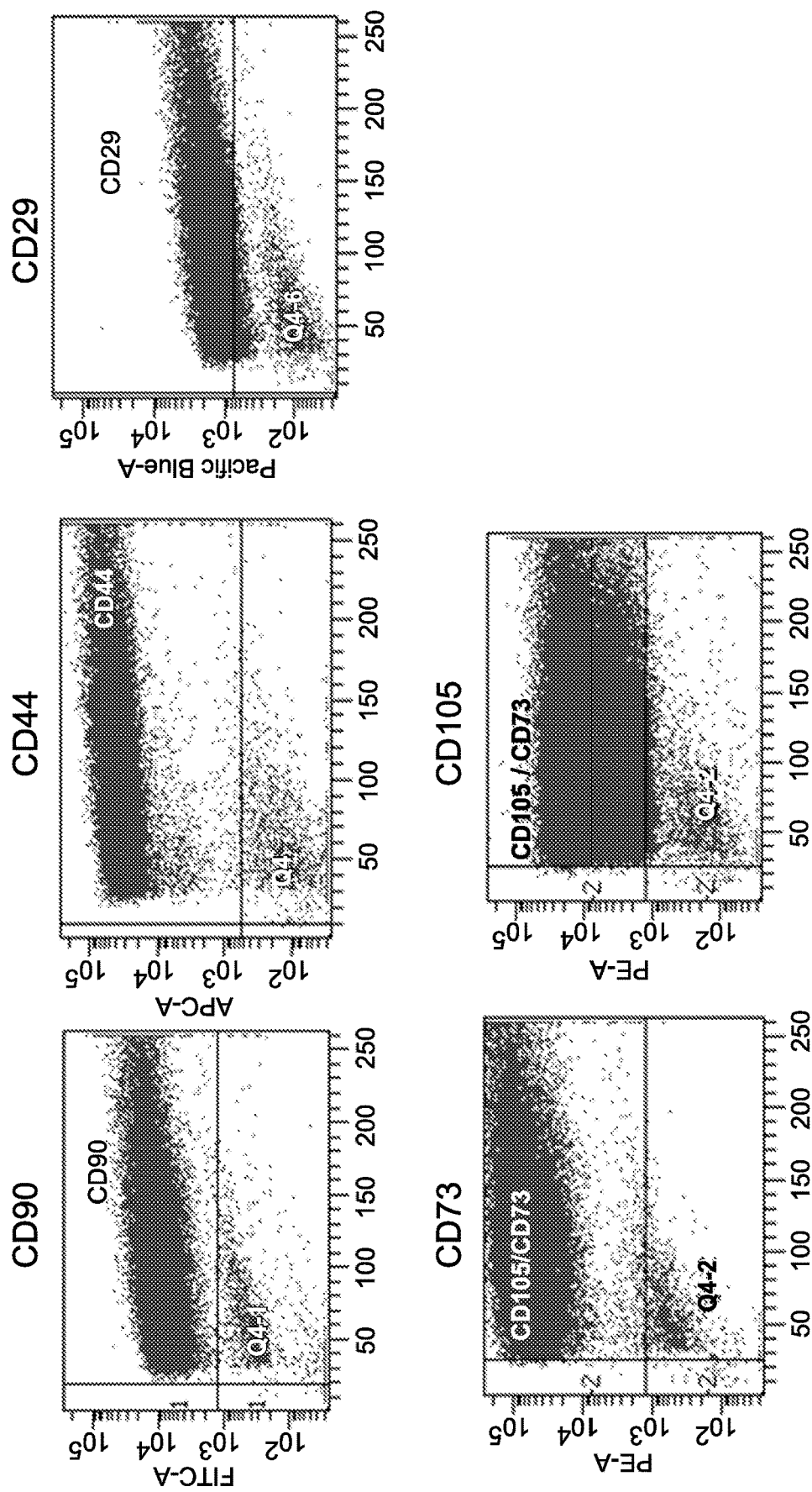
FIG. 1. Surface MSC marker expression by human (hBM-MSCs), evaluated using flow cytometry. Over 95% of the cells express acknowledged MSC surface markers indicating their MSC phenotype: CD90+, CD44+, CD29+, CD73+, and CD105+.

Described herein is a method for modulating bone texture, including selecting a subject and administering a quantity of mesenchymal stem cells (MSCs) and a quantity of parathyroid hormone (PTH), wherein administration of both MSCs and PTH modulates bone texture in the subject. In other embodiments, administration of MSCs and PTH is simultaneous. In other embodiments, the method includes further administration of PTH. In other embodiments, the administration of MSCs and PTH is sequential. In other embodiments, the administration of MSCs includes intravenous injection into the subject. In other embodiments, the administration of PTH includes subcutaneous injection into the subject. In other embodiments, the quantity of MSCs includes at least $1 \times 10^6$, $2 \times 10^6$, $3 \times 10^6$, $4 \times 10^6$ or $5 \times 10^6$ cells. In other embodiments, quantity of PTH includes 0.1 to 1, 1-10, 10-20, 20-30, 30-40, or at least 40 ug/kg. In other embodiments, modulating bone texture includes a change in trabecular thickness and/or bone density. In other embodiments, the change in trabecular thickness and/or bone density is in spinal vertebrae. In other embodiments, the spinal vertebrae are lumbar spinal vertebrae. In other embodiments, modulating bone texture includes a change in trabecular thickness and/or bone density in one or more ribs. In other embodiments, the MSCs express a heterologous protein. In other embodiments, heterologous protein includes bone morphogenic proteins (BMPs). In other embodiments, the BMPs comprise BMP-2, BMP-6, or both.

Further described herein is a method for increasing mesenchymal stem cell homing, including selecting a subject and administering a quantity of mesenchymal stem cells (MSCs) and a quantity of parathyroid hormone (PTH), wherein administration of both MSCs and PTH increases MSC homing in the subject. In other embodiments, MSC homing occurs in spinal vertebrae. In other embodiments, the spinal vertebrae are lumbar spinal vertebrae. In other embodiments, MSC homing occurs in one or more ribs. In other embodiments, administration of a quantity of MSCs includes intravenous injection of at least $1 \times 10^6$ cells into the subject, and administration of a quantity of PTH includes subcutaneous injection at least 0.1 ug/kg of PTH injection into the subject. In other embodiments, further daily administration of at least 0.1 ug/kg of PTH for at least 1 week, 2 weeks, or 3 weeks. In other embodiments, the MSCs express a heterologous protein. In other embodiments, the heterologous protein includes bone morphogenic proteins (BMPs). In other embodiments, the BMPs comprise BMP-2, BMP-6, or both. In other embodiments, the MSCs are human and are derived from bone marrow or adipose tissue. In other embodiments, the MSCs express one or more of CD90+, CD44+, CD29+, CD73+, and CD105+. In other embodiments, the MSCs express CXCR4+.

Also described herein is a method of treating osteoporotic related conditions, including selecting a human subject, administering a quantity of at least $1 \times 10^6$ human mesenchymal stem cells (MSCs) and a quantity of at least 0.1 ug/kg of parathyroid hormone (PTH) and further daily administration of at least 0.1 ug/kg of PTH for at least 1 week, wherein administration of human MSCs includes intravenous injection, administration of PTH includes subcutaneous injection, wherein administration of both MSCs and PTH treated the osteoporotic related condition. In other embodiments, the quantity of PTH includes 1-5 ug/kg. In other embodiments, the MSCs are derived from bone marrow or adipose tissue and express CD90+, CD44+, CD29+, CD73+, and CD105+. In other embodiments, the osteoporotic related condition includes vertebral compression fractures.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs.

Allen et al., *Remington: The Science and Practice of Pharmacy* 22nd ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3rd ed., revised ed., J. Wiley & Sons (New York, N.Y. 2006); Smith, *March's Advanced Organic Chemistry Reactions, Mechanisms and Structure* 7th ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2nd ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 March 24, 332(6162):323-7.

Osteoporosis affects more than 200 million people worldwide. Its pathogenesis stems from an improper balance between bone formation and bone resorption, resulting in low bone mass, impaired bone architecture, and increased risk of fractures. Current osteoporosis treatments consist predominantly of drugs that inhibit bone resorption without restoring lost bone mass.

Osteoporosis often remains asymptomatic until a fracture occurs. The most common fragility fractures are osteoporosis-related vertebral compression fractures (OVCFs) (>750,000 fractures/year in the US), which are associated with significantly high morbidity and mortality rates. As many as 150,000 OVCFs require hospitalization, which usually involves prolonged bed rest and intravenous (IV) administration of analgesic agents, which may worsen the underlying osteoporosis. Surgery is not an option for patients with osteoporosis due to the low density of their vertebral bones. Minimally invasive surgical techniques, such as vertebroplasty, reportedly are no more effective than sham surgery. Therefore, there is a clear medical need for the development of new, noninvasive therapies to treat OVCFs.

Osteoporosis-related vertebral compression fractures occur twice as often as hip fractures, but few treatment options are available. Recombinant parathyroid hormone accelerates fracture repair in healthy animals by activating mesenchymal stem cells (MSCs); however, it would prove less effective in patients with osteoporosis, in whom MSCs are fewer and/or dysfunctional.

Additionally, 25% of all trauma deaths in the United States are the result of trauma to the chest. Rib fractures (RFs) occur in more than two thirds of these patients. In elderly patients these fractures were associated with high morbidity and mortality rates, which may reach up to 20%. Unfortunately, current treatment of RFs is limited to pain control, which often does not prevent functional disabilities for many months and even death. To date there is no good medical solution to treat multiple RFs.

The Inventors hypothesized that intravenous injection of MSCs combined with PTH therapy would induce MSC recruitment to injury sites, leading to enhanced osteogenesis and eventual defect repair. To test this hypothesis, the Inventors created vertebral bone defects in osteoporotic rats and treated them with intravenous injections of human MSCs and intermittent administration of rPTH. The vertebral defects were rapidly and efficiently repaired when animals received this combined MSCs-PTH treatment, compared to animals that received either treatment alone or no treatment. The Inventors found that rPTH significantly enhanced cell homing to the lumbar region, where the MSCs differentiated into bone-forming cells. Interestingly, a novel combined approach to treat RFs, composed of systemic intravenous administration of MSCs and PTH therapy using a rat model of multiple rib fractures further and observed cell homing to rib fracture sites, with fracture repair in rats treated with hMSCs and PTH compared to untreated rats. Finally, the Inventors observed remarkable bone regeneration when minipigs with multiple vertebral bone defects were treated with combined MSCs-rPTH therapy.

Bone tissue is a specialized form of connective tissue that possesses a natural regenerative capacity. Nevertheless, 5-10% of all fractures and as many as 30% of patients with pre-existing conditions face impaired healing and significant morbidity, which in turn can also be economically burdensome. Surgery involves significant risk of morbidity and implant failure in the osteoporotic patient population, and therefore nonsurgical management such as medications and bracing are usually recommended for the vast majority of patients. Unfortunately, large numbers of patients report intractable pain and inability to return to activities. These limitations have fostered increasing interest in new, minimally invasive surgical techniques.

Fracture biomechanics are primarily determined by disruption of the trabecular microarchitecture and ongoing symptoms may be related to ineffective structural repair and motion. New non-biological methods have been developed to regain the biomechanical properties of the vertebral body. These include the minimally invasive procedures of vertebroplasty and balloon tamp reduction via percutaneous injection of polymethylmethacrylate (PMMA) into the collapsed spinal vertebral body. Recent studies suggest that prophylactic injection of PMMA into osteoporotic spinal vertebrae preserves the stiffness of the vertebrae better than post fracture injection, but a significant drawback appears to exist in that the synthetic nonbiological material does not resorb and remains a permanent foreign-body fixture in the spine. For example, some studies have reported that treatment with PMMA vertebroplasty was no more effective than sham treatment. In view of these limitations of surgical and non-biological techniques, development of biological methods for treating osteoporotic patients remains an important goal.

To date, autologous bone grafting remains the 'gold standard' biological method used to promote nonunion fracture sites and spinal fusion in cases of intervertebral disc degeneration. However, failure rates as high as 30% have been cited together with complications resulting from repeated interventions. A compelling alternative is use of mesenchymal stem cells (MSCs). MSCs have been isolated from various adult tissues, among which are bone marrow (BM) and adipose tissue, these cells can differentiate successfully into osteogenic, chondrogenic and adipogenic lineages. The capacity of MSCs to differentiate to bone cells presents a promising avenue as a therapeutic material compensating for bone loss. Indeed, it has been shown that direct implantation of MSCs induces rapid bone regeneration and fracture repair in vivo in several models of bone loss and at several distinct bone sites (e.g., the long bones, calvaria, and spine). Compelling evidence also indicates that although they may be trapped in the lungs, systemically administered MSCs preferentially migrate to sites of injury in different experimental models. In addition, when genetically modified to incorporate factors such as bone morphogenic proteins (BMPs), these multipotent cells have displayed the ability to form and regenerate bone in vivo in multiple animal models, providing gene- and cell-mediated therapy for clinical orthopedic applications. The role of osteoinductive factors in promoting optimal bone regeneration via MSCs suggests incorporation of materials such as hydroxyapatite scaffolds, or osteogenics protein such as BMPs and/or parathyroid hormone (PTH), as potentially potent combinations for treating osteoporotic patients.

Mesenchymal stem cells (MSCs) can differentiate into osteoblasts, chondrocytes, and adipocytes. Systemically administered MSCs migrate preferentially to injury sites in various disease models. Although the exact mechanism for this activity is not fully understood, it is likely that the injured tissue secretes specific ligands that facilitate homing, adhesion, and infiltration of MSCs, similar to the mechanism seen in recruitment of leukocytes to sites of inflammation. MSCs can be reintroduced into the donor as an autologous graft or used as allogeneic cells to treat other recipients. Unfortunately, autologous MSCs may not be a suitable treatment for OVCFs, because patients with osteoporosis have fewer MSCs or MSCs that are less prone to proliferate and differentiate into osteoblasts and consequently form bone. Since allogeneic MSCs do not require a cell isolation phase for each patient and are believed to be immunomodulatory, their use is considered advantageous for the clinical setting. Indeed, allogeneic MSCs are being evaluated in many clinical trials as a systemic therapy for various diseases.

To achieve efficient tissue regeneration following systemic administration of stem cells, a sufficient supply of cells must home to the injury site and subsequently differentiate in situ. The 1-34 portion of PTH, an FDA-approved bone anabolic agent, increased endogenous MSC migration to injury sites, promoted osteoblast progenitor proliferation and differentiation, and decreased osteoblast apoptosis. However, the PTH dosages used in the preclinical studies that provided these results were extremely high: approximately 140 times the dosage used clinically and in this study.

Human parathyroid hormone (hPTH) is an 84-amino acid peptide hormone that plays a key role in the maintenance of calcium homeostasis. hPTH binds to a target cell surface G-protein-coupled hPTH/hPTHrP receptor, which results in activation of adenylate cyclase and phospholipases and increased intracellular levels of cyclic AMP and calcium. Intermittent hPTH given by subcutaneous injection has been shown to exert potent anabolic effects on the skeleton, and two forms of recombinant hPTH have been evaluated in clinical trials, hPTH(1-34, also known as teriparatide) and the intact 84-amino acid form, hPTH(1-84). Teriparatide has been FDA approved for use as an anabolic agent in the treatment of severe osteoporosis. Based on its remarkable efficacy in reducing fractures in these patients, there is now great interest in using teriparatide to treat fracture non-unions. hPTH(1-84) includes a C terminus, which may have discrete biologic properties and may therefore have different biologic actions from hPTH(1-34). In various preclinical studies, PTH has been demonstrated as improving fracture callus quality, increasing bone mineral content and density, and accelerating endochondral ossification in comparison with controls. Similar other reported benefits have included accelerated healing, enhanced bone mineral content and increased bone cross sectional area in rabbit tibia metaphyseal osteotomy model.

Underlying these therapeutic benefits, it appears hPTH increases the rate of bone remodelling and results in a positive remodelling balance, leading to thicker osteons (structural units of remodelled bone). New bone formation occurs on quiescent surfaces and, as a result, trabecular architecture comes to more closely resemble normal bone. hPTH(1-34) induces new periosteal bone apposition, which results in the enlargement of the outer circumference of tubular bones such as the radius. This bone apposition results from decreased osteoblast apoptosis and enhanced differentiation of osteoblasts from preosteoblasts. By contrast, alternative therapeutic compositions such as bisphosphonates preserve existing skeletal microarchitecture, but do not restore it toward a more normal structure. Instead, increases in bone mass with bisphosphonates are most likely due to enhanced secondary mineralization of preformed osteons.

Importantly, studies demonstrate that PTH stimulates mesenchymal stem cell (MSC) recruitment to bone by inducing CXCL12/SDF1 expression in osteoblasts. During the course of organ regeneration, however, it has been demonstrated that both local MSCs derived from the injured tissue and circulating MSCs collaborate in the healing of damaged organs. In this capacity, the binding of SDF-1 to CXCR4, leads to adherence of stem cells through increased expression of adhesion molecules on the cell membrane surface, and local and circulating stem cells are recruited to sites of tissue in need of repair and regeneration through homing and extravasation. As cells at the site of bone tissue injury may secrete SDF-1 ligand via osteoblasts, this attracts MSCs expressing receptor CXCR4 to the injury site wherein subsequent interaction of SDF-1 and CXCR4 that promotes adhesion, migration and homing to the sites of tissue injury damage and possibly, tissue-specific differentiation via chemoattractant SDF1. Thus, PTH presents a promising mechanism to promote MSC migration to the site of bone injury, particularly in view of the decreased numbers of MSCs, dysfunctional MSCs, or both, that is observed in osteoporotic patients. For example, combination therapies relying on intravenous (IV) injection of MSCs combined with a PTH regimen could present a particularly effective therapy for the treatment of multiple fractures in these patients, further satisfying the need for minimally invasive techniques.

Described herein are the therapeutic results of combining systemic injection of exogenous MSCs and daily intermittent administration of PTH to enhance MSC homing to bone fractures, including rib and vertebral fractures, including osteogenic differentiation and eventual fracture repair in osteoporotic animals. As shown, combined MSCs-PTH therapy yields a synergistic effect on bone regeneration that would be superior to either treatment alone. It is shown that PTH has a significant effect on homing of MSCs to bone defects, possibly via multiple pathways in addition to PTH's well-established osteo-anabolic effect. Importantly, based on results described herein PTH can play an adjuvant role in stem cell therapy, based on a minimal dosage for a minimal period of time required to support the homing and differentiation of multiple systemic cell injections. hMSCs are shown as capable of homing to the defect site in a dose-dependent manner in response to PTH administration, but a therapeutic effect for inducing significantly higher homing of MSCs can be achieved when applying a lower dosage. Moreover, such an approach finds wide extensibility across different types of fractures, such as rib and vertebral fractures.

Described herein is a method for modulating bone texture, including selecting a subject and administering a quantity of mesenchymal stem cells (MSCs) and a quantity of parathyroid hormone (PTH), wherein administration of both MSCs and PTH modulates bone texture in the subject. In other embodiments, the administration of MSCs and PTH is simultaneous. In various embodiments, it is understood that MSCs are multipotent stromal cells that can differentiate into a variety of cell types, including osteoblasts (bone cells), chondrocytes (cartilage cells), and adipocytes (fat cells). In other embodiments, the method includes further administration of PTH. This can include for example, administration of PTH for at least 1 week, 2, 3 4, 5, 6, 7, 8, 9, 10 or more weeks. In other embodiments, the administration of MSCs and PTH is sequential. In other embodiments, the administration of MSCs includes intravenous injection into the subject. In other embodiments, the administration of PTH includes subcutaneous injection into the subject. In other embodiments, the quantity of MSCs includes at least $1\times10^6$, $2\times10^6$, $3\times10^6$, $4\times10^6$ or $5\times10^6$ cells. In other embodiments, the quantity of MSCs includes at least $6\times10^6$, $7\times10^6$, $8\times10^6$, $9\times10^6$ or $10^7$ or more cells. In other embodiments, the quantity of PTH include 0.1 to 1, 1-10, 10-20, 20-30, 30-40, or at least 40 ug/kg. This includes, for example, 0.1-1 µg/kg, 1-1.75 µg/kg, 1.75-3 µg/kg and 3-5 µg/kg. In other embodiments, the quantity of PTH include 0.1 to 1, 2, 3, 4, 5, 6, 7, 8, 9, 10, 10-20, 20-30, 30-40, 40-50, 60-70, 70-80, 80-90, 90-100, 100 or more ug/kg. For example, this can include administering a quantity of at least $1\times10^6$ human mesenchymal stem cells (MSCs) and a quantity of at least 0.1 ug/kg. of parathyroid hormone (PTH), and further daily administration of at least 0.1 ug/kg.of PTH for at least 1 week, wherein administration of human MSCs includes intravenous injection, and administration of PTH includes subcutaneous injection. In other embodiments, the method includes further administration of PTH. This can include for example, administration of PTH for at least 1 week, 2, 3 4, 5, 6, 7, 8, 9, 10 or more weeks. In other embodiments, modulating bone texture includes a change in trabecular thickness and/or bone density. In other embodiments, the change in trabecular thickness and/or bone density is in spinal vertebrae. In other embodiments, the spinal vertebrae are thoracic, cervical or lumbar spinal vertebrae. In other embodiments, the spinal vertebrae are lumbar spinal vertebrae. In other embodiments, modulating bone texture occurs in ribs, including for example, rib fractures. In other embodiments, the MSCs express a heterologous protein. In various embodiments, the heterologous protein is introduced by any number of techniques known in the art, such as viral infection, transfection or nucleofection. In other embodiments, the heterologous protein include bone morphogenic proteins (BMPs). In other embodiments, the BMPs include BMP-2, BMP-6, or both. In other embodiments, the MSCs are human and are derived from bone marrow or adipose tissue. In other embodiments, the MSCs express one or more of CD90+, CD44+, CD29+, CD73+, and CD105+. In other embodiments, the MSCs express CXCR4+. In other embodiments, the MSCs may lack expression of one or more of CD11b, CD14, CD19, CD34, CD45, CD79a and HLA-DR In other embodiments, the PTH is an active fragment of full-length endogenous PTH, for example, PTH1-34 (the first 34 amino acids of PTH, also known as teriparatride)

Also described herein is a method for increasing mesenchymal stem cell homing, including selecting a subject and administering a quantity of mesenchymal stem cells (MSCs) and a quantity of parathyroid hormone (PTH), wherein administration of both MSCs and PTH increases MSC homing in the subject. In other embodiments, the MSC homing occurs in bone. In other embodiments, the MSC homing occurs in ribs, including for example, rib fractures. In other embodiments, the MSC homing occurs in spinal vertebrae. In other embodiments, the spinal vertebrae are thoracic, cervical or lumbar spinal vertebrae. In other embodiments, the spinal vertebrae are lumbar spinal vertebrae. In other embodiments, the administration of a quantity of MSCs includes intravenous injection of at least $1\times10^6$ cells into the subject, and administration of a quantity of PTH includes subcutaneous injection at least 0.1 ug/kg.of PTH injection into the subject. In other embodiments, the quantity of MSCs includes at least $1\times10^6$, $2\times10^6$, $3\times10^6$, $4\times10^6$ or $5\times10^6$ cells. In other embodiments, the quantity of MSCs includes at least $6\times10^6$, $7\times10^6$, $8\times10^6$, $9\times10^6$ or $10^7$ or more cells. In other embodiments, the quantity of PTH include 0.1 to 1, 1-10, 10-20, 20-30, 30-40, or at least 40 ug/kg. This includes, for example, 0.1-1 µg/kg, 1-1.75 µg/kg, 1.75-3 µg/kg and 3-5 µg/kg. In other embodiments, further daily In other embodiments, the quantity of PTH include 0.1 to 1, 2, 3, 4, 5, 6, 7, 8, 9, 10, 10-20, 20-30, 30-40, 40-50, 60-70, 70-80, 80-90, 90-100, 100 or more ug/kg. For example, this can include administering a quantity of at least $1\times10^6$ human mesenchymal stem cells (MSCs) and a quantity of at least 0.1 ug/kg.of parathyroid hormone (PTH), and further daily administration of at least 0.1 ug/kg.of PTH for at least 1 week, 2 weeks, or 3 weeks. In other embodiments, the method includes further administration of PTH. This can include for example, administration of PTH for at least 1 week, 2, 3 4, 5, 6, 7, 8, 9, 10 or more weeks. In other embodiments, the MSCs express a heterologous protein. In various embodiments, the heterologous protein is introduced by any number of techniques known in the art, such as viral infection, transfection or nucleofection. In other embodiments, the heterologous protein includes bone morphogenic proteins (BMPs). In other embodiments, the BMPs include BMP-2, BMP-6, or both. In other embodiments, the MSCs are human and are derived from bone marrow or adipose tissue. In other embodiments, the MSCs express one or more of CD90+, CD44+, CD29+, CD73+, and CD105+. In other embodiments, the MSCs express CXCR4+. In other embodiments, the MSCs may lack expression of one or more of CD11b, CD14, CD19, CD34, CD45, CD79a and HLA-DR For example, an increase in the number of CXCR4+ cells as a tissue site indicates an increase in MSC homing. In other embodiments, the PTH is an active fragment of full-length endogenous PTH, for example, PTH1-34 (the first 34 amino acids of PTH, also known as teriparatride)

Further described herein is a method of treating osteoporotic related conditions, including selecting a human subject, administering a quantity of at least $1\times10^6$ human mesenchymal stem cells (MSCs) and a quantity of at least 0.1 ug/kg.of parathyroid hormone (PTH), and further daily administration of at least 0.1 ug/kg.of PTH for at least 1 week, wherein administration of human MSCs includes intravenous injection, administration of PTH includes subcutaneous injection, wherein administration of both MSCs and PTH treated the osteoporotic related condition. In other embodiments, the quantity of MSCs includes at least $1\times10^6$, $2\times10^6$, $3\times10^6$, $4\times10^6$ or $5\times10^6$ cells. In other embodiments, the quantity of MSCs includes at least $6\times10^6$, $7\times10^6$, $8\times10^6$, $9\times10^6$ or $10^7$ or more cells. In other embodiments, the MSCs are derived from bone marrow or adipose tissue and express CD90+, CD44+, CD29+, CD73+, and CD105+. In other embodiments, the MSCs express CXCR4+. In other embodiments, the MSCs may lack expression of one or more of CD11b, CD14, CD19, CD34, CD45, CD79a and HLA-DR In other embodiments, the method includes further administration of PTH. This can include for example, administration of PTH for at least 1 week, 2, 3 4, 5, 6, 7, 8, 9, 10 or more weeks. In other embodiments, the quantity of PTH include 0.1 to 1, 1-10, 10-20, 20-30, 30-40, or at least 40 ug/kg. This includes, for example, 0.1-1 µg/kg, 1-1.75 µg/kg, 1.75-3 µg/kg and 3-5 µg/kg. In other embodiments, the quantity of PTH include 0.1 to 1, 2, 3, 4, 5, 6, 7, 8, 9, 10, 10-20, 20-30, 30-40, 40-50, 60-70, 70-80, 80-90, 90-100, 100 or more ug/kg. In other embodiments, the PTH is an active fragment of full-length endogenous PTH, for example, PTH1-34 (the first 34 amino acids of PTH, also known as teriparatride). In other embodiments, the osteoporotic related condition includes vertebral compression fractures. In other embodiments, the osteoporotic related condition includes hip fractures. In various embodiments, administering PTH is adjuvant to conventional therapy.

Further described herein is a method of treating bone fractures, including selecting a human subject, administering a quantity of at least $1 \times 10^6$ human mesenchymal stem cells (MSCs) and a quantity of at least 0.1 ug/kg.of parathyroid hormone (PTH), and further daily administration of at least 0.1 ug/kg.of PTH for at least 1 week, wherein administration of human MSCs includes intravenous injection, administration of PTH includes subcutaneous injection, wherein administration of both MSCs and PTH treats the bone fracture. In other embodiments, the quantity of MSCs includes at least $1 \times 10^6$, $2 \times 10^6$, $3 \times 10^6$, $4 \times 10^6$ or $5 \times 10^6$ cells. In other embodiments, the quantity of MSCs includes at least $6 \times 10^6$, $7 \times 10^6$, $8 \times 10^6$, $9 \times 10^6$ or $10^7$ or more cells. In other embodiments, the MSCs are derived from bone marrow or adipose tissue and express CD90+, CD44+, CD29+, CD73+, and CD105+. In other embodiments, the MSCs express CXCR4+. In other embodiments, the MSCs may lack expression of one or more of CD11b, CD14, CD19, CD34, CD45, CD79a and HLA-DR In other embodiments, the method includes further administration of PTH. This can include for example, administration of PTH for at least 1 week, 2, 3 4, 5, 6, 7, 8, 9, 10 or more weeks. In other embodiments, the quantity of PTH include 0.1 to 1, 1-10, 10-20, 20-30, 30-40, or at least 40 ug/kg. This includes, for example, 0.1-1 µg/kg, 1-1.75 µg/kg, 1.75-3 µg/kg and 3-5 µg/kg. In other embodiments, the quantity of PTH include 0.1 to 1, 2, 3, 4, 5, 6, 7, 8, 9, 10, 10-20, 20-30, 30-40, 40-50, 60-70, 70-80, 80-90, 90-100, 100 or more ug/kg. In other embodiments, the bone fracture include fractures of the ribs, hips, arms, legs or other bones susceptible to fracture. This includes, for example, 0.1-1 µg/kg, 1-1.75 µg/kg, 1.75-3 µg/kg and 3-5 µg/kg. In other embodiments, the quantity of PTH include 0.1 to 1, 2, 3, 4, 5, 6, 7, 8, 9, 10, 10-20, 20-30, 30-40, 40-50, 60-70, 70-80, 80-90, 90-100, 100 or more ug/kg. In other embodiments, the PTH is an active fragment of full-length endogenous PTH, for example, PTH1-34 (the first 34 amino acids of PTH, also known as teriparatride). In various embodiments, administering PTH is adjuvant to conventional therapy.

Example 1

Animal MSC Isolation and Culture

For animal studies, mesenchymal stem cells (MSCs) can be isolated from costal bone marrow (BM) and the subcutaneous adipose tissues of euthanized pigs (weighing 35-40 kg with an average age of 1.5 years). For example, adipose tissues and costal BM were harvested aseptically. The adipose tissues are cut into small pieces (5 mm 5 mm or less), washed with 1% BSA PBS (Invitrogen, Carlsbad, Calif., USA), and treated with 0.075% collagenase at 37° C. for 1 h. The BM-containing ribs are scraped, flushed with PBS, and centrifuged at 900 g for 10 min. The pellet can be resuspended in PBS, after which it is layered on lymphocyte separation medium (ICN Pharmaceuticals, Bryan, Ohio, USA) and centrifuged at 900 g for 30 min at 30° C. without a break.

For further culturing at the end of the isolation process, the isolated mononuclear cells from both tissues are plated in tissue-culture dishes at a density of $0.4 \times 10^6$ cells per cm$^2$ in 5% CO$_2$/95% air at 37° C. Culture medium can include high-glucose Dulbecco's modified Eagle's medium (Invitrogen) supplemented with 2 m$_{M\ L}$-glutamine, 100 U ml$^1$ penicillin/streptomycin (Invitrogen), and 10% fetal calf serum (Invitrogen). Such media may be after 72 h and thereafter every 3-4 days. After reaching confluence, cells are trypsinized using 0.25% trypsin-EDTA (Invitrogen) and replated at a density of $7 \times 10^4$ cells per cm$^2$ for expansion. Cells can be grown in culture up to the fifth passage and used for in vitro and in vivo differentiation studies.

Example 2

Human MSC Isolation and Culture

Human mesenchymal stem cells (hMSCs) can be isolated from explants of human bone marrow surgical waste and are capable of expansion in vitro. For example, 10 ml marrow aspirates are collected into a tube with 6000 U heparin, washed with PBS, and recovered cells are collected by centrifugation at 900 g. Collected cells are then loaded onto Percoll solution (density 1.073 g/ml). Cell separation is accomplished by centrifugation at 1100 g (30 min at 20 uC). Alternatively, cells can be isolated using plastic adherence protocol. Nucleated cells collected are washed twice with PBS and then cultured and subcultured in Dulbecco's minimal essential medium (DMEM) (low glucose) supplemented with 10% fetal calf serum (FCS). Various approaches for isolating and culturing MSCs are well-understood, including examples presented in Turgeman, G., et al., Engineered human mesenchymal stem cells: a novel platform for skeletal cell mediated gene therapy. *J Gene Med*, 2001. 3(3): p. 240-51, which is herein fully incorporated by reference.

For heterologous gene expression or labeling studies, hMSCs can be infected in vitro at 80% confluence with recombinant adenoviruses encoding rhBMP-2 (Ad-BMP-2) and LacZ (Ad-LacZ) at multiplicity of infection (MOI) of 100, 2 h in PBS after which the medium is added for 3 days. Efficiency of infection is estimated post-infection with Ad-LacZ using X-gal staining X-gal histochemical staining can be performed as follows: cells are fixed with 0.25% glutaraldehyde, 0.1 M NaPO$_4$ (pH 8.3), 5 mM ethylen glycol-bis (b-aminoethyl ether) (EGTA) and 2 mM MgCl$_2$ for 30 min. Cells are then washed three times (with 0.1 M NaPO$_4$, 2 mM MgCl$_2$, 0.1% deoxycholate, 0.2% Nonident P40) and stained with X-gal solution (1 mg/ml), 5 mM K$_3$Fe(CN)$_6$, 5 mM K$_4$Fe(CN)$_6$3H$_2$O, 0.1 M NaPO$_4$, 2 mM MgCl$_2$, 0.1% deoxycholate, 0.2% Nonident P40, in the dark at room temperature (RT) overnight.

For infecting hMSCs with both Ad-BMP-2 and Ad-LacZ, cells can be grown and infected in the same conditions described above with both adenoviral vectors at a MOI of 50 for each of the viral vectors.

Example 3

Human MSC Characterization and Differentiation

Human MSCs can be characterized according to various antigenic surface markers or other expression products. Bone marrow derived human MSCs display a panel of 5 MSC surface markers, including CD90+, CD44+, CD29+, CD73+, and CD105+, confirming their MSC phenotype (FIG. 1). Using the described isolation techniques, over 95% of isolated cells can be obtained which include this expression panel.

Figure 2C:
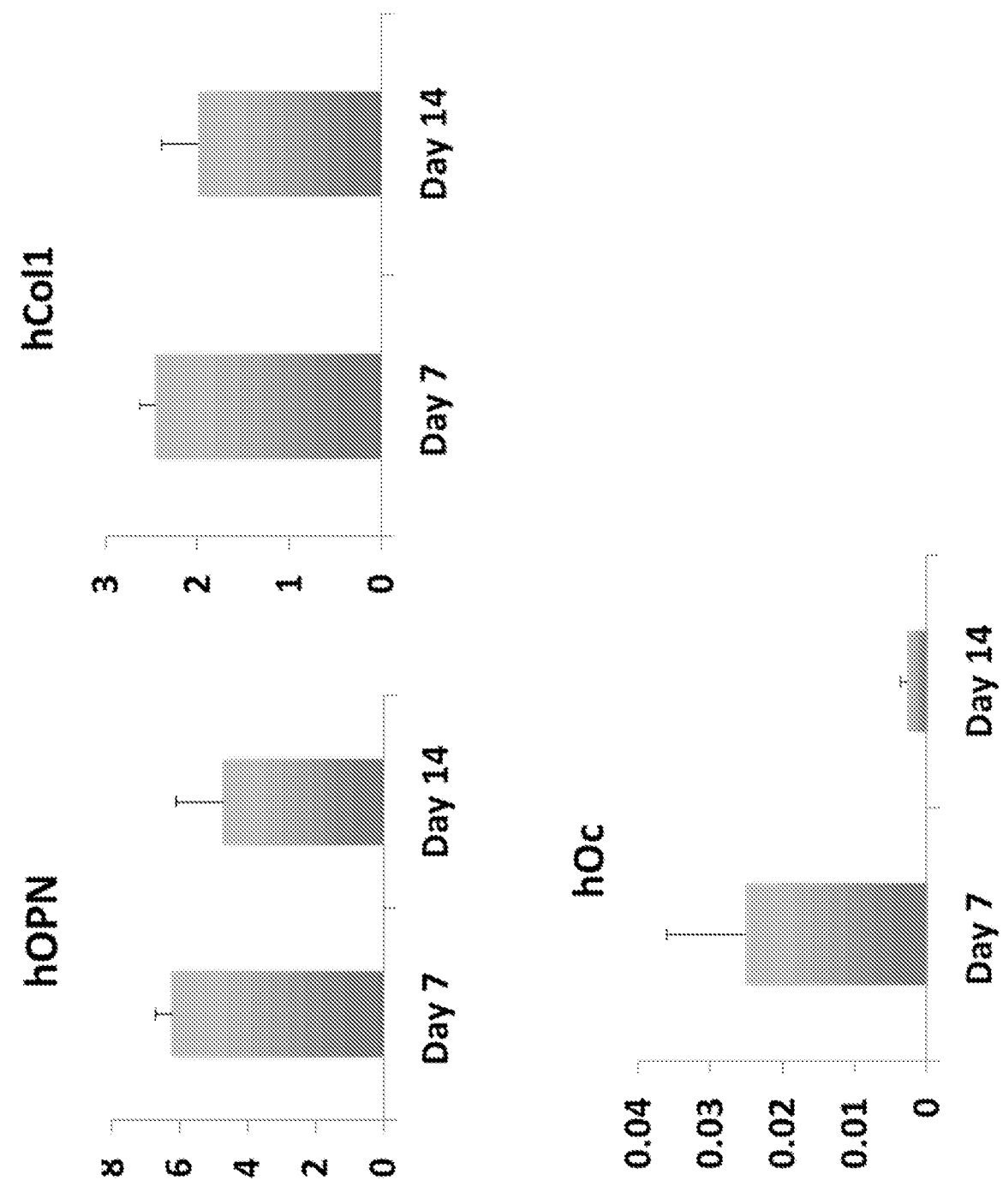

Further confirmation of MSC identity can be provided via differentiation studies. For example, the hBM-MSCs were capable of differentiation in vitro to both adipogenic (FIG. 2A) and osteogenic (FIG. 2B-C) lineages. Following adipogenic induction the cells were stained with Oil Red O and the staining was quantified using optical density (FIG. 2A). After osteogenic induction, successful lineage differentiation is shown by ALP colorimetric assay (FIG. 2B) and osteogenic genes expression (FIG. 2C). OPN=osteopontin, ALP=alkaline phosphatase, ColI=collagen type I, OC=osteocalcin

Example 4

PTH Enhances MSC Homing to Vertebral Bone Defects

Briefly, study models can include osteopenia in immunodeficient rats using ovariectomy and four months of low calcium diet, multiple vertebral defects in the lumber spine of the osteopenic rats can be created, human bone marrow-derived MSCs are labeled with reporter genes for in vivo tracking Rats with lumbar defects can be treated either with: 1. Single or multiple intravenous injection of labeled stem cells and daily sub cutis injections of PTH (40 ug/Kg body weight); 2. MSC injections only; 3. PTH injections only; or 4. Saline injections as a control. Cell survival and homing to the defect sites is monitored using noninvasive optical and nuclear imaging followed by immunohistochemistry, or vertebral repair is monitored using weekly micro-CT scans.

Figure 4:
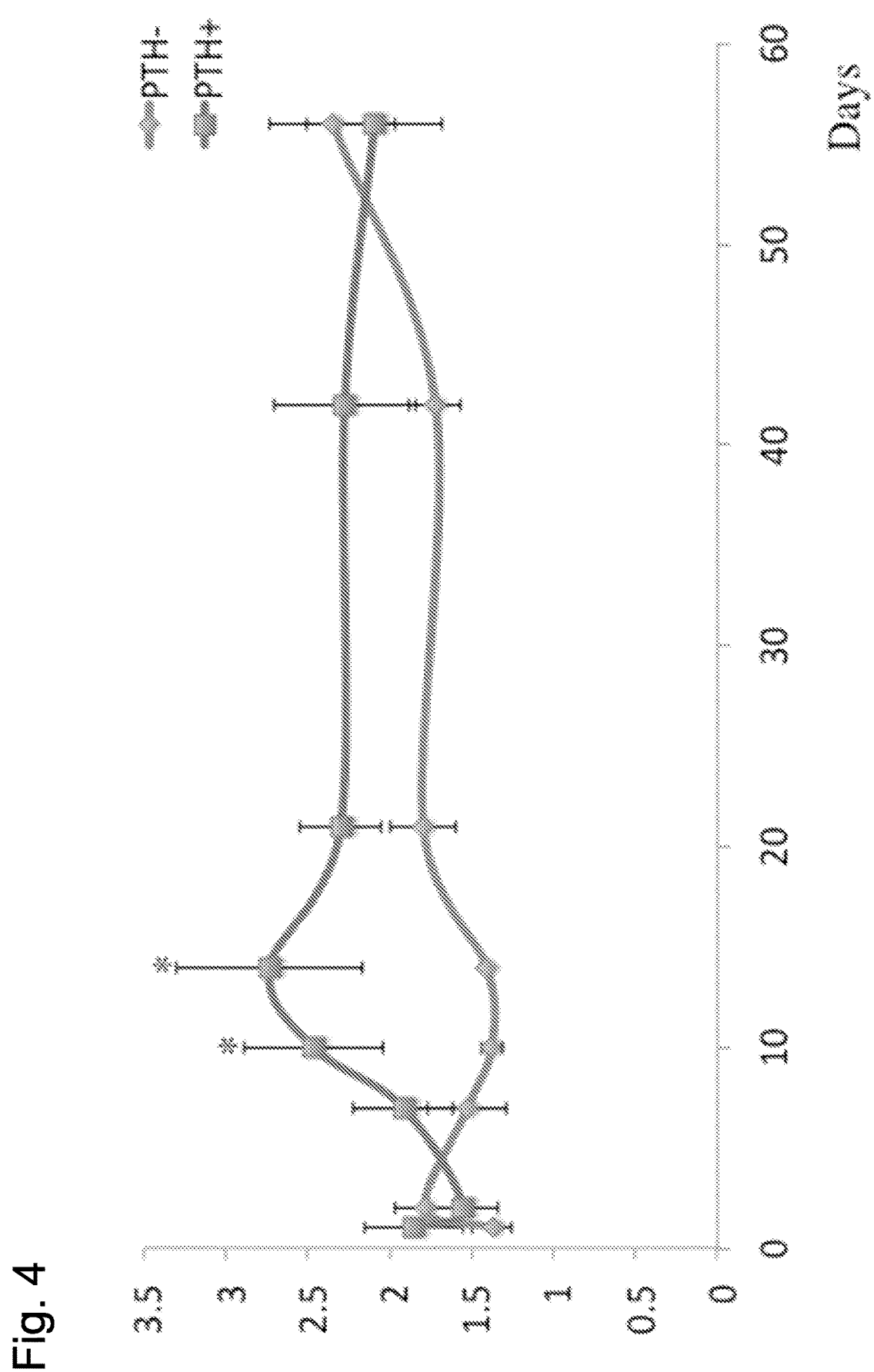
FIG. 4. Longitudinal monitoring and quantification of Luc2-hMSCs homing to the lumbar region of osteoporotic rats with vertebral defects (n=5; p<0.05). Bioluminescent signal values from the lumbar spine region can be calibrated to an internal region of interest (ROI) in each animal.
Figure 5:
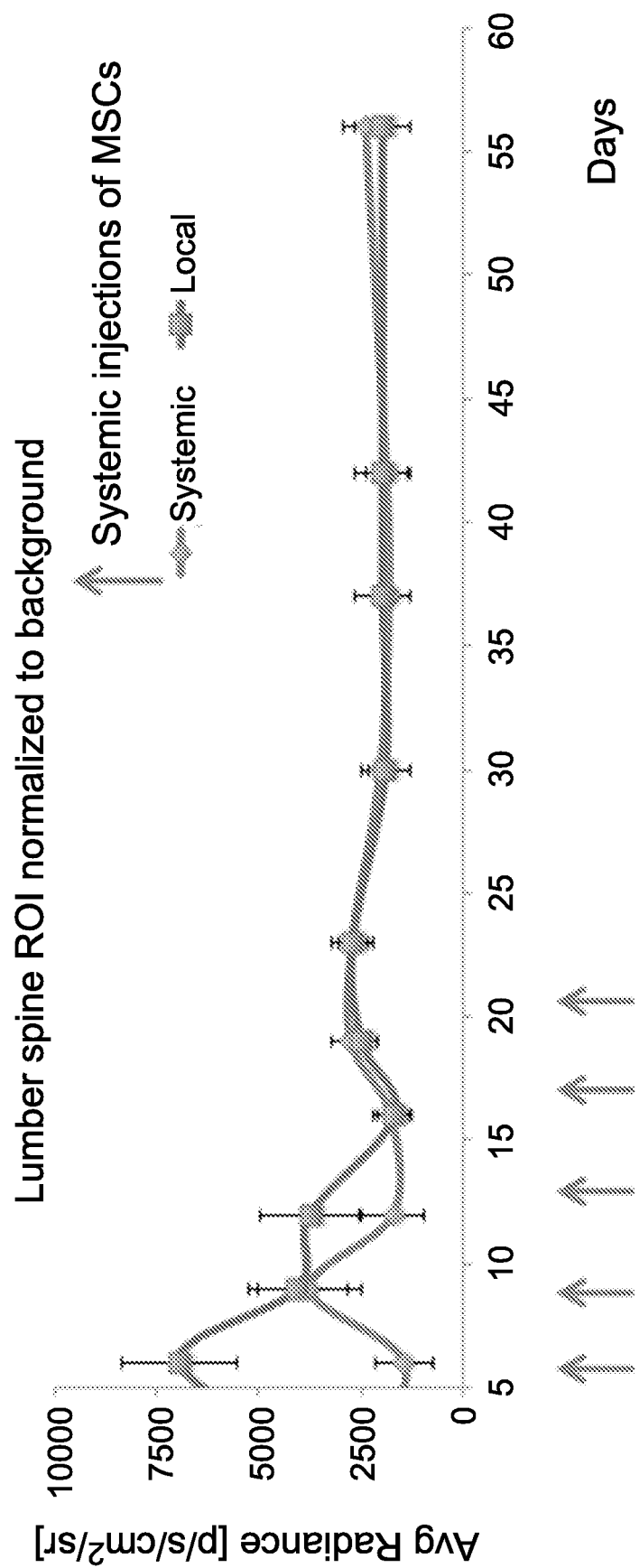
FIG. 5. Longitudinal monitoring and quantification of Luc2-hMSCs homing to the lumbar region of osteoporotic rats with vertebral defect. Bioluminescence imaging was used to monitor MSC homing to the lumbar region of osteoporotic rats. 'Systemic'=i.v. injected MSCs; 'Local'=MSCs implanted directly at the vertebral bone defect. Bioluminescent signal values from the lumbar spine region were calibrated to an internal region of interest (ROI) in each animal.

More specifically, human MSCs are isolated from bone marrow samples according to the described protocols. The cells are infected using a lenti vector encoding for Luciferase 2 (Luc2) and then injected, via the tail vein, $10^6$ Luc2-labeled hMSCs to osteoporotic Nude rats with two lumbar bone defects, each. The cells are injected 7 days after generation of the lumbar bone defects. One group of animals is treated with PTH (40 mg/kg/day s.c.) for three weeks and another group is treated with PBS injections, as a control. Rats are subjected to bioluminescence imaging (BLI), under anesthesia, at different time points. Luminescent signal is not detected from numerous sites in the body of the rats, but could be detected at the lumbar region. Measurements were quantified and are still detectable 55 days post injection (FIG. 4). Interestingly, significantly more Luc2 signal was detected in the $2^{nd}$ week post cell injection, when PTH was administered to the animals, indicating that PTH enhanced cell homing to the lumbar region.

Figure 6:
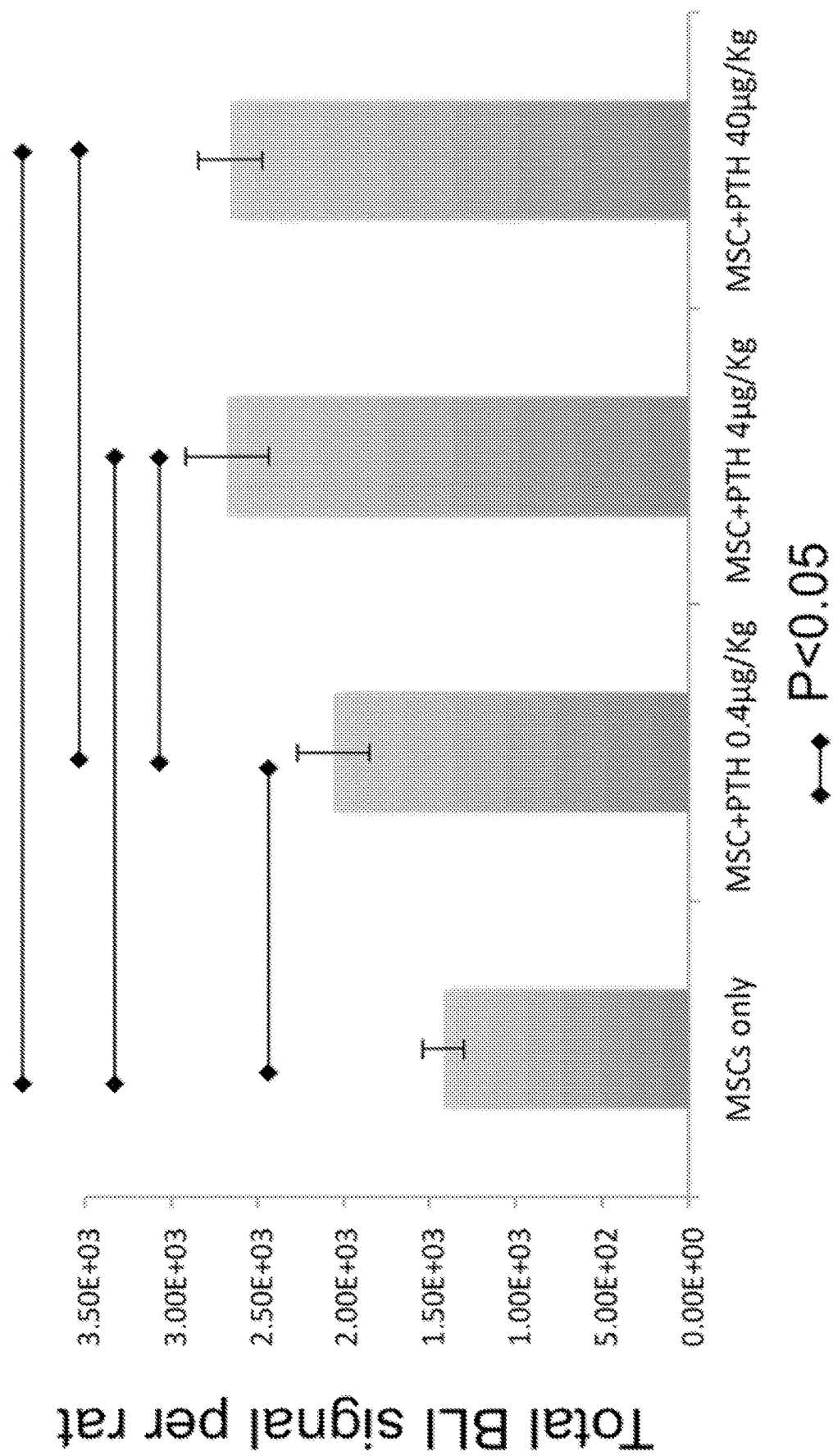
FIG. 6. The effect of PTH dose of Luc2-labeled MSC homing to vertebral defects in osteoporotic rats. Osteoporotic rats with vertebral defects were injected with $5 \times 10^6$ Luc2-MSCs and treated with 0, 0.4, 4 and 40 ugr/Kg PTH daily for 3 weeks. BLI was used to monitor cell homing to the lumbar region over a period of 57 days. Graph shows the total bioluminescent signal over time per group.

Finally, the Inventors evaluated the effect of different PTH doses on MSC homing to vertebral defects. Luc2-labeled MSCs are injected five times to osteoporotic rats and a course of 0.4 ugr/Kg or 4 ugr/Kg PTH is administered daily for three weeks. BLI is performed at different time points and image analysis is used to quantify the Luc2 signal in the lumbar region of each animal. For the purpose of comparison, the total bioluminescent signal over time is calculated in each group. When compared to previous results in which 0 or 40 ugr/Kg PTH was administered, MSC homing increased in correlation with PTH dose. 4 and 40 ugr/Kg doses of PTH induced a similar effect on MSC homing (FIG. 6).

Example 5

PTH Induces Osteogenic Differentiation of Intravenously-Injected MSCs

Figure 7:
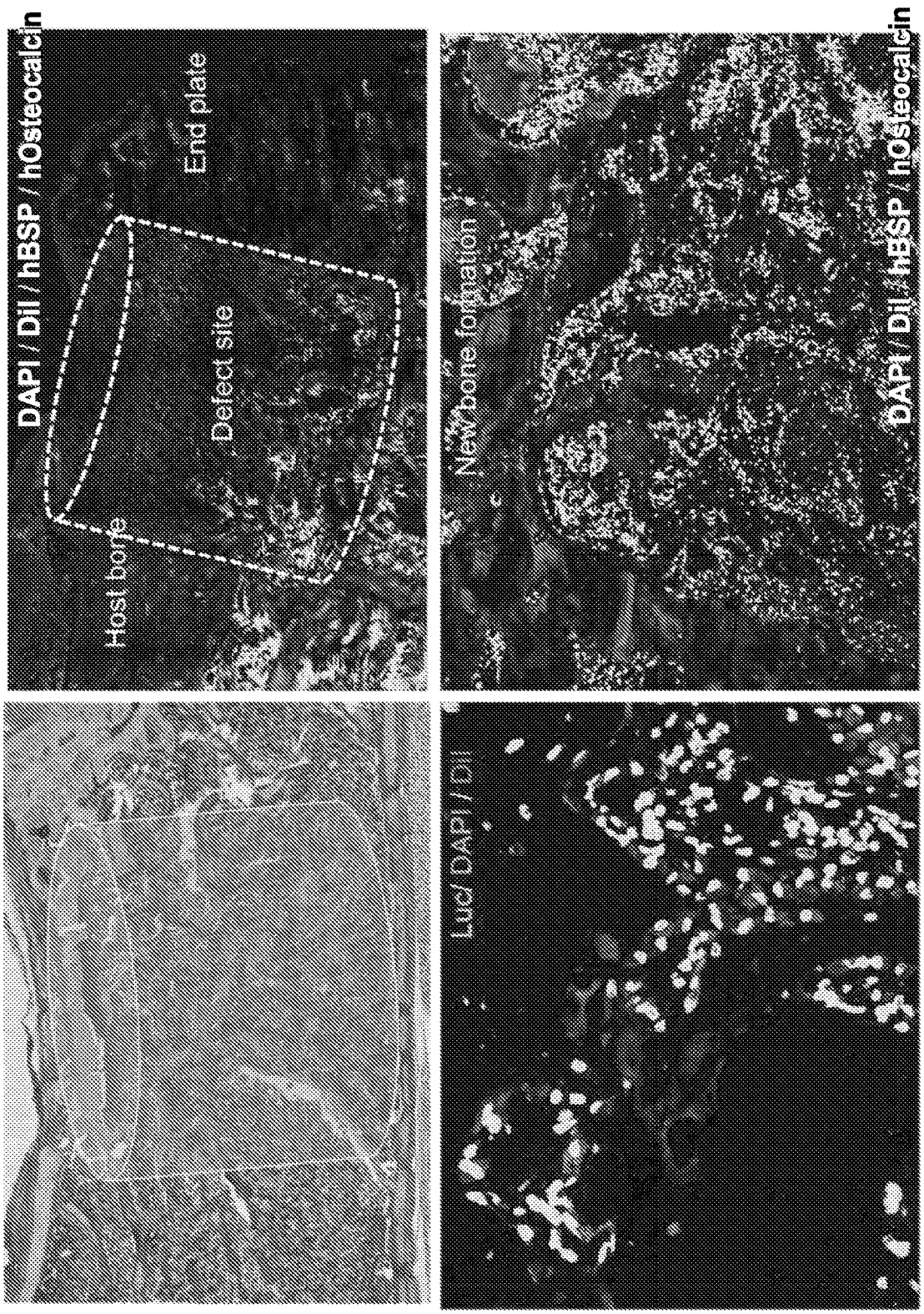
FIG. 7. Immunohistofluorescence staining of rat vertebra after a defect had been created and treatment combining Luc2-labeled MSCs and PTH was administered. A cylinder shape depicts the site of the bone defect. Cell nuclei were stained with DAPI (blue). Injected MSCs were labeled either with DiI (red) or luciferase (green). BSP positive cells appear as pink and osteocalcin positive cells, as green. Overlay images show numerous labeled cells that also express BSP and osteocalcin. There are also non-labeled cells that express BSP and osteocalcin. These could be host cells that contribute to the bone repair process.

Rats with vertebral defects that were treated with iv injection of MSCs and s.c. administration of PTH were sacrificed, operated vertebrae were excised, sectioned and used for immunofluorescence analysis. The Inventors used an anti-luciferase antibody to detect the cells and anti-bone sialoprotein (BSP) or anti osteocalcin (OC) to demonstrate cell differentiation to the osteogenic lineage. Confocal imaging showed Luc-expressing cells integrated in the new bone tissue generated at the bone defect site. Moreover it was evident that the same cells also differentiated to bone-cells since they stained positively for BSP and OC (FIG. 7).

Example 6

SDF-1/CXCR4 Molecules Play a Role in the Homing of MSCs Induced by PTH

The Inventors also evaluated the expression of certain molecules that could explain the mechanism behind MSC homing to vertebral defects and the effect of PTH on this process. As described, the SDF-1/CXCR4 axis is the most widely reported pathway by which hematopoietic and also MSCs are known to migrate to specific locations.

Figure 8:
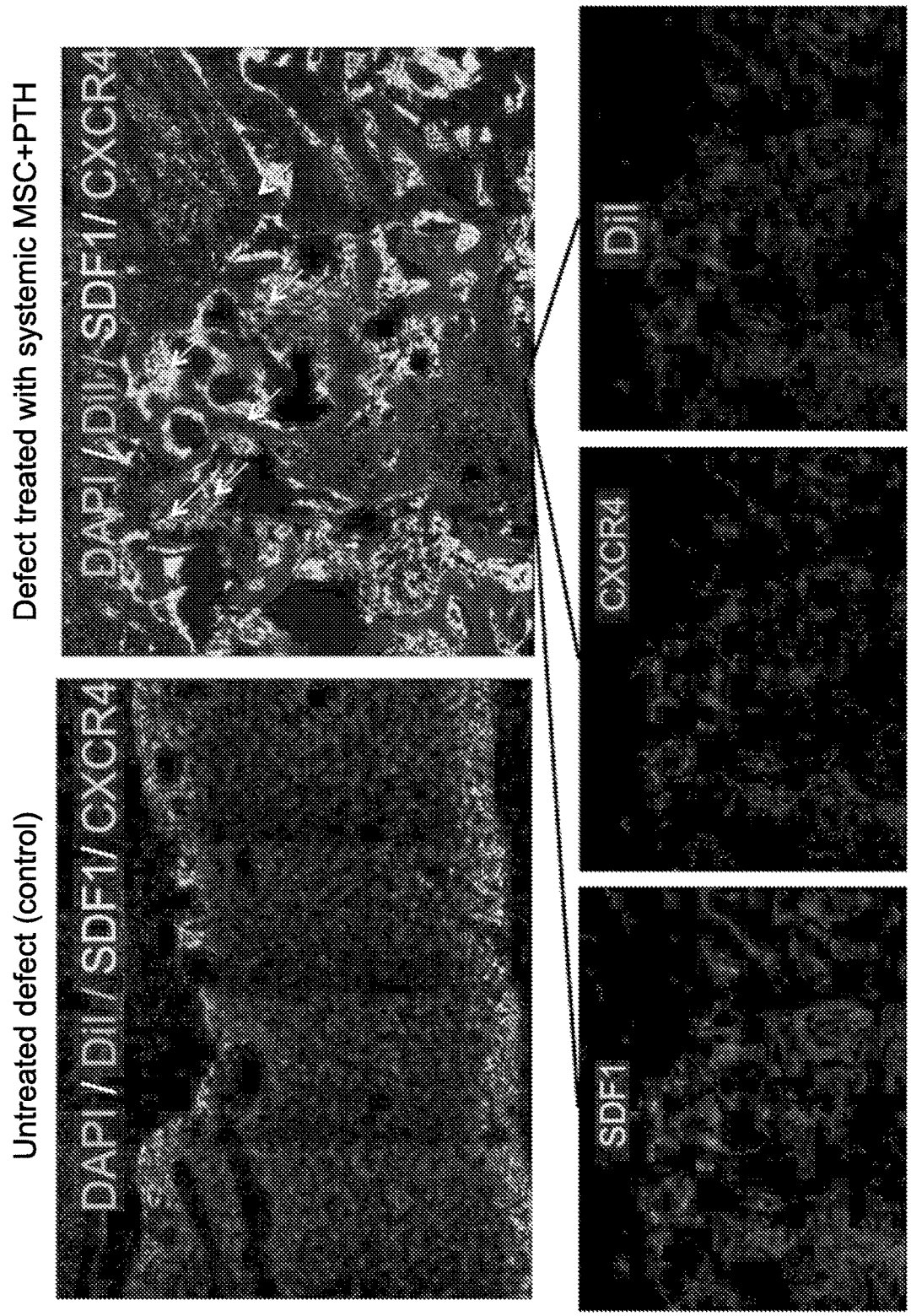
FIG. 8. MSC homing to vertebral defects is probably mediated by the SDF-1/CXCR4 axis. Immunofluorescence showing cells that stained positively to SDF-1 (green) at the defect site. DiI-labeled MSCs (red) also stained for CXCR4 (pink). Control vertebra was not stained for any of these markers.

Using immunofluorescence staining via anti-SDF-1 and CXCR4 antibodies on histological sections of vertebrae harvested from osteoporotic rats treated with DiI (fluorescent, lipophilic, dye)-labeled MSCs and PTH, the Inventors discovered that many cells at the vertebral defect site were expressing SDF-1, while DiI labeled MSCs were expressing the CXCR4 receptor (FIG. 8). Control defects that were not treated with MSCs and PTH showed no positive staining for any of these markers.

Example 7

MSC-PTH Treatment Enhances Bone Repair in Vertebral Defects Created in Osteoporotic Animals In further studies, the Inventors created vertebral bone defects in the lumbar region of osteoporotic Nude rats (two defects per rat). One week post operation, the rats are treated either with a daily injection of PTH s.c. (0, 0.4, 4 and 40 ug/kg) for three weeks, or injected i.v. with $5 \times 10^6$ hMSCs+ the PTH regime or untreated. The rats are scanned using in vivo microCT on Day 1 post surgery and then on Weeks 2, 8 and 12.

Figure 9:
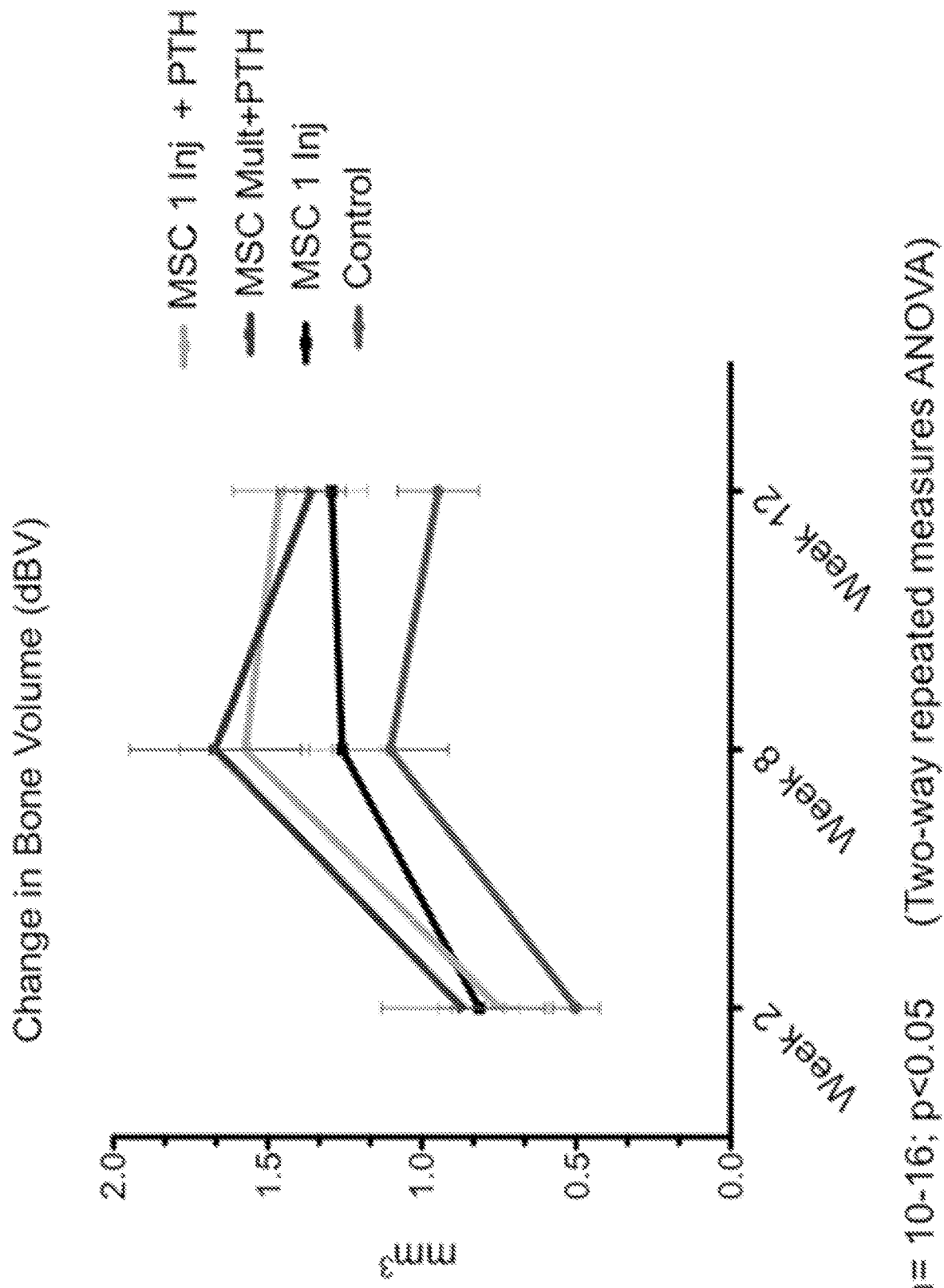
FIG. 9. Bone volume analysis of injured rat vertebrae following MSC or MSC+PTH treatment (MSC 1 inj=single i.v. injection of MSCs; MSC Mult=5 injections of MSCs; Control=untreated).
Figure 10:
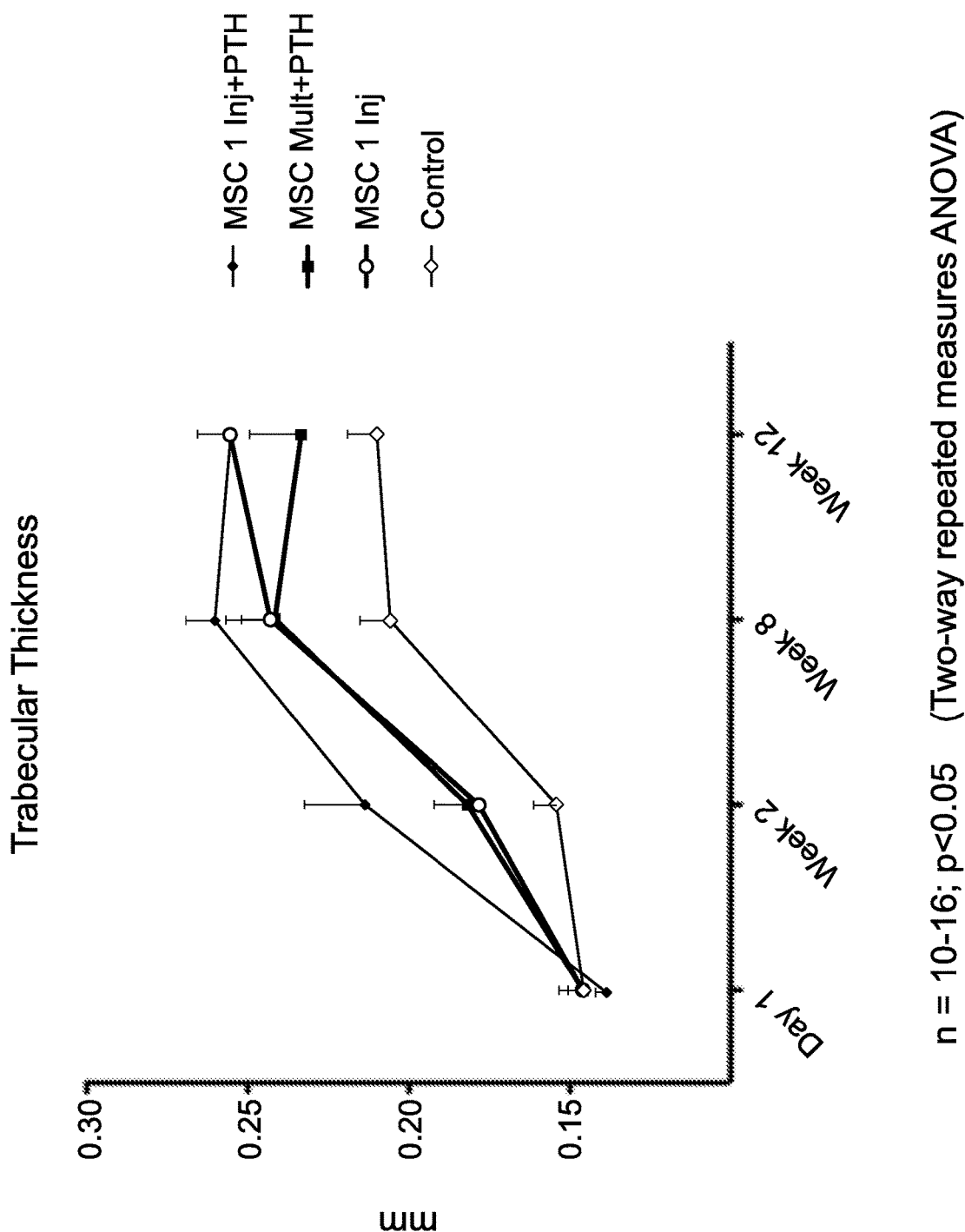
FIG. 10. Trabecular thickness analysis of injured rat vertebrae following MSC or MSC+PTH treatment (MSC 1 inj=single i.v. injection of MSCs; MSC Mult=5 injections of MSCs; Control=untreated).

Quantitative analyses indicates that in the untreated group, vertebral defects remain visible even 8 weeks post-surgery, while the PTH and MSC+PTH (40 ug/kg) treated rats show much higher bone formation in these sites. When calculating bone formation at the vertebral defect sites, based on changes in bone volume density (compared to Day 1), it was discovered that the MSC+PTH group had significantly higher values compared to the groups treated with either MSCs or left untreated (FIG. 9). In addition, trabecular thickness was also significantly increased with the MSC+PTH treatment (FIG. 10).

Variations on this approach can further apply lower doses of PTH (0.4 and 4 ug/kg) and MSCs on bone repair in vertebral defects, as these particular does are closer to the clinical does currently used with osteoporosis patients for the prevention of fragility fractures].

Example 8

Figure 11:
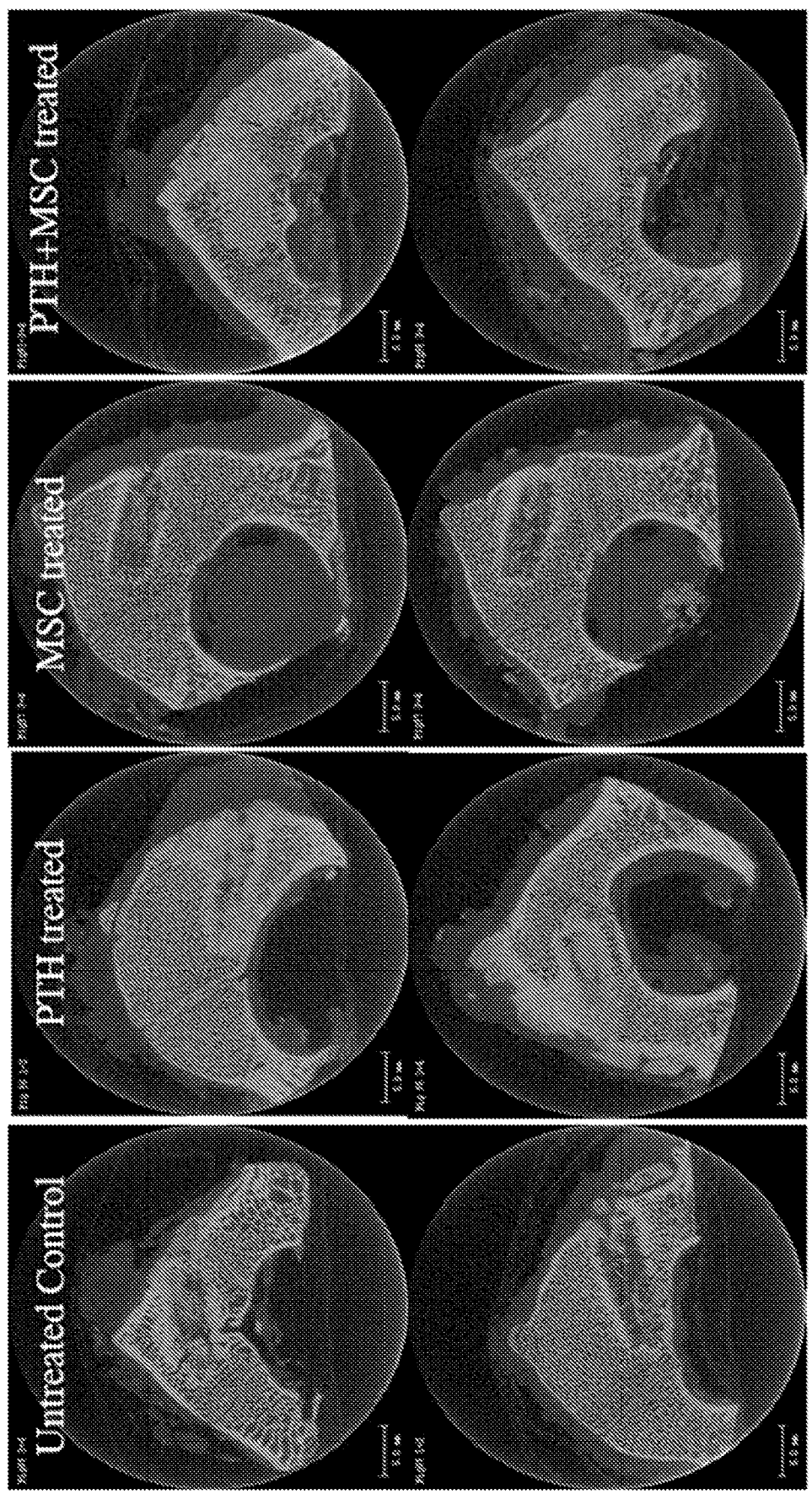
FIG. 11. Combined systemic ADSCs+PTH treatment has synergistic effect on vertebral defect healing in porcine model as early as 4 weeks after surgery (μCT imaging).

A Combined Treatment of Adipose Derived MSCs (ADSCs) and PTH Induces Accelerated Bone Regeneration in a Pig Model of Vertebral Bone Fractures Bone voids were created in lumbar vertebrae of mini pigs (4 mm in diameter and 15 mm in depth). Porcine ADSCs were isolated according to the described protocol. Each pig is injected iv with 50 million ADSCs once a week for four weeks. In addition, the pigs are injected with either PTH 40 ugr/kg/day for 4 week or with PBS. Two additional groups of pigs receive either PBS only or PTH. Vertebral defect repair is monitored and analyzed using X-ray imaging and histology. MicroCT analysis showed remarkable healing of the defect as early as 4 weeks after the surgery (FIG. 11). Notably the combined ADSCs-and-PTH therapy succeeded to regenerate the defect in much more efficient way than both treatments alone.

Example 10

Discussion

Ovariectomy and low calcium diet resulted in 15-20% loss of bone mineral density and over 30% reduction in trabecular thickness in the lumbar vertebrae of rats. Optical and nuclear imaging detect homing of the injected stem cells to the lumbar region of the animals few days after intravenous delivery. Immunohistochemistry further demonstrates that the injected stem cells not only homed to the vertebral defect site, but also differentiated to bone-forming cells. Finally, vertebral defects in osteopenic rats treated with the combined stem cell-and-PTH therapy resulted in 2-fold increase in bone volume density two months after treatment when compared to defects treated with MSCs only.

These results provide evidence that treatment of vertebral and other complex fractures especially in osteoporotic patients can benefit from multiple i.v. injections of MSCs coupled with intermittent PTH administration, as shown by complete vertebral bone defect repair within one month. These remarkable results compare favorably to the bone defects in animals treated with PTH or MSC only, in which significantly less bone repair was seen.

Example 11

Additional Study Design

The Inventors first tested the Inventors' hypothesis in an osteoporotic immunocompromised rat model and later in a minipig model (FIGS. 12 A, B). In the rat model, hMSCs were injected systemically in combination with either ldPTH or hdPTH. The extent of hMSC homing to vertebral injury sites and the possible mechanisms for this activity were evaluated using optical imaging and immunofluorescence. Bone regeneration was quantified by using in vivo μCT in the rat model and by using in vivo x-ray and ex vivo μCT images in the minipig model; regeneration was validated by performing histological analyses. The biodistribution of MSCs and the possible systemic effects of the treatment were evaluated as well.

Example 12

Culturing of MSCs and Labeling with Reporter Genes

Fresh human bone marrow was purchased from Lonza (Walkersville, Md.), and hMSCs were isolated according to a standard procedure. Briefly, bone marrow mononuclear cells were collected and plated at a density of $2 \times 10^5$ cells/cm2. The pMSCs were isolated from porcine adipose tissue as previously reported. Briefly, subcutaneous adipose tissue was harvested from euthanized minipigs, following which mononuclear cells were retrieved using enzymatic digestion and then plated at a density of $10^6$ cells/cm2. The media used for both cell types were changed two times per week.

hMSCs were transduced with a lentiviral vector harboring Luc2 under the constitutive ubiquitin promoter, whereas pMSCs were transduced with a lentiviral vector harboring green fluorescent protein (GFP) and firefly luciferase (Luc) under the ubiquitin promoter. Plasmids were generously provided by Dr. Joseph Wu (Stanford University, Stanford, Calif.) and Dr. Eduardo Marban (Cedars-Sinai Medical Center, Los Angeles, Calif.). Both vectors were produced in 293HEK cells before their transduction. GFP expression was verified using flow cytometry and Luc expression was demonstrated using in vitro BLI (Xenogen IVIS Spectrum, PerkinElmer, Waltham, Mass.). For microscopic cell identification, the cells were labeled with Vibrant-CM-DiI (Invitrogen, Life Technologies, Grand Island, N.Y.), as previously described, immediately before injection.

Example 13

Vertebral Defect Models

All procedures described in this study were approved by the Cedars-Sinai IACUC. Multiple vertebral defects were created in lumbar spines of osteopenic rats and healthy minipigs. These procedures are described in details in Supplemental Materials.

Rats: Following anesthetization, a sterilized surgical scalpel was used to create a 5-cm incision in the skin of each rat, and sterile soaked gauzes were used to wrap the internal organs. Next, L4 and L5 vertebral bodies were exposed. A micromotor drill (Stoelting, IL) with a 1.8 mm-diameter sterile trephine drill bit was used to create a 2.5-mm-deep bone defect through the center of the vertebral body. The subcutaneous tissue layer was sutured in a continuous pattern using an absorbable Vicryl 3-0 Braided (Ethicon Inc.), and the skin was sutured in a subcuticular pattern using a nonabsorbable Ethilon 2-0 Monofilament. Finally, the skin area was cleansed with sterile gauzes and a solution of 0.5% chlorhexidine gluconate.

Pigs: Following an 18-hour preoperative fast, each pig was sedated with intramuscular drugs (acepromazine 0.25 mg/kg, ketamine 20 mg/kg, and atropine 0.02-0.05 mg/kg), following which the animal was injected intravenously with propofol (2 mg/kg) to induce full anesthesia. After this had been achieved, the trachea was intubated and anesthesia was maintained using 1-3.5% isoflurane inhaled via the tracheal tube for the duration of the procedure. A 20-cm posterolateral skin incision was made over the lumber region (L2-5), which was then exposed by a lateral transpsoas retroperitoneal approach. In each vertebra, a critical-size cylindrical bone defect, 15-mm in depth and 4-mm in diameter, was created. After surgery, the subcutaneous tissue was closed with an absorbable subcutaneous suture and the skin with an absorbable subcuticular suture. The animal received perioperative antimicrobial prophylaxis and postoperative analgesia.

Example 14

Systemic Treatment with MSCs and PTH

Beginning on postop Day 3, the rats were given PTH or PBS administered subcutaneously (SQ) daily for 3 weeks. Two different dosages of teriparatide (Forteo™, Eli Lilly, Indianapolis, Ind.)—0.4 µg/kg/day (ldPTH) or 4 µg/kg/day (hdPTH)—were used. The pigs were administered research-grade PTH (1.75 µg/kg/day) resuspended in 0.9% NaCl (adjusted to pH5) and heat-inactivated (56° C., 1 h) 2% pig serum (Sigma-Aldrich) or drug vehicle for 4 weeks beginning on postop Day 5. Rats receiving systemic MSCs treatment were anesthetized by inhalation of 2-3% isoflurane and injected intravenously with hMSCs-Luc2 via the tail vein. Each rat received a total of five injections: $2 \times 10^6$ cells per injection, every 3-4 days beginning on postop Day 3. Pigs receiving systemic MSCs treatment were injected intravenously with pMSCsLuc. Each pig received a total of 4 injections beginning on postop Day 5 and thereafter once a week. For each injection, $50 \times 10^6$ cells were suspended in 5 ml sterile saline and injected via the ear vein and flushed with additional 5 ml saline.

Example 15

Imaging of MSCs as they Home to the Vertebral Defect Site In Vivo

Luciferase expression in the defect site was quantified using a BLI system, as described previously. Briefly, before light detection, the rats were anesthetized by continuous administration of 1-3% isoflurane mixed with 100% oxygen. Ten minutes before imaging the rats were given an intraperitoneal injection of 126 mg/kg luciferin (Promega Corp., Madison, Wis.) in PBS. Light emission was evaluated using the IVIS Spectrum. The exposure time was set automatically, and the bioluminescence was quantified as the total signal normalized to the exposure time and area of the region of interest.

Example 16

µCT Analysis of Intact and Operated Vertebrae

In Vivo Micro-Computed Tomography Analysis.
Vertebrae were evaluated using a cone-beam in vivo µCT imaging system (vivaCT 40; Scanco Medical, Brüttisellen, Switzerland). Microtomographic slices were acquired using an xray tube with a 55-kVp potential, and reconstructed at a voxel size of 35 µm.
Assessment of Vertebral Defect Repair.
Histomorphometric 3D evaluation was performed on a volume of interest (VOI) including the trabecular region of the whole vertebra. A constrained 3D Gaussian filter ($\sigma=0.8$, support=1) was used to partly suppress VOI noise. The trabecular bone tissue was segmented from marrow and soft tissue by using a global thresholding procedure. A quantitative assessment of BVD and AD based on microtomographic data sets was created using direct 3D morphometry.
Assessment of Vertebral Defect Repair.
Rats: To analyze healing, the animals were imaged on Day 1 and again 2, 4, 8, and 12 weeks after generation of the defect. Defect margins were located on Day 1 scans and aligned to a standard position, and a cylindrical VOI (1.68 mm in diameter, 2.52 mm in height) was defined for 3D histomorphometric evaluation. Subsequent µCT scans (those obtained at postop Weeks 2, 4, 8, and 12) obtained in each rat were automatically registered to the standard position defined for the corresponding Day 1 scan with the aid of Analyze imaging software (AnalyzeDirect, KS). The anatomical match obtained by the registration procedure allowed us to apply the exact predefined VOI of Day 1 to all remaining time points. Bone volume density (BVD) and apparent density (AD) of the VOI were used to assess new bone formation.
Pigs:
To analyze healing, x-ray films were obtained 1 week and 5 weeks after surgery. The pigs were sedated by intramuscular administration of ketamine (10 mg/kg) and dexmedetomidine (0.08 mg/kg). Fluoroscopic images were acquired using the INFX-8000F DP-I system (Toshiba, Japan). Animals were placed in lateral recumbency and rotational acquisition was performed. The pigs were monitored during recovery from anesthesia. Immediately after the second sets of images had been obtained, the pigs were euthanized and their vertebrae excised. The vertebrae were scanned with µCT and evaluated in a previously described manner. Each defect was aligned to a standard position, and a cylindrical VOI (4 mm×15 mm) was defined for 3D histomorphometric evaluation. Both the BVD and AD of the VOIs were used to assess new bone formation.

Example 17

Histological Analysis and Immunofluorescence Imaging

Histological analysis was performed on rat vertebrae that had been retrieved 12 weeks postop (at the endpoint of the experiment) and on pig vertebrae that had been retrieved after 5 weeks. The vertebrae were sectioned and stained using H&E for morphological analysis, as previously described. For immunofluorescent staining, tissues were deparaffinized and the antigens were retrieved by incubation in preheated Target Retrieval Solution™ (Dako, Carpinteria, Calif.) for 45 min in 37° C. Nonspecific antigens were blocked by applying blocking serum-free solution (Dako). Slides were stained with primary antibodies against human BSP and Oc to examine osteogenic differentiation, and with SDF1, CXCR4, EGFR, and amphiregulin to determine the MSC homing mechanism. The primary antibodies were applied to the slides and incubated in 4° C. overnight, washed off using PBS, and the slides were incubated with secondary antibodies (Table 1) for 1 hr in room temperature, after which they were washed off (Table 1) with PBS. Slides were then stained with 4',6-diamidino-2-phenylindole dihydrochloride (DAPI, 1 µg/ml) for 5 min in the dark, after which they were again washed three times with PBS. A VectaMount mounting medium (Vector Laboratories, Burlingame, Calif.) was applied to the tissue. The slides were imaged using a four-channel Laser Scanning Microscope 780 (Zeiss, Pleasanton, Calif.) with 20× magnification, z-stacking, and 5×5 tile scanning. For zoom-in images a single zstacked image was generated. All samples were scanned using the same gain and exposure settings.

TABLE 1

Antibodies used for the immunofluorescence.

| Antigen | Primary antibody | Primary antibody dilution | Secondary antibody (Jackson ImmunoResearch Laboratories, | Secondary antibody dilution |
|---|---|---|---|---|
| Bone Sialoprotein | BSP, mouse anti-human, Millipore, Temecula, CA | 1:250 in 3% Donkey serum and | Cy5-conjugated donkey anti-mouse antibody | 1:1000 in 0.3% PBS-T |
| CXCR4 | Goat anti-human/rat CXCR4, Abcam | 0.3% Triton | Alexa Fluor ® 647 donkey anti-goat antibody | |
| Osteocalcin | Oc, rabbit anti-human/rat, Millipore | | Alexa Fluor ® 488 donkey anti-rabbit | |
| SDF1 | Rabbit anti human/rat, Abcam, Cambridge, MA | | | |
| Amphiregulin | Amp, rabbit anti-human/rat, Bioss, Woburn, MA | 1:200 in 3% Donkey serum and | | 1:500 in 0.3% PBS-T |
| EGFR | Mouse anti-human EGFR, BioLegend, San Diego, CA | 0.3% Triton | Cy5-conjugated donkey anti-mouse antibody | |

Example 18

Osteoporotic Rat Vertebral Fracture Model: Additional Procedures

Induction of Osteoporosis

Forty six-week-old female athymic rats (Hsd:RH-Foxnlrnu) whose ovaries had been surgically removed were purchased from Harlan Laboratories (Indianapolis, Ind.). Upon arrival at our facility the rats were placed on a low-calcium diet (LCD) consisting of 0.01% calcium and 0.77% phosphate (Newco Distributors, Inc., Calif.) for 4 months before surgery, after which a regular diet was provided ad libitum. (Data shown in FIG. 19 were obtained in rats in which the LCD was maintained for 8 months; these animals were the exception.)

Preoperative Care and Surgical Anesthesia

Each rat was anesthetized by administration of 2-3% isoflurane and place in dorsal recumbence on a 37° C. heating pad. The skin over the lumbar region was cleaned, clipped free of hair, and swabbed with Betadine® followed by alcohol three times. Prior to surgery, the animal received a subcutaneous injection of Carprofen (5 mg/kg).

Surgical Procedure

A midline abdominal incision was made and extended through the linea alba into the abdominal cavity to expose the internal organs over the L1-5 vertebrae. Using blunt dissection, a midline incision was made over the desired entry site using sterilized surgical scissors. Blunt dissection is more efficient than cutting because it minimizes bleeding, decreases risks of hematoma and infection, and facilitates wound healing. In addition, when needed, a thermo-cautery tool was used to minimize blood loss during surgery. The internal organs were carefully exposed and set aside to permit access to the anterior portion of the spine. To avoid dehydration, sterile soaked gauzes were used to wrap the internal organs. Using blunt dissection, the anterior edges of the spinal column were isolated from adjacent connective tissue and muscle. A sterile cotton swab saturated with a 3% hydrogen peroxide solution was used to clean residual blood and tissue from the L4 and L5 vertebrae. Using a micromotor drill (Stoelting, IL) with a 1.8-mm sterile trephine drill bit, a single 2.5-mm-deep bone defect was created through the center of each vertebral body, a total of two bone defects per rat. After the bone defect had been completed, the tendon and tissues were put back in place. Then, the organs were returned to their proper positions and the linea alba was closed with an absorbable suture. The subcutaneous tissue layer was closed with an absorbable synthetic monofilament surgical suture, and the skin was closed using a nonabsorbable monofilament suture. Finally, the skin area was cleansed with sterile gauzes and with Betadine® followed by alcohol. A small amount of Dermabond Advanced™ (Ethicon, OH) was applied over the incision to reduce any infection.

Example 19

Pig Vertebral Fracture Model

Animal Model.

A total of 12 adult female Yucatan Mini-pigs (S&S Farms, CA) were used. The mean weight±SD of the animals was 45.0±3.6 kg and the mean age ± was 9.2±1.2 months.

Preoperative Care and Surgical Anesthesia.

The pigs were placed on a fasting diet 18 hours prior to surgery. Analgesia was administered orally (carprofen, 4 mg/kg) on the morning of surgery for pain prevention. Each pig was sedated and immobilized by an intramuscular injection of drugs (acepromazine 0.25 mg/kg, ketamine 20 mg/kg, and atropine 0.02-0.05 mg/kg). Hair was removed from the lumbar region using an electrical clipper. The animal was placed on a heated operating table in the lateral decubitus position, and propofol (2 mg/kg) was injected IV to provide complete anesthesia. The animal's trachea was intubated and anesthesia was maintained by inhalation of 1-3.5% isoflurane via the tracheal tube for the duration of the procedure. The surgical area was prepared using a Wet PVPI Preoperative Skin kit (CareFusion, San Diego, Calif.). A full sterile drape with a center hole was placed over the animal, and the surgical area was covered with a sterile adhesive surgical drape containing Povidine (Jorgensen Labs, CO).

Surgical procedure and postoperative care. A 20-cm posterolateral skin incision was made over the lumber region (L1-L5), which was then exposed via a lateral transpsoas retroperitoneal approach. In each vertebra (L2, L3, L4), one critical-size cylindrical bone defect, 15-mm in depth and 4-mm in diameter, was created, a total of three bone defects per pig. An orthopedic drill with a custom-made drill bit-stopper was used to ensure identical defects. After surgery, both the subcutaneous and subcuticular tissues were closed using absorbable sutures with a simple continuous suture pattern and the skin was closed using a nylon suture with a simple interrupted technique. The animal received perioperative antimicrobial prophylaxis and postoperative analgesics (carpofen and buprenorpnine).

Analysis of Spontaneous Regeneration of the Vertebral Defect.

To analyze spontaneous regeneration of the vertebral defect, the animals were imaged on Day 1 and at Weeks 2, 4, 8, and 12 after the defect had been created. The μCT procedures used to evaluate bone repair at the site of the defect were previously described. Defect margins shown on Day 1 scans were located and reoriented to a standard position, and a cylindrical VOI (1.68 mm in diameter and 2.52 mm in height) was defined for the 3D histomorphometric evaluation. Subsequent μCT scans obtained in each rat at Weeks 2, 4, 8, and 12 were automatically registered to the standard position defined on the Day 1 scan in the same rat by using a novel multiple image registration algorithm. The algorithm, implemented in MATLAB code, performs an initial registration approximation by applying principle component analysis on the point cloud of all segmented voxels that belong to the vertebra, followed by volume-based fine-tuning of the registration with normalized cross-correlation as a similarity measure and downhill descent as an optimization approach. (The Image Registration Toolkit was used under license from Ixico Ltd., London, UK) The anatomical match obtained using the registration procedure allowed us to apply the exact predefined VOI from Day 1 to all remaining time points, resulting in a highly accurate 3D histomorphometric analysis over time. The BVD and AD of the VOI were used to assess new bone formation.

Serological Analysis in Pigs.

To test the possible adverse effect of PTH treatment, pigs were treated with one of three different doses of PTH—1 μg/kg, 1.75 μg/kg, and 5 μg/kg—or no PTH for 28 days. Blood was collected aseptically from the pigs by jugular vein puncture at two time points: before and after treatment. Four milliliters of blood were collected from each pig and placed in Corvac Integrated Serum Separator Tubes. All of the samples were sent to Antech Diagnostic (Irvine, Calif.) for a full chemistry panel analysis.

Example 20

Statistical Analysis

GraphPad Prism 5.0b software (GraphPad Prism, San Diego, Calif.) was used to analyze the data. Results are presented as means±SE; *$p \leq 0.05$; $p \leq 0.01$; *$p \leq 0.001$; ****$p \leq 0.0001$; ns, not significant. Longitudinal data analysis was conducted using a one-way ANOVA or two-way ANOVA with repeated measures and the Bonferroni post-test. To assess significance, $p < 0.05$ was considered statistically significant.

Example 21

Results of Osteoporotic Rat Study

A rat model of postmenopausal osteoporosis was generated in immunocompromised rats that can sustain human cell implantation by ovariectomy in conjunction with a low-calcium diet (LCD); a similar model was previously reported using immunocompetent rats. Once ovariectomy and 4 months of LCD were found sufficient to induce osteoporosis (FIG. 19), a different group of rats underwent this induction protocol and were subsequently switched to a regular diet (post-LCD). Micro-computed tomography (μCT) was used to scan these rats before initiation of the LCD and again on Day 0 and at Weeks 8 and 12 post-LCD to verify the persistence of osteoporosis with little spontaneous bone mass augmentation (FIG. 12C-E). Hematoxylin and eosin (H&E) staining further validated the drastic reduction in the trabecular bone component in the animals' lumbar vertebrae following a 4-month LCD (FIG. 12F). Consequently, a 4-month LCD was deemed optimal to achieve maximal irreversible osteoporosis and was used throughout the study.

Example 22

MSC Homing to Vertebral Bone Defects

Figure 13A:
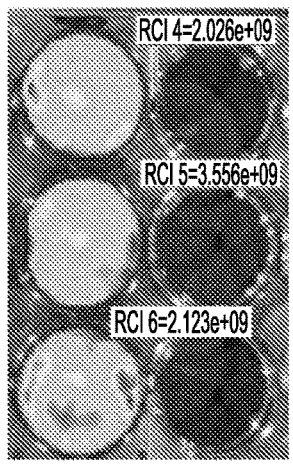
FIG. 13(A) to FIG. 13(D). PTH enhances MSC homing to vertebral defects. Human MSCs were transduced with the lentiviral vector Ub-Luc2. Luc2 expression was verified using in vitro BLI (A) over 6 passages (B). hMSC-Luc2 homing to vertebral defects was tracked over 8 weeks after the first cell injection and quantified by measuring the bioluminescent signal overlying the vertebral defects (red circle, (C)). The average Σ total flux at each time point was calculated and compared using a two-way ANOVA (D) (n=5).
Figure 13B:
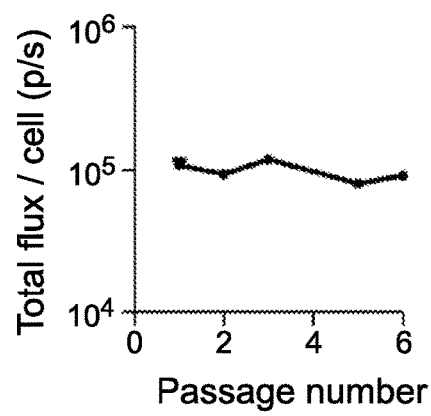

Human MSCs (hMSCs) were infected with a lentiviral vector harboring the reporter gene luciferase2 (Luc2) under the constitutive ubiquitin promoter to allow in vivo imaging of homing activity. Stable transfection of hMSCs-Luc2 and constitutive expression of Luc2 were validated by performing quantitative bioluminescence imaging (BLI) over 6 passages (FIG. 13A, B). No significant change ($p > 0.05$) in Luc2 expression was found in subsequent passages, indicating that BLI could be used to track hMSCs-Luc2 in vivo.

Figure 13C:
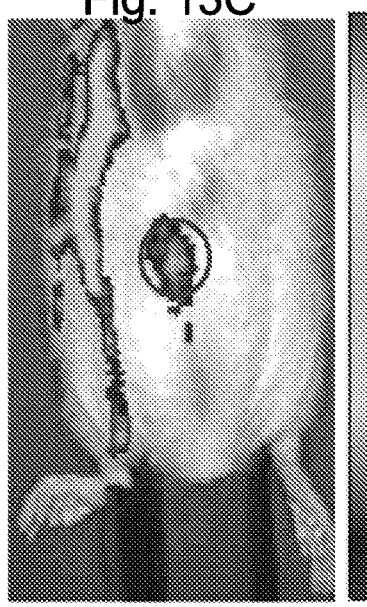
Figure 13D:
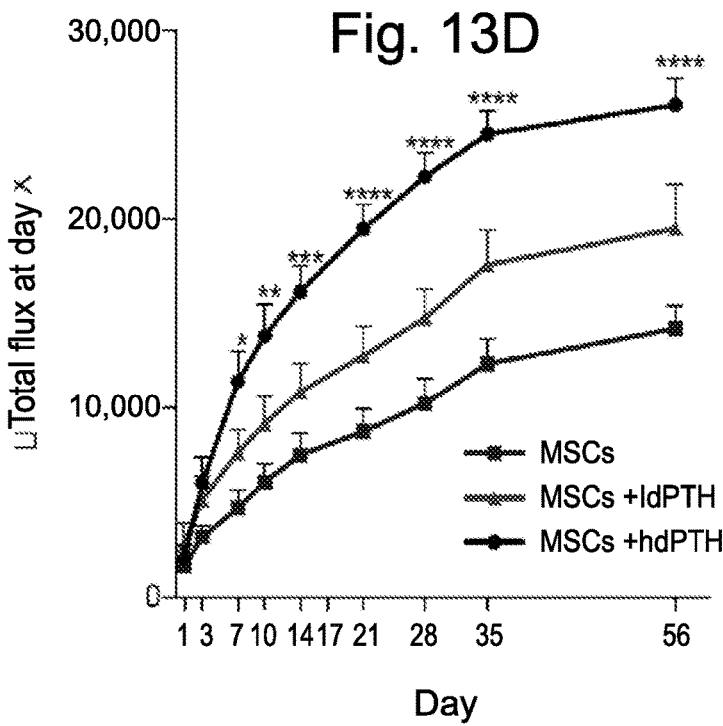

Cylindrical defects were created in two lumbar vertebral bodies in each osteoporotic rat. The rat then received a total of five IV injections of saline or hMSCs-Luc2 and either PBS, lowdosage PTH (ldPTH), or high-dosage PTH (hdPTH) daily starting on postop Day 3 (FIG. 12A). The rats were monitored using BLI for 56 days postop. At each time point the bioluminescent signal overlaying the lumbar region was quantified (FIG. 13C). Next a sum of bioluminescent signals (Σ total flux) was plotted against time for the different treatment groups (FIG. 13D). The results showed a linear increase in Σ total flux ($r2=0.92$) for the hMSCs-Luc2 group during the 56 days of the study, indicating that hMSCs in this group both homed to and engrafted in the lumbar region. A significantly higher Σ total flux was found for rats treated with hMSCs-Luc2+hdPTH as early as 7 days postop ($p \leq 0.05$) and for all subsequent time points ($p \leq 0.01$), but not for rats treated with hMSCs-Luc2+ldPTH. Overall, the trend of accumulation of MSCs in animals treated with MSCs-Luc2+hdPTH was logarithmic ($r2=0.98$), whereas in animals not treated with PTH it was linear, indicating profound changes in the pattern of MSC recruitment to the fracture site and in the cells' subsequent survival.

Example 23

The Effect of hMSC-PTH Treatment on Vertebral Bone Defect Regeneration

Figure 14A:
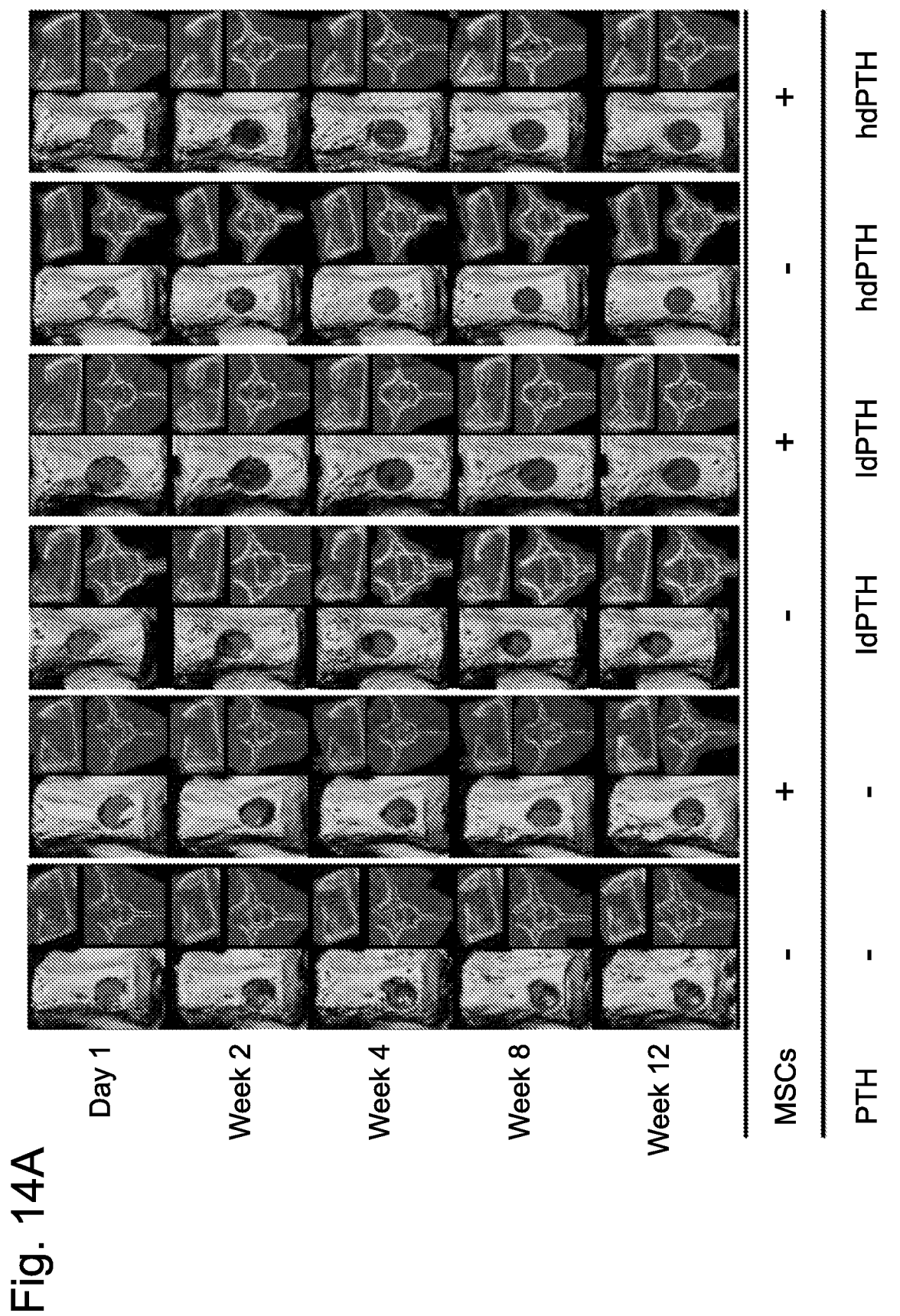
FIG. 14(A) to FIG. 14(C). MSCs-PTH therapy regenerates vertebral defects in osteoporotic rats: μCT analysis. Vertebral bone voids were treated with MSCs or saline and with ldPTH, hdPTH, or PBS. The rats were imaged using μCT 1 day and 2, 4, 8, and 12 weeks postop. (A) A representative vertebral defect at various time points for each group is depicted in each panel as a frontal 3D image (left side) with bone formation in the void indicated in red, a sagittal 2D image (upper right), and an axial 2D image (lower right). Quantitative analysis of bone formation in the voids was performed and bone volume density (B) and apparent density (C) were calculated and compared using a two-way ANOVA (n=10).

The therapeutic effect of combined MSC-PTH therapy was evaluated using two PTH dosages (ldPTH and hdPTH). The effect was then compared to the effect of each treatment alone and to that of no treatment (hereafter referred as "control"). Bone regeneration in vertebral defects was monitored at several time points after surgery by performing in vivo μCT (FIG. 14A). By analyzing the scans, the Inventors were able to quantify bone volume density (BVD; FIG.

Figure 14B:
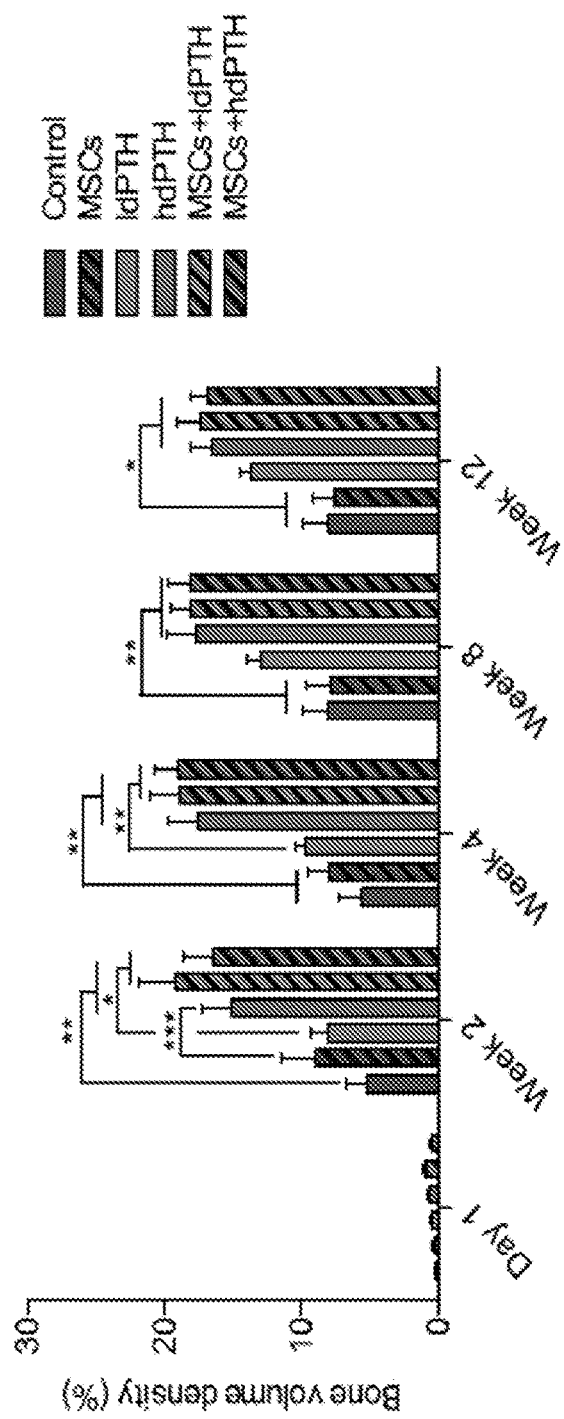
Figure 14C:
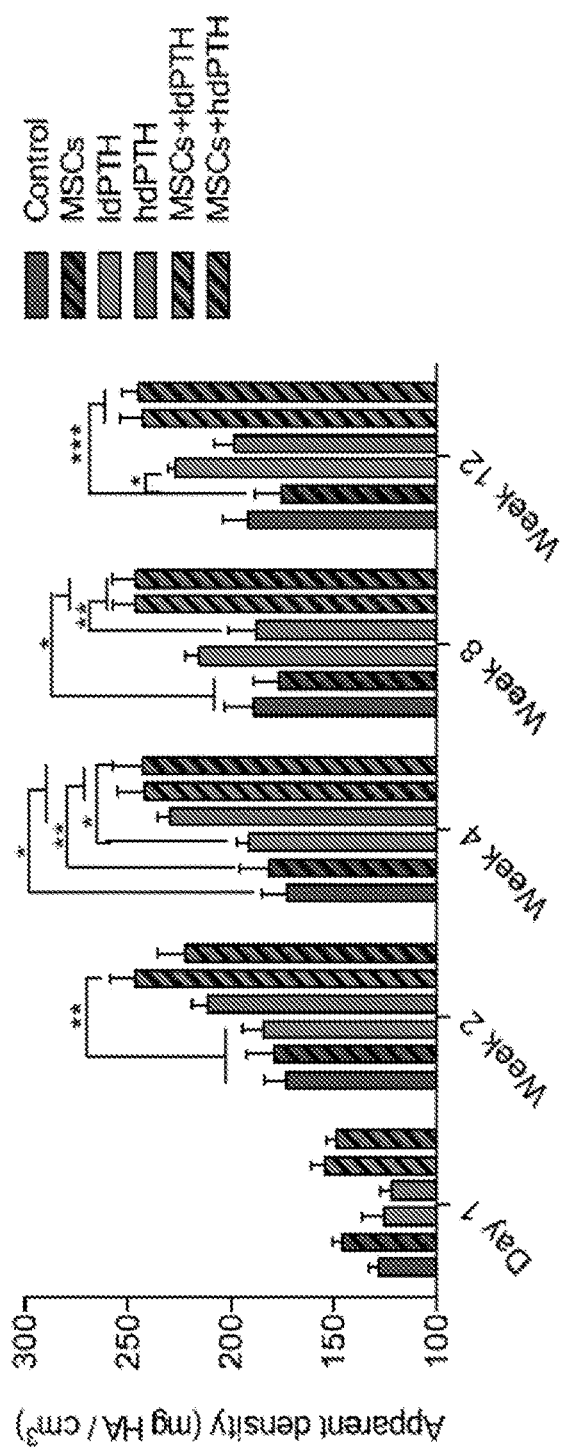
Figure 15A:
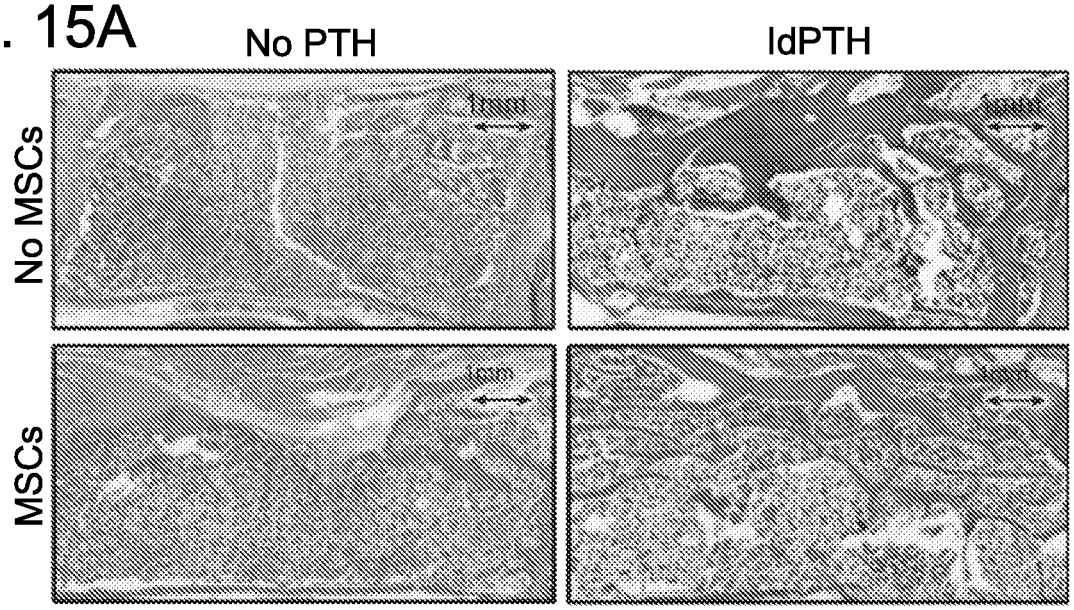
FIG. 15(A) to FIG. 15(B). MSCs-PTH therapy regenerates vertebral defects in osteoporotic rats: histological and immunofluorescence analyses. The injured vertebrae were harvested, decalcified, embedded in paraffin, sectioned, and either stained with standard H&E and imaged with light microscopy (A) or treated with immunofluorescent staining against the osteogenic markers Oc and BSP, and imaged using confocal microscopy (B). Representative vertebral defects display healing differences between animals that received or did not receive ldPTH and MSCs (A). The osteogenic markers can be partially colocalized with DAPI-stained nuclei and DiI fluorescent dye, which was used to label MSCs before their systemic administration (B).
Figure 20A:
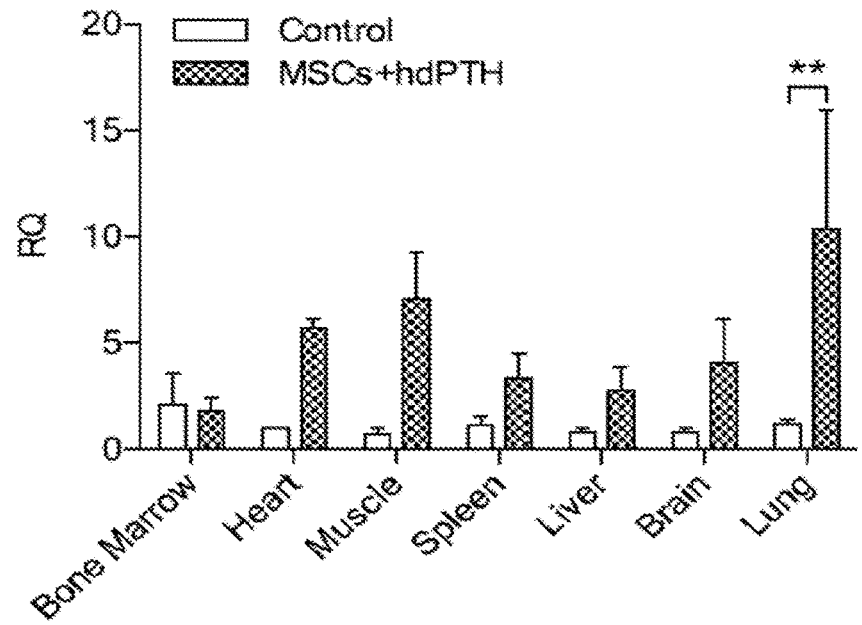
FIG. 20(A) to FIG. 20(B). Biodistribution of cells following systemic administration. Rat tissues (brain, bone marrow, heart, lungs, muscle, spleen, and liver) were harvested postmortem for biopsy to study the biodistribution of hMSCs 12 weeks postop (9 weeks after the last stem cell injection). DNA was extracted, and the presence of donor cell DNA was evaluated using PCR for the reporter gene Luc (A). Minipig tissues (brain, bone marrow, heart, lungs, muscle, spleen, and liver) were harvested postmortem for biopsy to study the biodistribution of pMSCs 5 weeks postop (1 week after the last stem cell injection) in the various treatment groups. DNA was extracted, and the presence of donor cell DNA was evaluated using PCR for the reporter gene Luc (B). *p≤0.05, p≤0.01, *p≤0.001, ****p≤0.0001.

14B), an indication of bone formation, and apparent density (AD; FIG. 14C), an indication of bone quality. The results indicated minimal bone regeneration during the first 2 weeks postop and no additional bone formation at later time points in the control and hMSCs groups (FIG. 14-C). New bone formed mostly at the edges of the defect (FIG. 14A). No significant differences in either BVD or AD were found between the two groups (p>0.05) at any time point. Significantly enhanced bone formation was not found in rats treated with ldPTH, compared with the control groups (p>0.05; FIG. 14B). Only in rats treated with hMSCs+ldPTH was increased formation of cortical and trabecular bone evident on both 2D tomographic images and 3D reconstructed images as soon as Week 2 postop (FIG. 14A). At this time point, significantly higher BVD (p≤0.05; FIG. 14B) and AD (p≤0.01; FIG. 14C) values were found in the hMSCs+ldPTH group than in the control and single-treatment groups. Both hMSCs+PTH treatments were superior to all other treatments except hdPTH alone, in BVD at 4 weeks postop (p≤0.01; FIG. 14B). By Week 8, bone formation in the hMSCs+ldPTH group was sufficient to regenerate the cortex completely and restore the structural integrity of the vertebrae, whereas in rats in the control groups there was clearly cortical discontinuity and lower bone mass (FIG. 14A). Interestingly, while no significant difference in BVD was found between the hMSCs+hdPTH group and the ldPTH group at any time point (p>0.05; FIG. 14B), a significant difference in AD was found at Week 8 between these two groups (p≤0.01; FIG. 14C). Histological analysis showed that there was too little regrowth to regenerate cortex or trabeculae in the control and MSCs groups (FIG. 15A). In ldPTH-treated animals the defect was partially regenerated, but only in hMSCs+ldPTH-treated animals (FIG. 15A) were both cortex and trabeculae regenerated. Similar trends were found for the hdPTH and hMSCs+hdPTH groups (FIG. 20A).

Example 24

Fate of IV Injected hMSCs

Figure 15B:
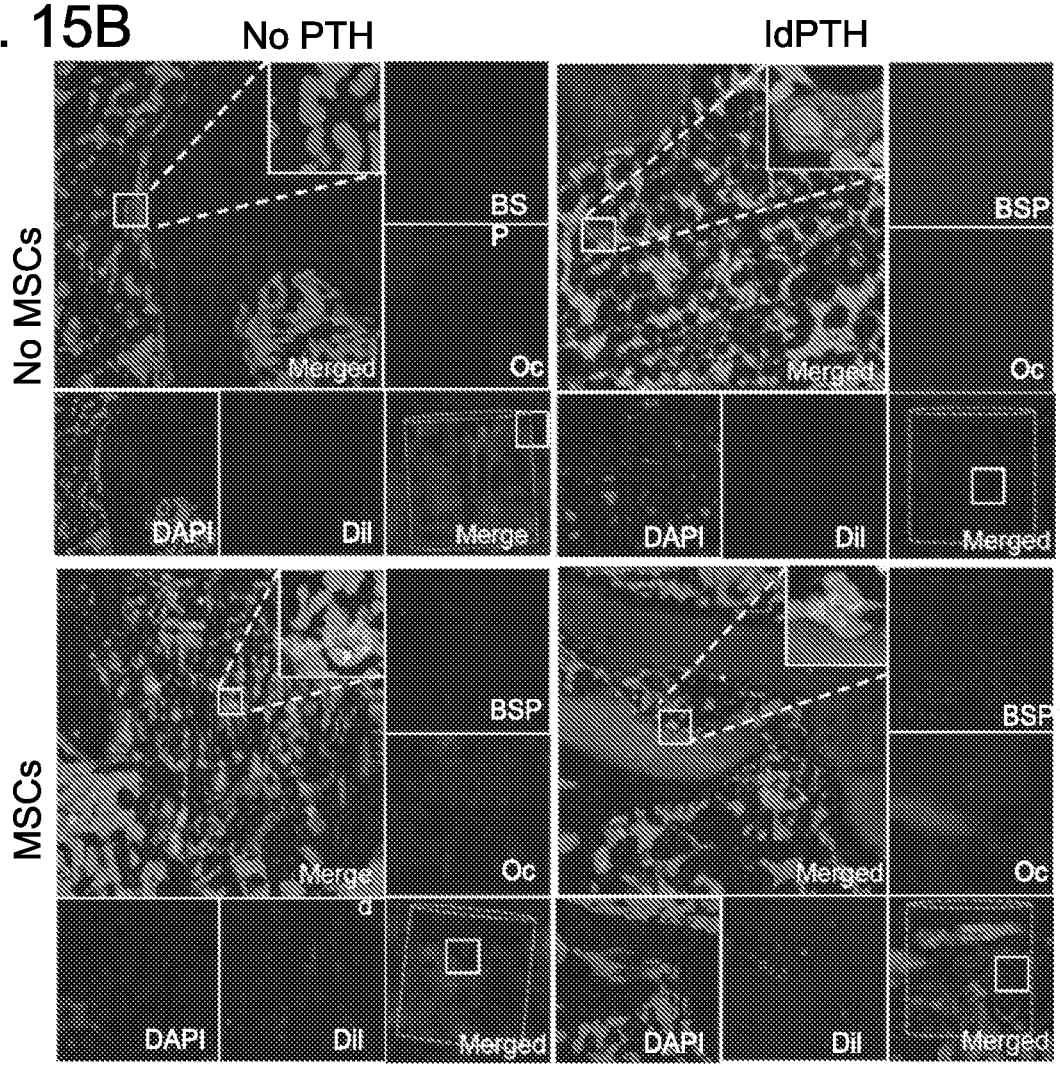
Figure 20B:
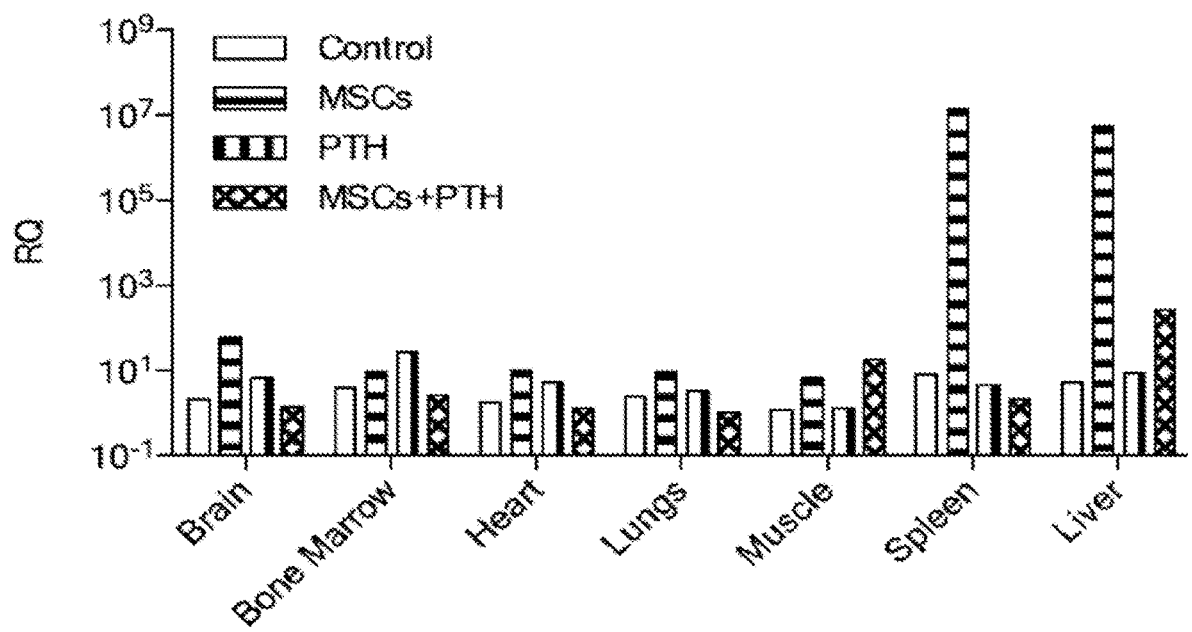
Figure 21A:
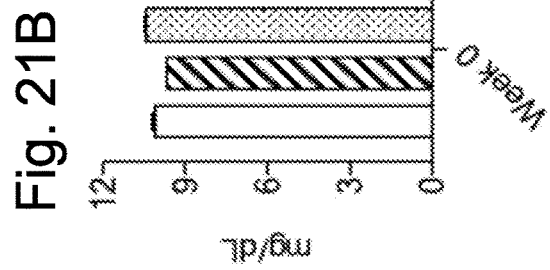
FIG. 21(A) to FIG. 21(E). MSCs-hdPTH therapy regenerates vertebral defects in osteoporotic rats: histological and immunofluorescence analysis. Injured vertebrae were harvested, decalcified, embedded in paraffin, sectioned, and stained with standard H&E (A). Slides containing tissue stained against the osteogenic markers osteocalcin (Oc) and bone sialoprotein (BSP) showed that the markers were partially colocalized with DAPI-stained nuclei and DiI fluorescent dye, with which the MSCs had been labeled prior to their systemic administration (B). Slides containing tissue stained against the homing markers of both SDF1/CXCR4 (C) and Amp/EGFR (D) pathways also showed that those markers were partially colocalized with DAPI-stained nuclei and DiI fluorescent dye, with which the hMSCs had been labeled prior to their systemic administration. Minipig blood drawn 1 and 5 weeks postop was tested for phosphorous (A), calcium (B), ALP (C), creatinine (D), and albumin (E).
Figure 21B:
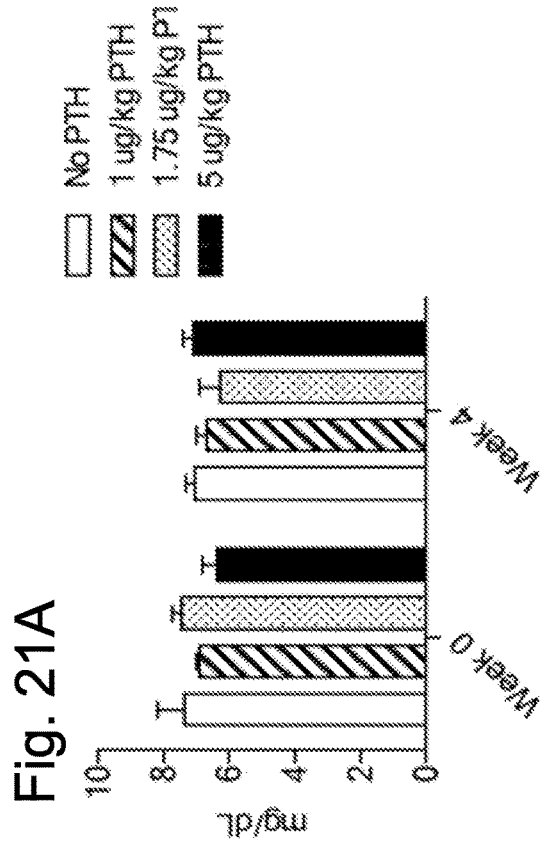
Figure 21C:
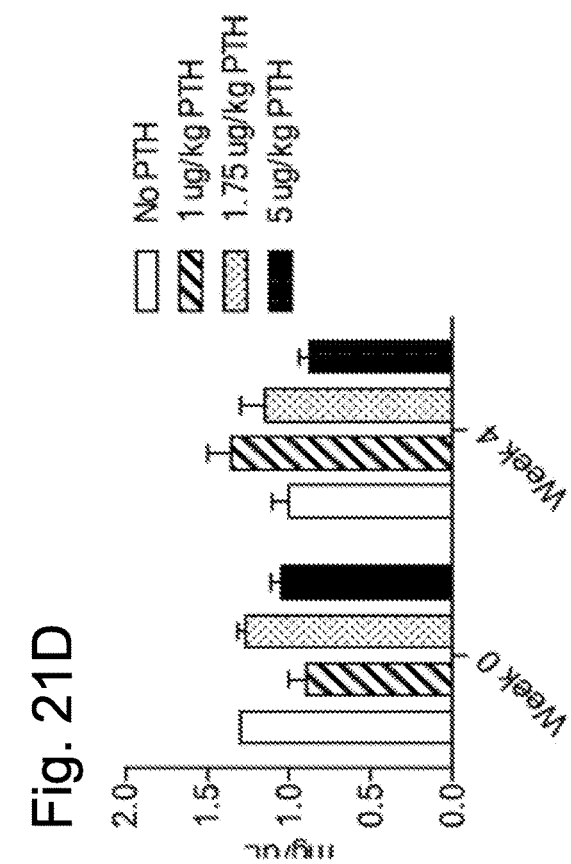
Figure 21D:
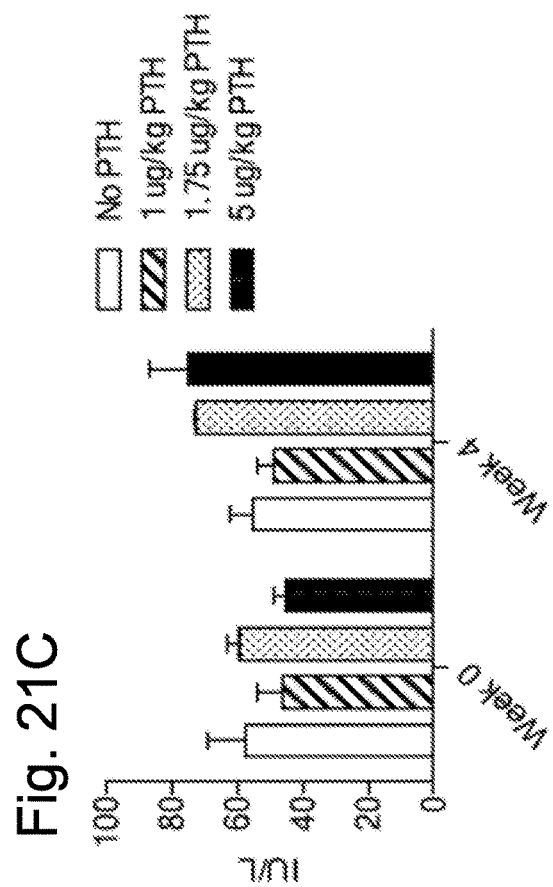
Figure 21E:
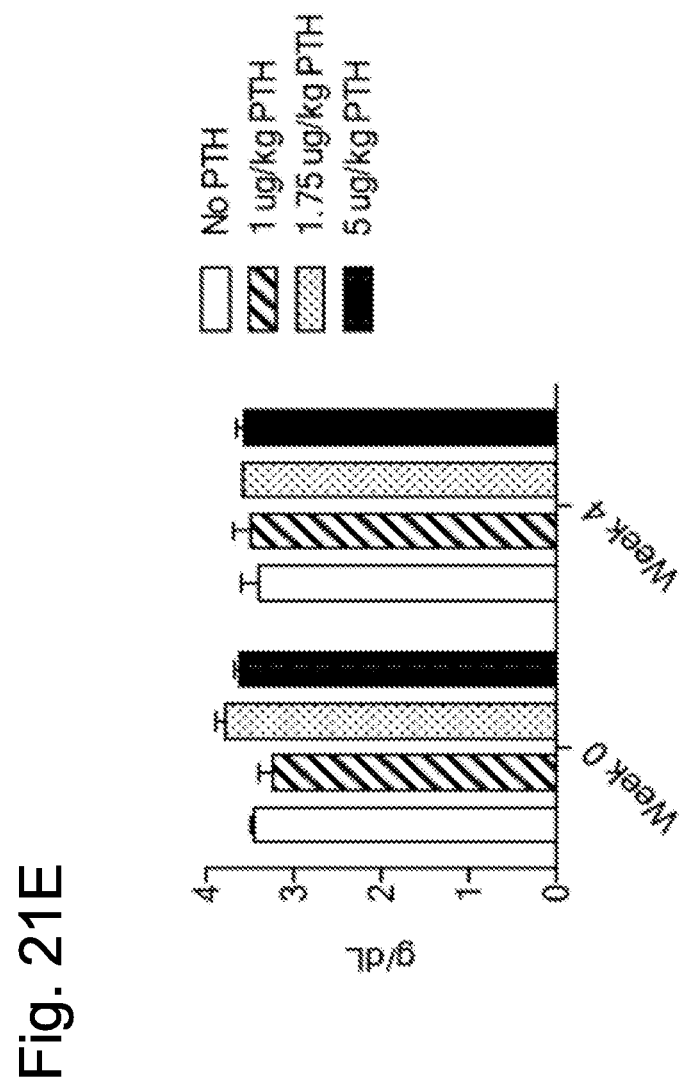

To investigate the contribution of systemically administered MSCs to vertebral defect regeneration, the Inventors labeled these cells with DiI before injection and later stained retrieved tissue sections with immunofluorescent antibodies against the osteogenic markers bone sialoprotein (BSP) and osteocalcin (Os). Although the Inventors used antibodies against human osteogenic markers, some cross-reactivity with rat proteins was expected, and thus not all osteogenic cells were colocalized with the DiI-stained donor human cells (FIG. 15B), indicating contribution of host cells. The DiI-stained cells were found in vertebral defects in all MSCs-injected groups; however, the abundance of cells appeared qualitatively higher in animals that were also treated with PTH. Many injected cells were found in cancellous bone, where new tissue formed, but not in the cortical region. Colocalization of DiI-stained cells and Oc and BSP showed that some of the injected cells expressed either or both differentiation markers, while others expressed neither. Some staining for osteogenic markers was observed in the PTH-treated groups; this was probably due to the anabolic effects of PTH. Importantly, more cells were visible in the regenerated defects of MSC-PTH-treated rats. In addition to the microscopic detection of MSCs in the defect area, the systemic biodistribution of these cells was evaluated using PCR against Luc2. Evidence of MSCs was found only in the animals' lungs (FIG. 20).

Example 25

Expression of Cell Migration and Chemo-Attraction Molecules

Figure 16A:
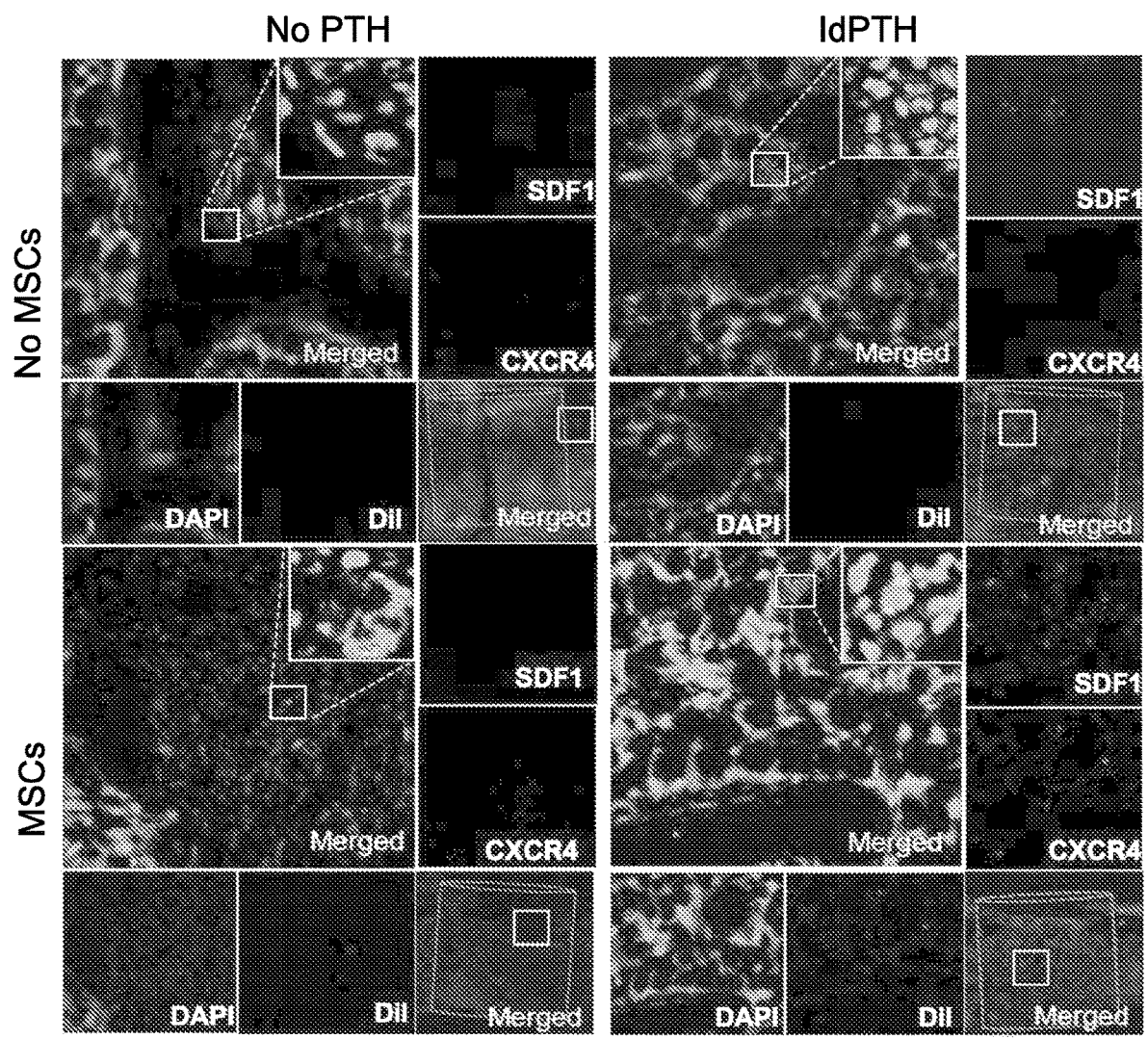
FIG. 16(A) to FIG. 16(B). PTH enhances homing of MSCs to the defect site via two pathways: confocal imaging of immunofluorescent staining. The injured rat vertebrae were harvested, decalcified, embedded in paraffin, sectioned, stained with immunofluorescent staining against the SDF1 and CXCR4 markers to detect MSC homing, and imaged using confocal microscopy (A). Another set of slides containing tissue was stained with immunofluorescent staining against EGFR and amphiregulin (Amp) (B). The homing markers of both pathways could be colocalized with DAPI-stained nuclei and DiI fluorescent dye, which was used to label MSCs prior to systemic administration.
Figure 16B:
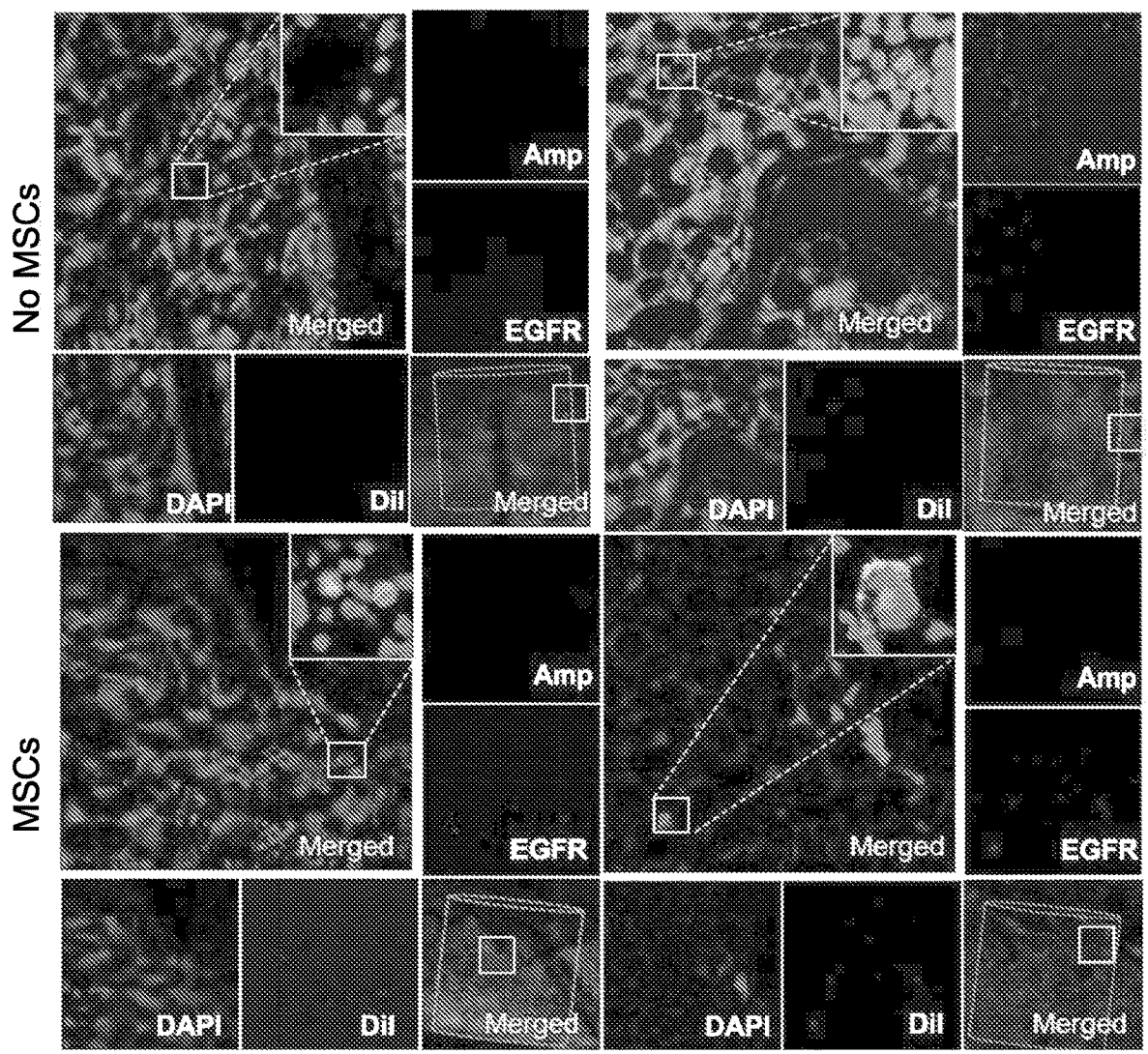

To look into the mechanism of PTH-induced stem cell homing to vertebral defects, the Inventors assessed the activation of two previously investigated pathways of cell migration. First, the Inventors investigated the most extensively studied pathway of stem cell mobilization and homing to injury sites, the SDF1/CXCR4 axis, which is known to be enhanced by PTH therapy. In this study the Inventors stained harvested vertebrae sections to determine the expression of SDF1 by host cells in the defect site and that of CXCR4, a receptor for SDF1, which reportedly is expressed by homing cells. The Inventors found SDF1-expressing cells in the vertebral defects of PTH-treated animals that had been treated with or without hMSCs, but no SDF-1 expression in the control group. As for CXCR4, the Inventors detected a few positive cells in tissue from animals in the hMSC-streated group, some of which could be colocalized with DiI-labeled donor cells (FIG. 16A). In the MSCs-PTH treated groups, the Inventors found abundant DiI-labeled MSCs co-expressing CXCR4, while SDF1 expression was limited to host cells within and at the margins of the defect. The Inventors found no CXCR4 expression in the PTH-treated groups. It has been reported that that PTH also attracts MSCs to injury sites by stimulating expression of amphiregulin, an epidermal growth factor (EGF)-like ligand that signals through the EGF receptor (EGFR), in both osteoblasts and osteocytes. Here the Inventors stained the vertebral defect sites with antibodies against both the secreted ligand (amphiregulin) and the receptor (EGFR). Similarly to SDF1/CXCR4 expression, amphiregulin was detected in the PTH groups and EGFR staining was colocalized with DiI-labeled MSCs (FIG. 16B).

Example 26

Pilot Pig Study

Following the results of the rat study, the Inventors investigated the effect of the combined MSCsPTH treatment on vertebral bone regeneration in an immunocompetent large animal model. Bone defects were created in the lumber vertebrae of minipigs (FIG. 12B), similarly to what was previously reported. The minipigs were treated with either four IV injections of allogeneic porcine MSCs (pMSCs) or PBS once a week and with daily subcutaneous (SQ) injections of PBS or 1.75 µg/kg PTH for 4 weeks. Bone formation was monitored using in vivo xray fluoroscopy followed by ex vivo µCT scanning. The Inventors analyzed nine defects for each group (three pigs with three defects each).

Example 27

Bone Regeneration in Minipig Vertebral Defects

Figure 17A:
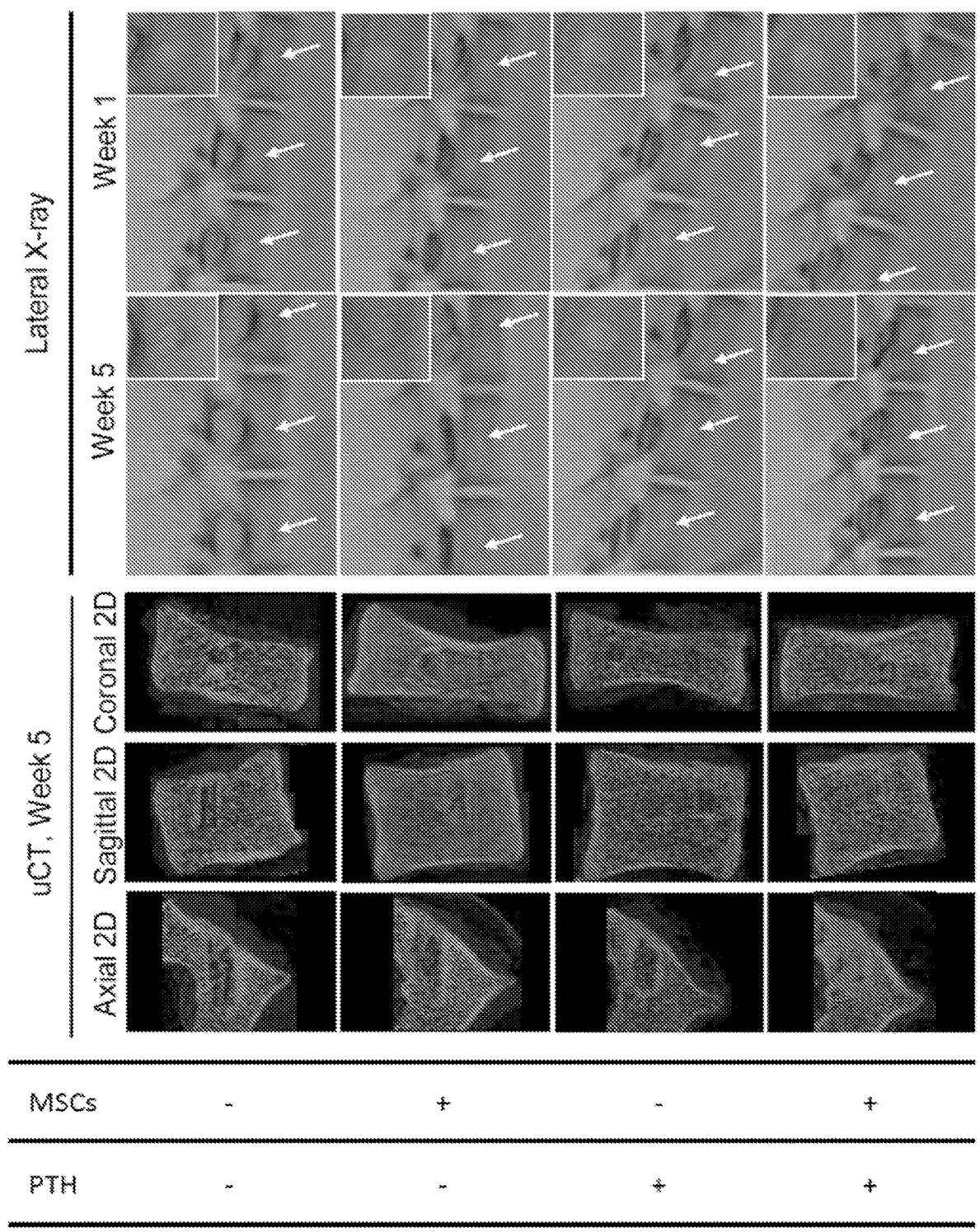
FIG. 17(A) to FIG. 17(C). MSCs-PTH therapy regenerates minipig vertebral defects: in vivo x-ray and μCT imaging. Vertebral bone voids treated with MSCs or saline and with PTH or PBS were imaged in vivo using x-ray fluoroscopy on Weeks 1 and 5 postop and ex vivo using μCT. (A) Representative radiographs of L2-4 for each group are shown with white arrows pointing at the voids and a magnification of one of these voids in the upper left inset in each panel. Representative coronal, sagittal, and axial 2D μCT images are also shown for each group. A quantitative analysis of bone formation in the voids was performed, and bone volume density (B) and apparent density (C) were calculated and compared using a two-way ANOVA (n=9).
Figure 17B:
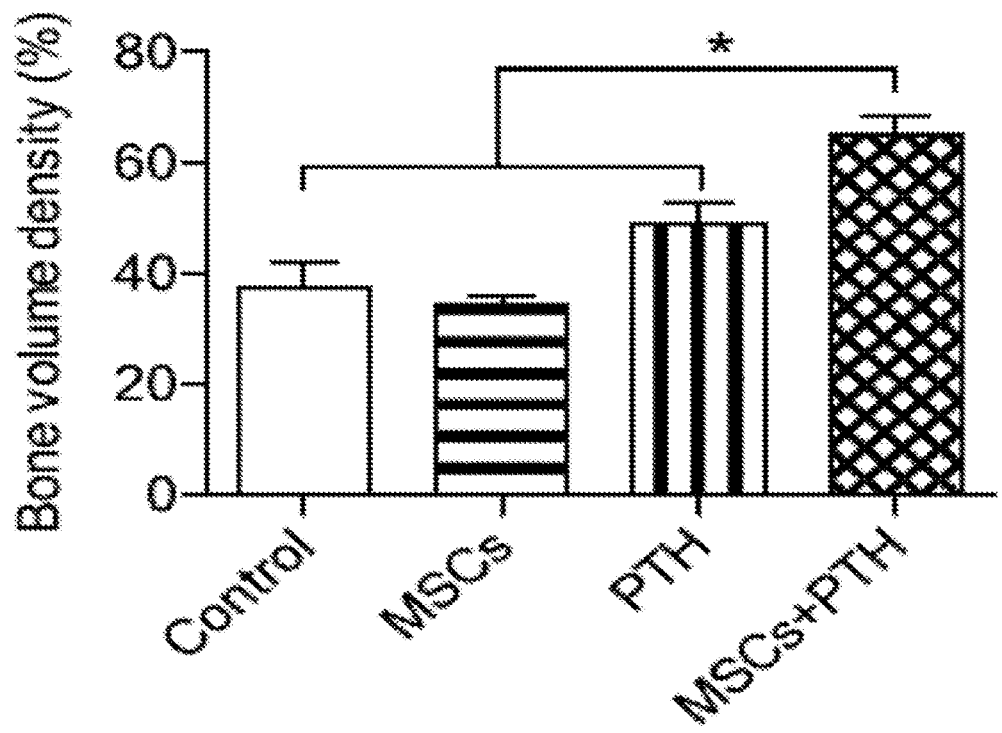
Figure 17C:
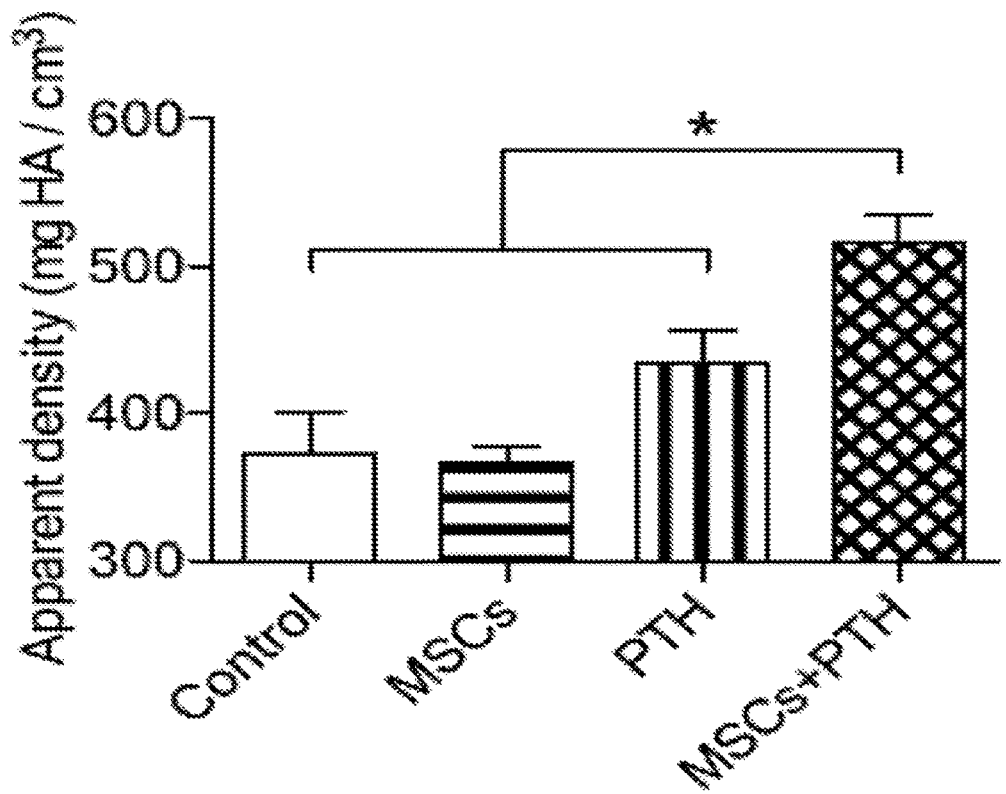
Figure 18A:
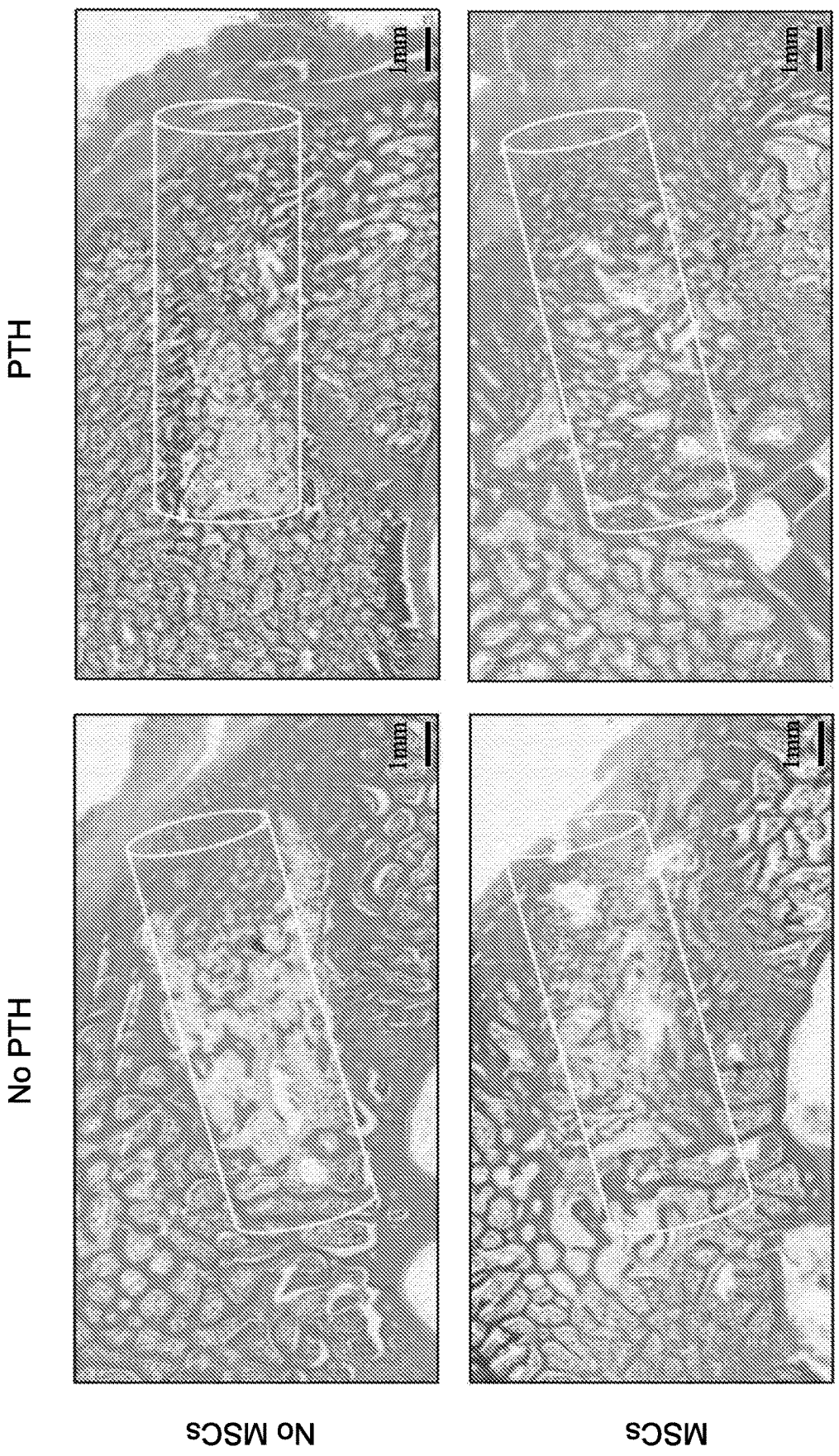
FIG. 18(A) to FIG. 18(B). MSCs-PTH therapy regenerates vertebral defects in minipigs: histological and immunofluorescence analyses. Injured vertebrae were harvested, decalcified, embedded in paraffin, sectioned, and either stained with standard H&E and imaged with light microscopy (A) or treated with immunofluorescent staining against the osteogenic markers Oc and BSP as well as the reporter gene Luc, and imaged using confocal microscopy (B). Representative vertebral defects show the healing progress in the various groups with or without PTH and MSCs (B). The osteogenic markers can be partially colocalized with DAPI-stained nuclei and DiI fluorescent dye, which was used to label the MSCs prior to systemic administration (B).

Lateral x-ray films obtained few days postop showed radiolucent defects that were similar in size and anatomical location (FIG. 17A). On postop Week 5 these defects remained clearly visible in all control groups but not in the pMSCs+PTH group. In the control groups, a radiopaque rim indicated bone formation at the circumference of the defect site, but the defects themselves did not appear to have healed because they remained more radiolucent than the tissue around them. In contrast, in minipigs treated with pMSCs+PTH the defect sites themselves were more radiopaque than surrounding uncompromised tissue, indicating that the previously missing bone had regenerated at a greater mineral density than native vertebral bone. The x-ray findings were corroborated by a μCT analysis, which indicated that the BVDs (p≤0.05; FIG. 17B) and ADs (p≤0.05; FIG. 17C) of defect sites treated with pMSCs+PTH were about two times higher than those measured in controls. In conclusion, only minipigs treated with both pMSCs+PTH showed complete healing of the bone defect, while neither treatment alone seemed to affect the healing process (p>0.05; FIG. 17B, C). Histological analysis showed that, in the control groups, there was cortex-like formation of dense bone at the edges of the defect; whereas in the MSC-PTH-treated group, the defect site was filled with trabecular bone that was denser than surrounding uncompromised vertebral bone (FIG. 18A).

Example 28

Fate of IV Injected pMSCs

Figure 18B:
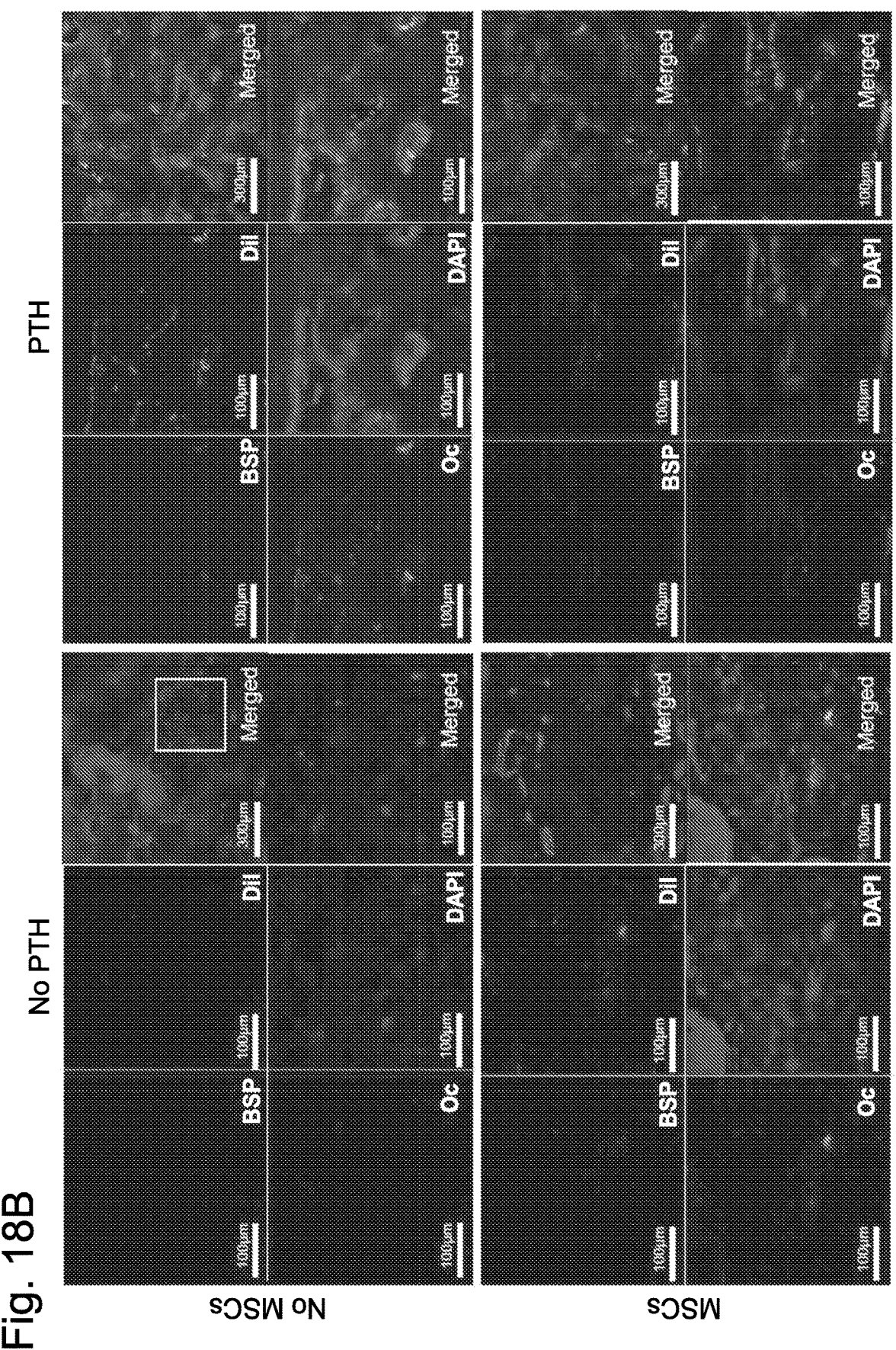

The contribution of allogeneic porcine MSCs to the regeneration of bone defects was detected using fluorescence microscopy and imaging of the IV injected DiI-labeled cells (FIG. 18B, C). Similarly to the rat model, administered cells were found mostly in the region of the defect, in the bone marrow of newly formed bone tissue and not incorporated in the trabecular bone tissue itself. Also, similarly to the rats, some of the cells were colocalized with Osexpressing cells, indicating osteogenic differentiation. In addition to MSCs found at the defect site, other MSCs were detected in the spleen and liver, but not in pigs treated with pMSCs+PTH (FIG. 21).

Example 29

Figure 19:
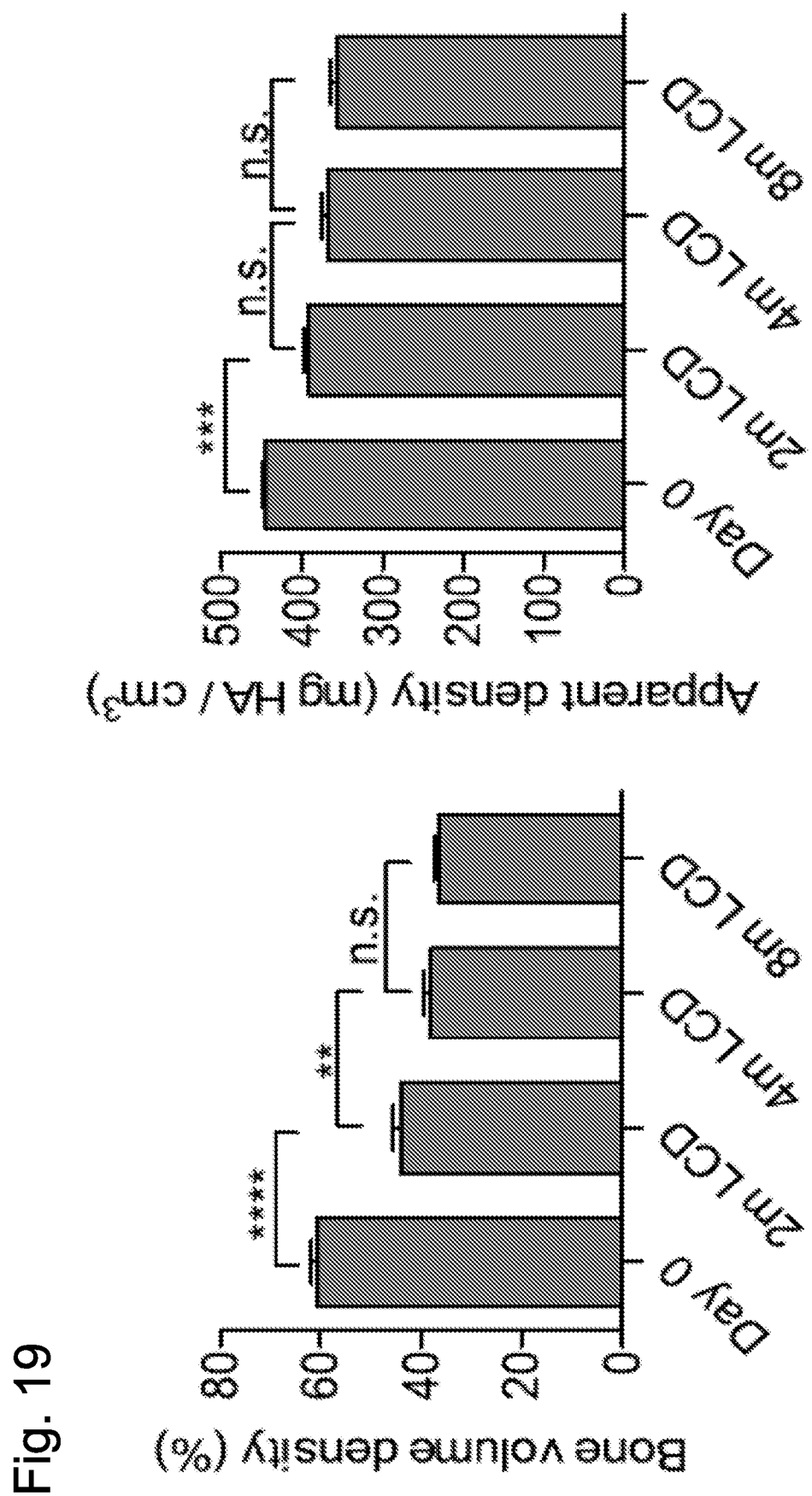
FIG. 19. Establishment of the osteoporosis induction protocol in ovariectomized nude rats. Quantitative μCT analysis demonstrates reductions in bone volume density and apparent density in intact lumbar vertebrae after 2, 4, and 8 months of LCD. *p≤0.05, p≤0.01, *p≤0.001, ****p≤0.0001.

Determination of the Optimal Duration of the Low-Calcium Diet for Induction of Osteoporosis To determine the optimal duration of the LCD, ovariectomized rats were subjected to 8 months of the LCD, during which bone mineral loss in intact vertebrae was evaluated using microcomputerized tomography (μCT). Significant decreases in bone volume density (BVD) and apparent density (AD) were observed after 2 months of LCD (FIG. 19). While BVD continued to decrease for 2 more months (that is, for a total of 4 months of LCD), the AD remained fairly constant after 2 months. Maintaining an LCD for 8 months produced no significant differences in effects on bone density and other structural parameters when compared to an LCD lasting 4 months. Therefore, a 4-month-long LCD was chosen to induce osteoporosis in ovariectomized nude rats.

Example 30

MSC Biodistribution Assay

Different organs (brain, bone marrow, liver, lungs, heart muscle, skeletal muscle, and spleen) were biopsied immediately after the animal had been euthanized and were snap-frozen. Then the tissues were homogenized, and DNA was extracted using a DNA extraction kit (Qiagen, Valencia, Calif.). Since both rats and pigs received systemic administration of MSCs transduced to express Luciferase (Luc), the DNA samples were tested for Luc expression using quantitative PCR and normalized to the 18S housekeeping gene.

Example 31

Effects of PTH Treatment on Metabolic Biomarkers

Figure 22C:
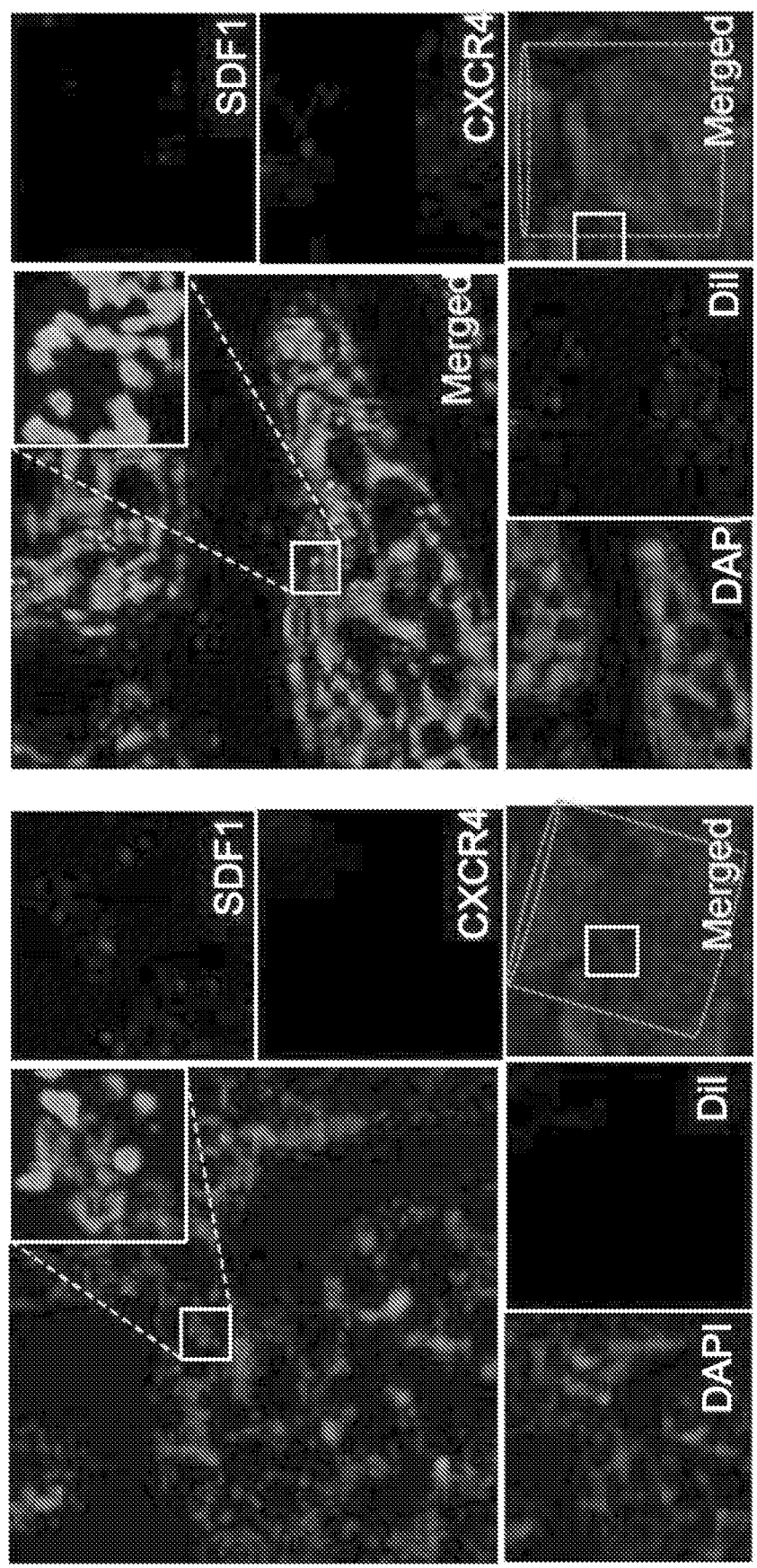
Figure 22D:
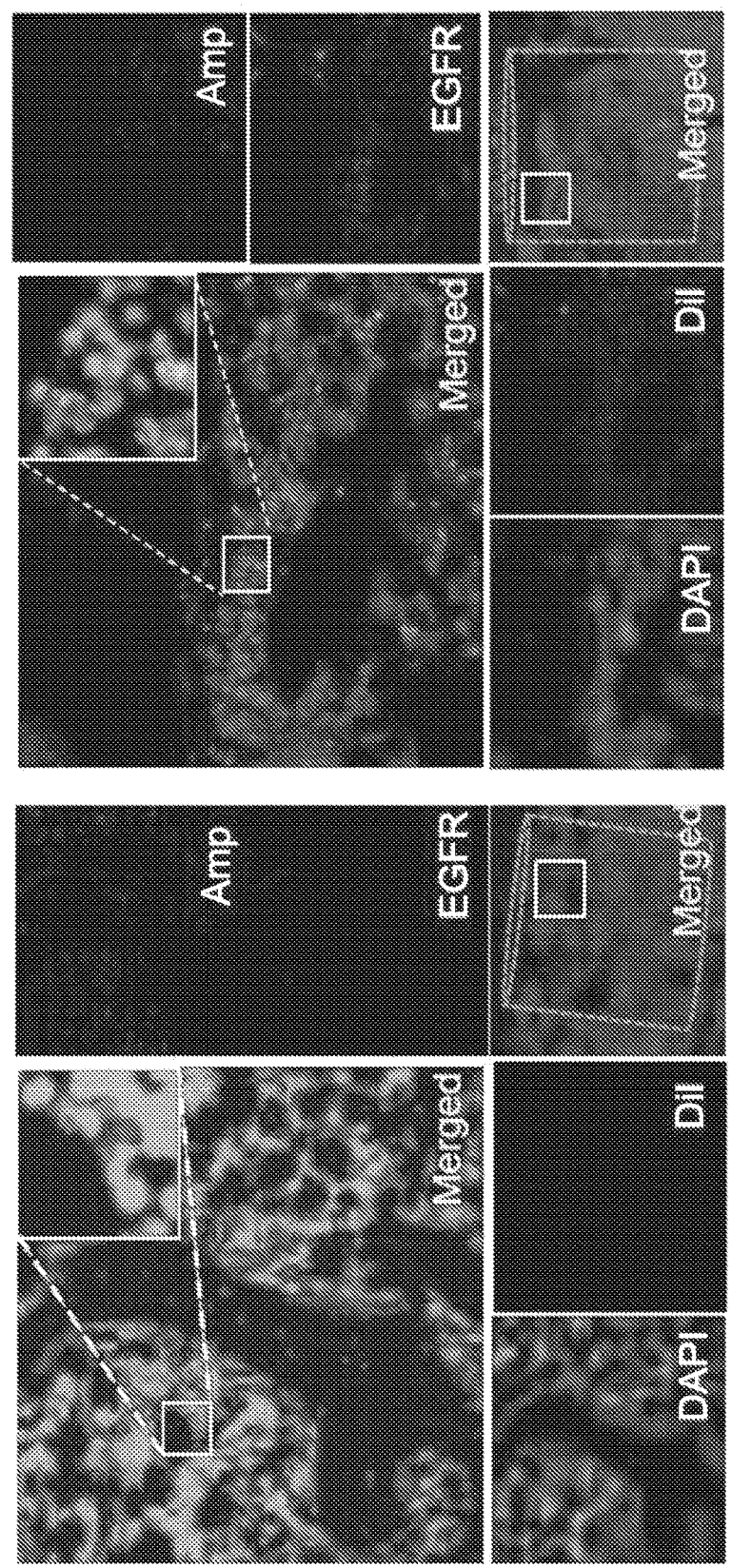

Hypercalcemia is a major concern following PTH treatment. Therefore, the pigs were treated with different doses of PTH (up to 5 μg/kg) for 4 weeks and their blood serum was analyzed. No changes were found in calcium and phosphate serum levels in any treatment group. Creatinine levels in the serum were sustained throughout treatment, indicating normal kidney function. No changes were observed in any of the pigs' metabolic biomarkers. The treatment did not affect levels of alkaline phosphatase (ALP) or albumin, indicating no impairment in liver function or bone turnover, respectively (FIGS. 22 A-E). These results show that increasing dosages of PTH administered for a short period are well tolerated, without producing systemic effects, and are therefore safe.

Example 32

Fate of hMSCs in Osteoporotic Rats Treated with hdPTH

Osteoporotic rats were treated with two different dosages of teriparatide (Forteo™, Eli Lilly, Indianapolis, Ind.)—0.4 μg/kg/day (ldPTH) or 4 μg/kg/day (hdPTH). To investigate the contribution of systemically administered hMSCs to vertebral defect regeneration, we labeled these cells with DiI before injection and later stained retrieved tissue sections with immunofluorescent antibodies against the osteogenic markers bone sialoprotein (BSP) and osteocalcin (Os). In addition, to investigate the mechanism of PTH-induced stem cell homing to vertebral defects, we assessed the activation of two previously investigated pathways of cell migration: SDF1/CXCR4 and Amp/EGFR. Results showed that in both PTH doses we found DiI-labeled hMSCs co-expressing the osteogenic markers and the CXCR and EGF receptors.

Example 33

Discussion

The Inventors' results showed that vertebral defects created in osteoporotic rats and in healthy pigs were efficiently repaired following combined MSCs+PTH treatment. This contrasts with the results in animals that received either treatment alone or no treatment. Moreover, administration of PTH enhanced hMSC homing to vertebral bone defects.

Current treatment of patients with osteoporosis mostly focuses on OVCF prevention using medicines such as alendronate sodium and PTH. Teriparatide (the 1-34 portion of PTH) is the only FDA-approved osteoporosis anabolic agent. Preclinical studies support the potential for PTH as a treatment for bone fractures. Einhorn and colleagues demonstrated that PTH improves fracture callus quality, increases bone mineral content and density, and accelerates endochondral ossification in a rat femur diaphyseal fracture model. Some have investigated the mechanisms underlying PTH-accelerated long-bone fracture repair by assessing the phenotype of MSCs from mice treated with 40 μg/kg PTH or saline for 7 days. Their results showed that PTH induced the osteoblast transcription factors Osx and Runx2 in MSCs and accelerated osteoblast maturation and fracture healing in these mice. Other reports demonstrated that PTH stimulates MSC recruitment to bone by inducing CXCL12 and SDF1 expression in osteoblasts.

In randomized clinical trials in which PTH was tested to aid fracture healing, however, conflicting results were found. This difference in results may be related to differences in study design including the fracture site and PTH dosage, and thus more evidence is needed to know if teriparatide alone accelerates fracture repair. In the present study the Inventors showed in a rat model of osteoporosis that a clinically relevant dosage of PTH had a limited effect on vertebral bone repair and was significantly inferior to the combined therapy of PTH and MSCs.

The anabolic effects of PTH include increases in skeletal mass, bone turnover, and bone strength. However, continuous release of excess endogenous PTH, as occurs in hyperparathyroidism, may be detrimental to the skeleton because bone resorption is stimulated more than bone formation, which limits the duration of safe treatment. Therefore, the dosage of PTH and the duration of intermittent administration play a critical role in therapeutic outcome. Currently, the FDA-approved treatment is 20 µg/day (~0.3-0.5 µg/kg) for up to 2 years. The dosage used in preclinical studies to enhance fracture repair is 0.4 µg/kg-40 µg/kg in small animals and 1 µg/kg-5 µg/kg in large animals. Some studies showed a clear dose response to PTH, whereas other studies showed that higher dosages of PTH did not necessarily provide better outcomes. In agreement with findings in the latter studies, the Inventors' results showed that a dosage of 0.4 µg/kg (ldPTH, equivalent to the clinical dosage of 20 µg/day) was more successful in accelerating the repair of a bone defect in osteoporotic rats. The Inventors' results in pigs were achieved using a higher dosage (1.75 µg/kg); however, this is a much lower dosage than those reported in other large animals studies.

This study demonstrates effective regeneration of vertebral defects that mimic compression fractures by using noninvasive systemic stem-cell-and-hormone therapy. Several sessions of IV cell administration in combination with a few weeks of PTH therapy led to remarkable regeneration of vertebral defects in rodent (FIGS. 14, 15) and large animal porcine (FIGS. 17, 18) models. The rodent model enabled us to test the Inventors' hypothesis in osteoporotic animals, in which the healing of bone defects is severely impaired. Since the combined therapy successfully overcame this obstacle, the Inventors believe that a similar therapy in patients with osteoporosis could prove successful as well. Furthermore, using immunocompromised animals, the Inventors could specifically test the homing and differentiation of human MSCs. Here the Inventors used minipigs, exploiting the similarity between the size of their skeletons and those of humans. Although all of the pigs were healthy, animals in the control groups did not regenerate defects within 5 weeks (FIGS. 17, 18). Additionally the MSCs utilized in the pig study were allogeneic and were injected without any immunosuppression therapy, since MSCs are known for their immunoprivileged and immunomodulatory properties. The results of this study reinforce accumulating evidence that allogeneic MSCs can be used systemically without immunosuppression therapy; this has an advantage for future therapy in human clinical practice.

Surprisingly, most of the bone formed in the rat vertebral defects was found during the first 2-4 weeks postop, as evident from the results of the bone volume quantification tests (FIG. 14B). Whereas the effect of the treatment on mineral density was mostly evident in the long term (FIG. 14C).

The contribution of MSCs to the regeneration of vertebral defects was evident. It is difficult to estimate what fraction of cells administered actually homed to the site of interest, but both in vivo imaging and IHF analysis detected significant populations of cells residing in the defect and nearby. Interestingly, most donor cells, which were detected using DiI, were not incorporated in new bone as osteocytes, but were found in the bone marrow of new bone, indicating a more regulatory role in the regeneration process, rather than differentiation towards osteocytes and matrix secretion.

Colocalization of the DiI-stained cells and osteogenic markers showed that donor cells are not synchronized in their differentiation: some cells expressed one of the markers; some cells expressed both markers; and some didn't express any at all. This finding is probably due the fact that the administered cells homed to the site of the defect at different stages in the therapy, and thus were in different stages of differentiation.

Previous studies investigated the use of small molecules to enhance homing and targeting to bone on the part of IV injected MSCs. However, in those studies researchers did not investigate the capacity of MSCs to induce bone regeneration in an injury model, but rather their ability to augment intact bone structures. Here the Inventors showed that PTH had a significant effect on homing of MSCs to vertebral bone defects. The homing mechanism that can be enhanced by PTH has not been fully described yet; however, several of its components have been investigated and confirmed. The Inventors' results show that PTH increases homing of host MSCs to the injury site possibly via multiple pathways in addition to PTH's well-established osteo-anabolic effect. The main difference between the Inventors' findings and those of previous reports is that the Inventors found that PTH plays an adjuvant role in stem cell therapy and can be given at a minimal dosage for the minimal period of time required to support the homing and differentiation of multiple systemic cell injections. The Inventors' results show that hMSCs homed to the injured vertebrae and differentiated into osteoblasts. Interestingly, hMSCs homed to the defect site in a dose-dependent manner in response to PTH administration. However, the therapeutic effect of the dosage that induced significantly higher homing of MSCs (4 µg/kg) was not significantly different from the lower dosage (0.4 µg/kg). While the Inventors could not directly measure cell homing in pigs, the Inventors did find that when pigs were given PTH, no MSCs were found in the spleen or liver (SF2), suggesting that PTH decreases off-target biodistribution and increases MSC homing to injury sites.

A limitation of the present study is the inability to verify the Inventors' results in an osteoporotic large animal. Very few attempts have been made to generate osteoporotic pigs, and so far these have not been quite established and are extremely costly. The Inventors' safety studies show retention of administered MSCs only in intended vertebral bodies and no indication of PTH toxicity even at dosages higher than the therapeutic 1.75 µg/kg. However, these are very limited studies and should be extended in order to bring this therapy to clinical use.

The present study provides evidence for future therapies that could revolutionize the treatment of vertebral and other complex fractures, especially in patients with osteoporosis. This is a critical step towards the development of allogeneic MSCs as a therapeutic candidate to treat OVCFs. The advantage of allogeneic cells is that they do not require the patient to undergo an additional medical procedure such as bone marrow aspiration. The systemic approach holds an additional monumental advantage, making noninvasive treatment of multiple OVCFs possible for the first time.

Example 34

Systemic MSC and PTH Therapy for Life-Endangering Rib Fractures

Figure 23A:
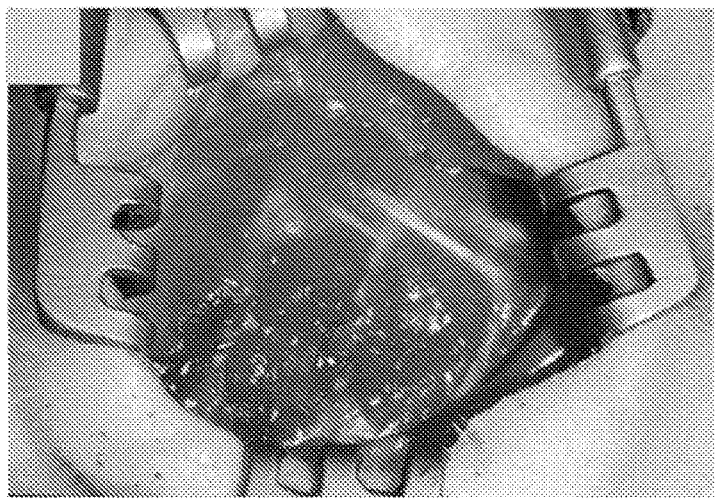
Figure 23B:
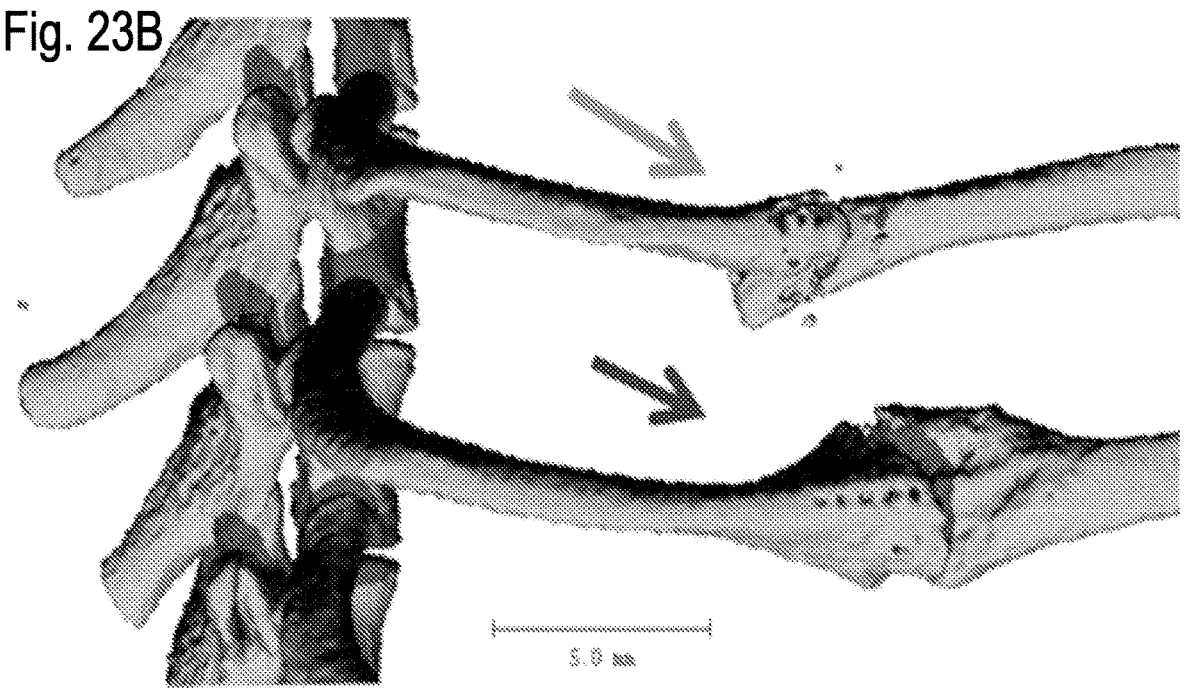

The Inventors developed a novel combined approach to treat RFs, composed of systemic intravenous administration of MSCs and PTH therapy. First, the Inventors created a rat model of multiple rib fractures (FIG. 23A) and observed prominent formation of bone callus (FIG. 23B). Nevertheless the defect margins did not unify (FIG. 23C).

Example 35

Increased MSC Homing and Repair at Rib Fracture Sites

Next, MSCs were harvested from human bone marrow, and tagged using constitutive Luciferase expression (FIG. 24A). $2*10^6$ hMSCs were injected to the rat-tail vein repeatedly 3, 7, 10, 14 and 17 days after surgery. In parallel, the rats were given daily subcutaneous injections of 4 ug/kg PTH analog (Teriparatide). A week after the surgery, prominent bioluminescent signal was detected at the fracture site (FIG. 24B) indicating cell homing to the fracture site. 14 days after surgery, in-vivo uCT analysis showed fracture repair in rats treated with hMSCs and PTH compared to untreated rats, in which the fractures remained un-bridged.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the methods for preventing or treating osteoporotic patients and related conditions, such as fractures, methods of isolating or modifying mesenchymal stem cells used in the described techniques, compositions of therapeutic agents and/or mesenchymal stem cells generated by the aforementioned techniques, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of treating an osteoporotic related vertebral compression fracture, comprising:
   selecting a human subject;
   administering a quantity of at least $2 \times 10^6$ human mesenchymal stem cells (MSCs) and a quantity of about 0.2-4 µg/kg of parathyroid hormone (PTH) to the human subject; and
   continuing to administer about 0.2-4 µg/kg of PTH each day for at least 1 week, wherein administration of human MSCs comprises intravenous injection, and administration of PTH comprises subcutaneous injection, and wherein administration of both MSCs and PTH treats the osteoporotic related vertebral compression fracture by increasing apparent density (AD) at week eight that is greater than non-treatment, MSC treatment alone, and PTH treatment alone.

2. The method of claim 1, wherein the MSCs are derived from bone marrow or adipose tissue and express CD90+, CD44+, CD29+, CD73+, and CD105+.

3. The method of claim 1, further comprising administration of the quantity of at least $2 \times 10^6$ human MSCs every three days for up to 15 days.

4. The method of claim 1, wherein subcutaneous injection is at the thigh or abdomen.

* * * * *